United States Patent
Peterson et al.

(10) Patent No.: US 9,713,472 B2
(45) Date of Patent: *Jul. 25, 2017

(54) MECHANICAL METHOD AND APPARATUS FOR BILATERAL TISSUE FASTENING

(71) Applicant: Incisive Surgical, Inc., Plymouth, MN (US)

(72) Inventors: James A. Peterson, Edina, MN (US); Christopher J. Sperry, Plymouth, MN (US); Joseph M. Gryskiewicz, Edina, MN (US); Delmer L. Smith, Edina, MN (US); David B. Herridge, Mendota Heights, MN (US)

(73) Assignee: Incisive Surgical, Inc., Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/145,194

(22) Filed: May 3, 2016

(65) Prior Publication Data

US 2016/0242772 A1    Aug. 25, 2016

Related U.S. Application Data

(60) Continuation of application No. 14/471,519, filed on Aug. 28, 2014, now abandoned, which is a
(Continued)

(51) Int. Cl.
*A61B 17/068* (2006.01)
*A61B 17/064* (2006.01)
(Continued)

(52) U.S. Cl.
CPC ........ *A61B 17/0682* (2013.01); *A61B 17/064* (2013.01); *A61B 17/068* (2013.01);
(Continued)

(58) Field of Classification Search
CPC ... A61B 17/0682; A61B 17/08; A61B 17/068; A61B 17/0644; A61B 17/064;
(Continued)

(56) References Cited

U.S. PATENT DOCUMENTS

| 718,649 A | 1/1903 | Morehouse |
|---|---|---|
| 2,283,814 A | 5/1942 | La Place |

(Continued)

FOREIGN PATENT DOCUMENTS

| EP | 0657139 B1 | 3/2003 |
|---|---|---|
| EP | 1 323 384 A2 | 7/2003 |

(Continued)

OTHER PUBLICATIONS

Application and File history for U.S. Appl. No. 14/262,071, filed Apr. 25, 2014. Inventors: Peterson et al.
(Continued)

*Primary Examiner* — Katherine M Shi
*Assistant Examiner* — Michael Mendoza
(74) *Attorney, Agent, or Firm* — Patterson Thuente Pedersen, P.A.

(57) ABSTRACT

A mechanical system for bilaterally securing skin tissue preferably utilizes a tissue manipulator apparatus to approximate a portion of an interior surface of each of two pieces of living dermis tissue along a vertical interface below an exterior surface without overlapping either interior surface across the vertical interface. An applicator apparatus includes a driving head portion positioned in the vertical interface and at least partially below the exterior surface and a handle portion positioned at least partially above the exterior surface. The applicator apparatus bilaterally drives at least one portion of the fastener through each piece of the living dermis tissue behind the interior surface of that piece of tissue such that the fastener is positioned below the
(Continued)

exterior surface and a portion of the fastener is positioned generally transverse to the vertical interface.

8 Claims, 51 Drawing Sheets

Related U.S. Application Data continuation of application No. 13/796,798, filed on Mar. 12, 2013, now Pat. No. 8,821,517, which is a continuation of application No. 13/314,978, filed on Dec. 8, 2011, now abandoned, which is a continuation of application No. 11/022,319, filed on Dec. 23, 2004, now Pat. No. 8,074,857, which is a continuation-in-part of application No. 10/448,838, filed on May 30, 2003, now Pat. No. 7,686,200, which is a division of application No. 10/179,628, filed on Jun. 25, 2002, now Pat. No. 6,726,705, said application No. 11/022,319 is a continuation-in-part of application No. 10/607,497, filed on Jun. 25, 2003, now Pat. No. 7,950,559, and a continuation-in-part of application No. 10/603,397, filed on Jun. 25, 2003, now Pat. No. 7,112,214.

(51) Int. Cl.
*A61B 17/28* (2006.01)
*A61B 17/30* (2006.01)
*A61B 17/00* (2006.01)
*A61B 17/08* (2006.01)

(52) U.S. Cl.
CPC .......... *A61B 17/0644* (2013.01); *A61B 17/08* (2013.01); *A61B 17/282* (2013.01); *A61B 17/30* (2013.01); *A61B 2017/00004* (2013.01); *A61B 2017/081* (2013.01)

(58) Field of Classification Search
CPC .... A61B 2017/00004; A61B 2017/081; A61B 17/30; A61B 17/282
See application file for complete search history.

(56) References Cited

U.S. PATENT DOCUMENTS

| | | | |
|---|---|---|---|
| 2,344,071 | A | 3/1944 | Wilson et al. |
| 2,351,608 | A | 6/1944 | Greenwood |
| 2,439,383 | A | 4/1948 | Erickson |
| 2,526,902 | A | 10/1950 | Rublee |
| 2,881,762 | A | 4/1959 | Lowrie |
| 2,959,172 | A | 11/1960 | Held |
| 3,074,409 | A | 1/1963 | Bielz |
| 3,082,426 | A | 3/1963 | Miles |
| 3,123,077 | A | 3/1964 | Alcamo |
| 3,297,033 | A | 1/1967 | Schmitt et al. |
| 3,344,790 | A | 10/1967 | Dorner |
| 3,570,497 | A | 3/1971 | Lemole |
| 3,601,302 | A | 8/1971 | Potekhina et al. |
| 3,636,956 | A | 1/1972 | Schneider |
| 3,638,654 | A | 2/1972 | Akuba |
| 3,643,851 | A | 2/1972 | Green et al. |
| 3,716,058 | A | 2/1973 | Tanner, Jr. |
| 3,757,629 | A | 9/1973 | Schneider |
| 3,792,010 | A | 2/1974 | Wasserman et al. |
| 3,855,688 | A | 12/1974 | Knohl |
| 3,858,783 | A | 1/1975 | Kapitanov et al. |
| 4,014,492 | A | 3/1977 | Rothfuss |
| 4,027,676 | A | 6/1977 | Mattei |
| 4,047,533 | A | 9/1977 | Perciaccante et al. |
| 4,162,678 | A | 7/1979 | Fedotov et al. |
| 4,164,225 | A | 8/1979 | Johnson et al. |
| 4,204,541 | A | 5/1980 | Kapitanov |
| 4,217,902 | A | 8/1980 | March |
| 4,259,959 | A | 4/1981 | Walker |
| 4,261,244 | A | 4/1981 | Becht et al. |
| 4,296,751 | A | 10/1981 | Blake, III et al. |
| 4,317,451 | A | 3/1982 | Cerwin et al. |
| 4,345,601 | A | 8/1982 | Fukuda |
| 4,354,628 | A | 10/1982 | Green |
| 4,396,139 | A | 8/1983 | Hall et al. |
| 4,399,810 | A | 8/1983 | Samuels et al. |
| 4,407,286 | A | 10/1983 | Noiles et al. |
| 4,410,125 | A | 10/1983 | Noiles et al. |
| D271,418 | S | 11/1983 | Campbell et al. |
| 4,428,376 | A | 1/1984 | Mericle |
| 4,430,998 | A | 2/1984 | Harvey et al. |
| 4,434,796 | A | 3/1984 | Karapetian et al. |
| 4,440,171 | A | 4/1984 | Nomoto et al. |
| 4,454,875 | A | 6/1984 | Pratt et al. |
| 4,465,071 | A | 8/1984 | Samuels et al. |
| 4,467,805 | A | 8/1984 | Fukuda |
| 4,484,580 | A | 11/1984 | Nomoto et al. |
| 4,485,816 | A | 12/1984 | Krumme |
| 4,485,953 | A | 12/1984 | Rothfuss |
| 4,493,322 | A | 1/1985 | Becht |
| 4,505,273 | A | 3/1985 | Braun et al. |
| 4,506,669 | A | 3/1985 | Blake, III |
| D278,656 | S | 4/1985 | Green et al. |
| 4,508,253 | A | 4/1985 | Green |
| 4,513,746 | A | 4/1985 | Aranyi et al. |
| 4,526,173 | A | 7/1985 | Sheehan |
| 4,526,174 | A | 7/1985 | Froehlich |
| 4,534,352 | A | 8/1985 | Korthoff |
| 4,535,772 | A | 8/1985 | Sheehan |
| 4,539,990 | A | 9/1985 | Stivala |
| 4,548,202 | A | 10/1985 | Duncan |
| 4,557,265 | A | 12/1985 | Andersson |
| 4,566,620 | A | 1/1986 | Green et al. |
| 4,568,009 | A | 2/1986 | Green |
| 4,570,623 | A | 2/1986 | Ellison et al. |
| 4,573,622 | A | 3/1986 | Green et al. |
| 4,583,670 | A | 4/1986 | Alvarado |
| 4,592,498 | A | 6/1986 | Braun et al. |
| 4,593,843 | A | 6/1986 | Saravis |
| 4,596,249 | A | 6/1986 | Freda et al. |
| 4,596,350 | A | 6/1986 | Smith et al. |
| 4,603,693 | A | 8/1986 | Conta et al. |
| 4,607,638 | A | 8/1986 | Crainich |
| 4,610,251 | A | 9/1986 | Kumar |
| 4,618,086 | A | 10/1986 | Li et al. |
| 4,619,262 | A | 10/1986 | Taylor |
| D287,630 | S | 1/1987 | Sharkany et al. |
| 4,637,380 | A | 1/1987 | Orejola |
| 4,646,741 | A | 3/1987 | Smith |
| 4,655,222 | A | 4/1987 | Florez et al. |
| 4,665,916 | A | 5/1987 | Green |
| 4,671,279 | A | 6/1987 | Hill |
| 4,676,245 | A | 6/1987 | Fukuda |
| 4,696,300 | A | 9/1987 | Anderson |
| 4,719,917 | A | 1/1988 | Barrows et al. |
| 4,724,840 | A | 2/1988 | McVay et al. |
| 4,728,020 | A | 3/1988 | Green et al. |
| 4,741,337 | A | 5/1988 | Smith et al. |
| 4,752,024 | A | 6/1988 | Green et al. |
| 4,753,636 | A | 6/1988 | Free |
| 4,762,260 | A | 8/1988 | Richards et al. |
| 4,776,506 | A | 10/1988 | Green |
| 4,789,090 | A | 12/1988 | Blake, III |
| 4,799,483 | A | 1/1989 | Kraff |
| 4,802,478 | A | 2/1989 | Powell |
| 4,809,695 | A | 3/1989 | Gwathmey et al. |
| 4,869,414 | A | 9/1989 | Green et al. |
| 4,873,976 | A | 10/1989 | Schreiber |
| 4,887,601 | A | 12/1989 | Richards |
| 4,887,756 | A | 12/1989 | Puchy |
| 4,895,148 | A | 1/1990 | Bays et al. |
| 4,899,745 | A | 2/1990 | Laboureau et al. |
| 4,915,100 | A | 4/1990 | Green |
| 4,924,866 | A | 5/1990 | Yoon |
| 4,932,960 | A | 6/1990 | Green et al. |
| 4,938,408 | A | 7/1990 | Bedi et al. |

(56) References Cited

U.S. PATENT DOCUMENTS

| | | |
|---|---|---|
| 4,955,898 A | 9/1990 | Matsutani et al. |
| 4,969,591 A | 11/1990 | Richards et al. |
| 4,976,686 A | 12/1990 | Ball et al. |
| 4,976,715 A | 12/1990 | Bays et al. |
| 4,979,954 A | 12/1990 | Gwathmey et al. |
| 4,981,149 A | 1/1991 | Yoon et al. |
| 4,994,073 A | 2/1991 | Green |
| 5,002,562 A | 3/1991 | Oberlander |
| 5,002,563 A | 3/1991 | Pyka |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,041,128 A | 8/1991 | Korthoff |
| 5,044,540 A | 9/1991 | Dulebohn |
| 5,047,047 A | 9/1991 | Yoon |
| 5,053,047 A | 10/1991 | Yoon |
| 5,058,315 A | 10/1991 | Wagner |
| 5,062,563 A | 11/1991 | Green et al. |
| 5,067,959 A | 11/1991 | Korthoff |
| 5,078,731 A | 1/1992 | Hayhurst |
| 5,080,665 A | 1/1992 | Jarrett et al. |
| 5,084,063 A | 1/1992 | Korthoff |
| 5,089,009 A | 2/1992 | Green |
| 5,089,010 A | 2/1992 | Korthoff |
| 5,089,011 A | 2/1992 | Korthoff |
| 5,104,394 A | 4/1992 | Knoepfler |
| 5,108,422 A | 4/1992 | Green et al. |
| 5,123,913 A | 6/1992 | Wilk et al. |
| 5,129,570 A | 7/1992 | Schulze et al. |
| 5,133,738 A | 7/1992 | Korthoff et al. |
| 5,139,514 A | 8/1992 | Korthoff et al. |
| 5,156,315 A | 10/1992 | Green et al. |
| 5,156,609 A | 10/1992 | Nakao et al. |
| 5,156,615 A | 10/1992 | Korthoff et al. |
| 5,158,566 A | 10/1992 | Pianetti |
| 5,158,567 A | 10/1992 | Green |
| 5,160,339 A | 11/1992 | Chen et al. |
| 5,176,306 A | 1/1993 | Heimerl et al. |
| 5,179,964 A | 1/1993 | Cook |
| 5,211,644 A | 5/1993 | VanBeek et al. |
| 5,211,722 A | 5/1993 | Wagner |
| 5,222,976 A | 6/1993 | Yoon |
| 5,226,912 A | 7/1993 | Kaplan et al. |
| 5,236,440 A | 8/1993 | Hlavacek |
| 5,242,457 A | 9/1993 | Akopov et al. |
| 5,257,713 A | 11/1993 | Green et al. |
| 5,258,009 A | 11/1993 | Conners |
| 5,258,010 A | 11/1993 | Green et al. |
| 5,258,012 A | 11/1993 | Luscombe et al. |
| 5,259,845 A | 11/1993 | Korthoff |
| 5,263,973 A | 11/1993 | Cook |
| 5,269,783 A | 12/1993 | Sander |
| 5,269,792 A | 12/1993 | Kovac et al. |
| 5,275,166 A | 1/1994 | Vaitekunas et al. |
| 5,282,807 A | 2/1994 | Knoepfler |
| 5,285,944 A | 2/1994 | Green et al. |
| 5,292,326 A | 3/1994 | Green et al. |
| 5,293,881 A | 3/1994 | Green et al. |
| 5,297,714 A | 3/1994 | Kramer |
| 5,304,204 A | 4/1994 | Bregen |
| 5,306,281 A | 4/1994 | Beurrier |
| 5,324,307 A | 6/1994 | Jarrett et al. |
| 5,330,503 A | 7/1994 | Yoon |
| 5,333,772 A | 8/1994 | Rothfuss et al. |
| 5,337,937 A | 8/1994 | Remiszewski et al. |
| 5,342,376 A | 8/1994 | Ruff |
| 5,350,400 A | 9/1994 | Esposito et al. |
| 5,356,424 A | 10/1994 | Buzerak et al. |
| 5,364,003 A | 11/1994 | Williamson, IV |
| 5,366,134 A | 11/1994 | Green et al. |
| 5,389,102 A | 2/1995 | Green et al. |
| 5,392,979 A | 2/1995 | Green et al. |
| 5,398,861 A | 3/1995 | Green |
| D357,316 S | 4/1995 | Green et al. |
| 5,413,584 A | 5/1995 | Schulze |
| 5,415,334 A | 5/1995 | Williamson, IV et al. |
| 5,417,361 A | 5/1995 | Williamson, IV |
| 5,423,856 A | 6/1995 | Green |
| 5,423,857 A | 6/1995 | Rosenman et al. |
| 5,425,489 A | 6/1995 | Shichman et al. |
| 5,425,747 A | 6/1995 | Brotz |
| 5,456,400 A | 10/1995 | Shichman et al. |
| 5,456,401 A | 10/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,489,058 A | 2/1996 | Plyley et al. |
| 5,489,287 A | 2/1996 | Green et al. |
| 5,499,990 A | 3/1996 | Schulken et al. |
| 5,505,363 A | 4/1996 | Green et al. |
| 5,509,596 A | 4/1996 | Green et al. |
| 5,514,149 A | 5/1996 | Green et al. |
| 5,542,594 A | 8/1996 | McKean et al. |
| 5,544,802 A | 8/1996 | Crainich |
| 5,549,619 A | 8/1996 | Peters et al. |
| 5,551,622 A | 9/1996 | Yoon |
| 5,558,266 A | 9/1996 | Green et al. |
| 5,562,241 A | 10/1996 | Knodel et al. |
| 5,571,285 A | 11/1996 | Chow et al. |
| 5,573,541 A | 11/1996 | Green et al. |
| 5,573,542 A | 11/1996 | Stevens |
| 5,575,800 A | 11/1996 | Gordon |
| 5,579,978 A | 12/1996 | Green et al. |
| 5,584,859 A | 12/1996 | Brotz |
| 5,591,178 A | 1/1997 | Green et al. |
| 5,593,423 A | 1/1997 | Person et al. |
| 5,618,311 A | 4/1997 | Gryskiewicz |
| 5,645,567 A | 7/1997 | Crainich |
| 5,655,698 A | 8/1997 | Yoon |
| 5,658,312 A | 8/1997 | Green et al. |
| 5,662,258 A | 9/1997 | Knodel et al. |
| 5,662,655 A | 9/1997 | Laboureau et al. |
| 5,667,527 A | 9/1997 | Cook |
| 5,706,997 A | 1/1998 | Green et al. |
| 5,722,981 A | 3/1998 | Stevens |
| 5,725,538 A | 3/1998 | Green et al. |
| 5,725,554 A | 3/1998 | Simon et al. |
| 5,728,108 A | 3/1998 | Griffiths et al. |
| 5,741,278 A | 4/1998 | Stevens |
| 5,782,844 A | 7/1998 | Yoon et al. |
| 5,792,152 A | 8/1998 | Klein et al. |
| 5,794,834 A | 8/1998 | Hamblin et al. |
| 5,816,471 A | 10/1998 | Plyley et al. |
| 5,829,662 A | 11/1998 | Allen et al. |
| 5,843,084 A | 12/1998 | Hart et al. |
| 5,871,135 A | 2/1999 | Williamson, IV et al. |
| 5,878,937 A | 3/1999 | Green et al. |
| 5,902,311 A | 5/1999 | Andreas et al. |
| 5,902,319 A | 5/1999 | Daley |
| 5,908,149 A | 6/1999 | Welch et al. |
| 5,908,427 A | 6/1999 | McKean et al. |
| 5,921,994 A | 7/1999 | Andreas et al. |
| 5,947,999 A | 9/1999 | Groiso |
| 5,964,774 A | 10/1999 | McKean et al. |
| 5,976,160 A | 11/1999 | Crainich |
| 5,984,949 A | 11/1999 | Levin |
| 5,993,476 A | 11/1999 | Groiso |
| 6,036,699 A | 3/2000 | Andreas et al. |
| 6,036,701 A | 3/2000 | Rosenman |
| 6,039,753 A | 3/2000 | Meislin |
| 6,045,560 A | 4/2000 | McKean et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,136,010 A | 10/2000 | Modesitt et al. |
| 6,149,658 A | 11/2000 | Gardiner et al. |
| 6,159,224 A | 12/2000 | Yoon |
| 6,241,747 B1 | 6/2001 | Ruff |
| 6,250,532 B1 | 6/2001 | Green et al. |
| 6,270,517 B1 | 8/2001 | Brotz |
| 6,325,805 B1 | 12/2001 | Ogilvie et al. |

(56) References Cited

U.S. PATENT DOCUMENTS

| | | | |
|---|---|---|---|
| 6,387,104 B1 | 5/2002 | Pugsley et al. | |
| 6,387,113 B1 | 5/2002 | Hawkins et al. | |
| 6,409,743 B1 | 6/2002 | Fenton, Jr. | |
| 6,423,088 B1 | 7/2002 | Fenton, Jr. | |
| 6,443,962 B1 | 9/2002 | Gaber | |
| 6,514,263 B1 | 2/2003 | Stefanchik et al. | |
| 6,530,933 B1 | 3/2003 | Yeung et al. | |
| 6,599,310 B2 | 7/2003 | Leung et al. | |
| 6,601,748 B1 * | 8/2003 | Fung | A61B 17/0684 227/176.1 |
| 6,619,529 B2 | 9/2003 | Green et al. | |
| 6,626,916 B1 | 9/2003 | Yeung et al. | |
| 6,629,988 B2 | 10/2003 | Weadock | |
| 6,638,297 B1 | 10/2003 | Huitema | |
| 6,652,538 B2 | 11/2003 | Kayan et al. | |
| 6,666,872 B2 | 12/2003 | Barreiro et al. | |
| 6,692,499 B2 | 2/2004 | Törmälä et al. | |
| 6,726,705 B2 | 4/2004 | Peterson et al. | |
| 6,767,356 B2 | 7/2004 | Kanner et al. | |
| 6,773,437 B2 | 8/2004 | Ogilvie et al. | |
| 7,112,214 B2 | 9/2006 | Peterson et al. | |
| D532,107 S | 11/2006 | Peterson et al. | |
| 7,547,315 B2 | 6/2009 | Peterson et al. | |
| 7,682,372 B2 | 3/2010 | Peterson | |
| 7,686,200 B2 | 3/2010 | Peterson | |
| D635,259 S | 3/2011 | Peterson et al. | |
| 7,950,559 B2 | 5/2011 | Peterson et al. | |
| 8,066,736 B2 | 11/2011 | Peterson et al. | |
| 8,074,857 B2 | 12/2011 | Peterson et al. | |
| 8,100,939 B2 | 1/2012 | Peterson | |
| 8,506,591 B2 | 8/2013 | Danielson et al. | |
| D752,219 S | 3/2016 | Peterson et al. | |
| 2002/0007184 A1 | 1/2002 | Ogilvie et al. | |
| 2002/0019636 A1 | 2/2002 | Ogilvie et al. | |
| 2002/0133181 A1 | 9/2002 | Tong | |
| 2003/0028218 A1 | 2/2003 | Bauer | |
| 2003/0139746 A1 | 7/2003 | Groiso | |
| 2003/0233108 A1 | 12/2003 | Gellman et al. | |
| 2003/0236550 A1 | 12/2003 | Peterson | |
| 2003/0236551 A1 | 12/2003 | Peterson | |
| 2004/0059377 A1 | 3/2004 | Peterson et al. | |
| 2004/0059378 A1 | 3/2004 | Peterson et al. | |
| 2005/0033317 A1 | 2/2005 | Ables | |
| 2005/0085857 A1 | 4/2005 | Peterson et al. | |
| 2005/0149064 A1 | 7/2005 | Peterson et al. | |
| 2005/0182444 A1 | 8/2005 | Peterson et al. | |
| 2006/0135988 A1 | 6/2006 | Peterson | |
| 2007/0185504 A1 | 8/2007 | Manetakis et al. | |
| 2009/0093824 A1 | 4/2009 | Hasan et al. | |
| 2012/0083831 A1 | 4/2012 | Peterson | |
| 2012/0145765 A1 | 6/2012 | Peterson et al. | |
| 2013/0267997 A1 | 10/2013 | Peterson et al. | |
| 2015/0112369 A1 | 4/2015 | Peterson et al. | |
| 2015/0127046 A1 | 5/2015 | Peterson | |
| 2015/0133966 A1 | 5/2015 | Gupta et al. | |
| 2015/0305740 A1 | 10/2015 | Peterson et al. | |
| 2016/0242772 A1 | 8/2016 | Peterson et al. | |
| 2017/0071602 A1 | 3/2017 | Peterson et al. | |

FOREIGN PATENT DOCUMENTS

| | | |
|---|---|---|
| FR | 2549544 | 1/1985 |
| JP | 04-226642 A | 8/1992 |
| JP | 5-504892 | 7/1993 |
| JP | 06233772 | 8/1994 |
| JP | 7-124166 | 5/1995 |
| JP | 2000-217829 | 8/2000 |
| JP | 2000-517197 | 12/2000 |
| WO | WO 97/18761 | 5/1997 |
| WO | WO 00/57796 | 10/2000 |
| WO | WO 00/67644 | 11/2000 |

OTHER PUBLICATIONS

Application and File history for U.S. Appl. No. 15/145,194, filed May 3, 2015. Inventors: Peterson et al.
Application and File history for U.S. Appl. No. 29/513,614, filed Jan. 2, 2015. Inventors: Peterson et al.
Application and File history for U.S. Appl. No. 11/487,951, filed Jul. 17, 2006. Inventor: Peterson et al.
Application and File history for U.S. Appl. No. 13/324,680, filed Dec. 13, 2011. Inventor: Peterson et al.
Application and File history for U.S. Appl. No. 11/316,322, filed Dec. 22, 2005. Inventor: Peterson.
Office Action dated Sep. 27, 2016 for EP Application No. 03761338.7, 5 pages.
PCT Search Report and Written Opinion dated Jul. 1, 2015 for PCT Application No. PCT/US2015/025130, 13 pages.
Suturtek Incorporated, http://www.suturtek.com/productInfo/, Jan. 31, 2007, p. 1 of 1, North Chelmsford, Massachusetts.
Brochure: *Information Booklet for Auto Suture® Purse String Instrument*, Auto Suture Company, a division of United States Surgical Corporation, Norwalk, CT, 2 pgs., 1978.
Brochure: *La Sutura Perde it Filo*, Farmitalia Carlo Erba, 4 pgs., not dated.
*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-226, 1994.
File history for U.S. Appl. No. 10/448,838, filed May 30, 2003. Inventors: James Peterson.
File history for U.S. Appl. No. 10/607,497, filed Jun. 25, 2003. Inventors: James Peterson et al.
File history for U.S. Appl. No. 10/603,397, filed Jun. 25, 2003. Inventors: James Peterson et al.
File history for U.S. Appl. No. 11/022,319, filed Dec. 23, 2004. Inventors: James Peterson et al.
File history for U.S. Appl. No. 11/003,145, filed Dec. 3, 2004. Inventors: James Peterson et al.
File history for U.S. Appl. No. 11/097,085, filed Apr. 1, 2005. Inventors: James Peterson et al.
File history for U.S. Appl. No. 13/314,978, filed Dec. 8, 2011. Inventors: James Peterson et al.
EPO Communication dated Mar. 8, 2011 for EP Application No. 03761338.7 filed Jun. 25, 2003, 6 pages.
EP Communication dated Jan. 23, 2015 for EP Application No. 03761338.7 filed Jun. 25, 2003, 4 pages.
PCT Search Report dated Oct. 13, 2004 for PCT Application No. PCT/US03/20083 filed Jun. 25, 2003, 5 pages.
File history for U.S. Appl. No. 13/796,798, filed Mar. 12, 2013. Inventors: James Peterson et al.
File history for U.S. Appl. No. 14/471,519, filed Aug. 28, 2014, 2013. Inventors: James Peterson et al.
Application and File history for U.S. Appl. No. 14/555,004, filed Nov. 26, 2014. Inventor: Peterson.
Petition for Inter Partes Review of U.S. Pat. No. 8,821,517 filed May 15, 2017, 80 pages.
Exhibit 1001 to Petition for Inter Partes Review of U.S. Pat. No. 8,821,517 filed May 15, 2017, 67 pages.
Exhibit 1002 to Petition for Inter Partes Review of U.S. Pat. No. 8,821,517 filed May 15, 2017, 22 pages.
Exhibit 1003 to Petition for Inter Partes Review of U.S. Pat. No. 8,821,517 filed May 15, 2017, 30 pages.
Exhibit 1004 to Petition for Inter Partes Review of U.S. Pat. No. 8,821,517 filed May 15, 2017, 5 pages.
Exhibit 1005 to Petition for Inter Partes Review of U.S. Pat. No. 8,821,517 filed May 15, 2017, 26 pages.
Exhibit 1006 to Petition for Inter Partes Review of U.S. Pat. No. 8,821,517 filed May 15, 2017, 12 pages.
Exhibit 1007A to Petition for Inter Partes Review of U.S. Pat. No. 8,821,517 filed May 15, 2017, 2 pages.
Exhibit 1007B to Petition for Inter Partes Review of U.S. Pat. No. 8,821,517 filed May 15, 2017, 2pages.
Exhibit 1008 to Petition for Inter Partes Review of U.S. Pat. No. 8,821,517 filed May 15, 2017, 25 pages.

(56) References Cited

OTHER PUBLICATIONS

Exhibit 1009 to Petition for Inter Partes Review of U.S. Pat. No. 8,821,517 filed May 15, 2017, 2 pages.
Exhibit 1010 to Petition for Inter Partes Review of U.S. Pat. No. 8,821,517 filed May 15, 2017, 2 pages.
Exhibit 1011 to Petition for Inter Partes Review of U.S. Pat. No. 8,821,517 filed May 15, 2017, 2 pages.
Exhibit 1012 to Petition for Inter Partes Review of U.S. Pat. No. 8,821,517 filed May 15, 2017, 60 pages.
Exhibit 1013 to Petition for Inter Partes Review of U.S. Pat. No. 8,821,517 filed May 15, 2017, 9 pages.
Exhibit 1014 to Petition for Inter Partes Review of U.S. Pat. No. 8,821,517 filed May 15, 2017, 7 pages.
Exhibit 1015 to Petition for Inter Partes Review of U.S. Pat. No. 8,821,517 filed May 15, 2017, 11 pages.
Exhibit 1016 to Petition for Inter Partes Review of U.S. Pat. No. 8,821,517 filed May 15, 2017, 5 pages.
Exhibit 1017 to Petition for Inter Partes Review of U.S. Pat. No. 8,821,517 filed May 15, 2017, 19 pages.
Exhibit 1018 to Petition for Inter Partes Review of U.S. Pat. No. 8,821,517 filed May 15, 2017, 11 pages.
Application and File history for U.S. Appl. No. 14/851,308, filed Sep. 11, 2015. Inventors: Peterson et al.

\* cited by examiner

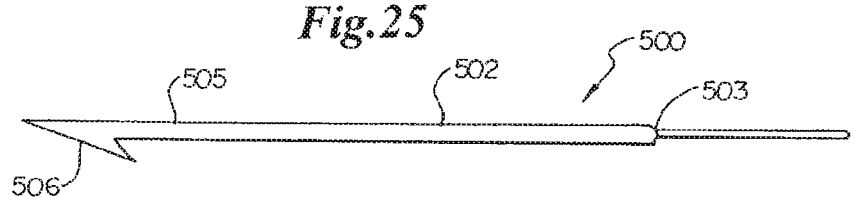
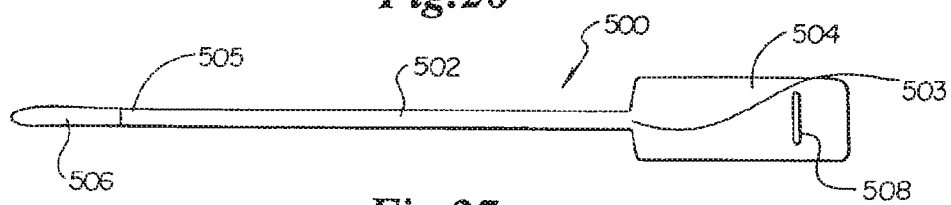
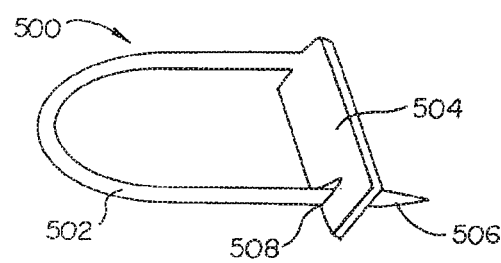
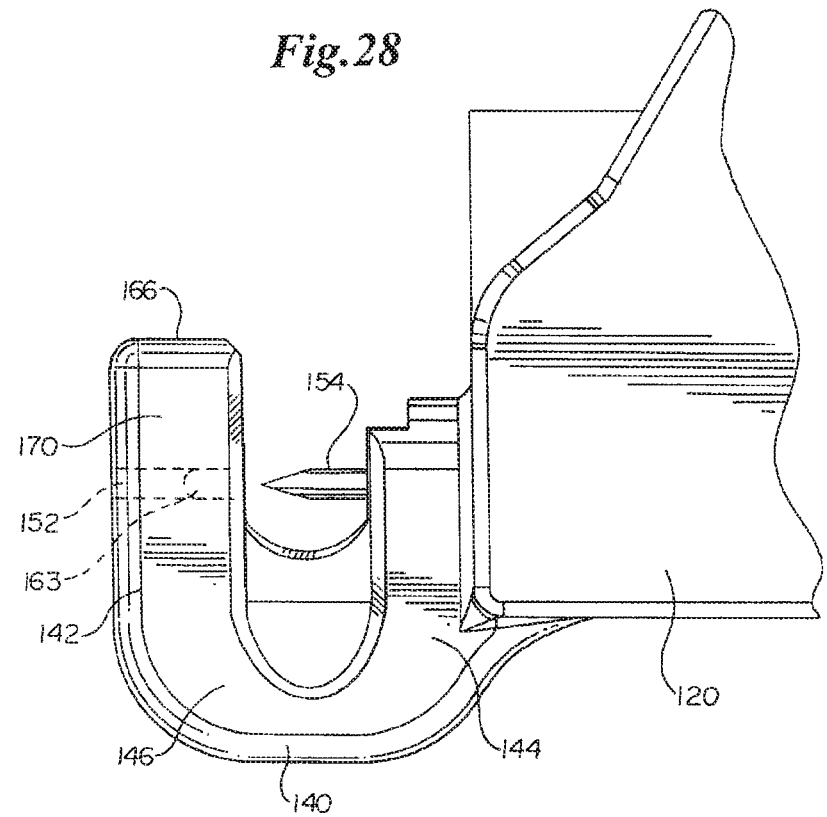

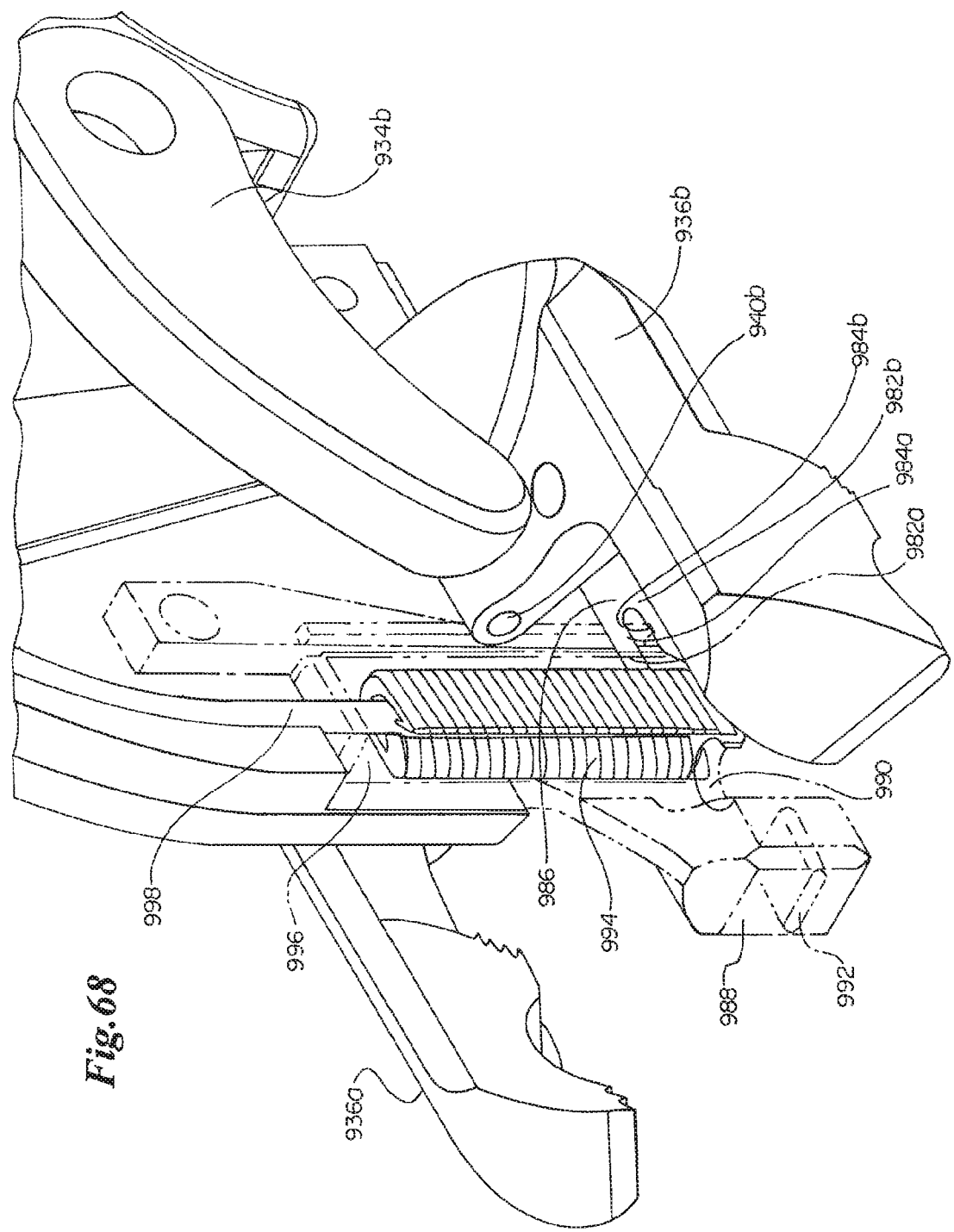

MECHANICAL METHOD AND APPARATUS FOR BILATERAL TISSUE FASTENING

PRIORITY CLAIM AND RELATED APPLICATIONS

This application is a continuation of U.S. patent application Ser. No. 14/471,519, filed Aug. 28, 2014, which in turn is a continuation of U.S. patent application Ser. No. 13/796, 798, filed Mar. 12, 2013 (now U.S. Pat. No. 8,821,517 issued Sep. 2, 2014), which in turn is a continuation of U.S. patent application Ser. No. 13/314,978, filed Dec. 8, 2011 (now abandoned), which in turn is a continuation of U.S. patent application Ser. No. 11/022,319, filed Dec. 23, 2004 (now U.S. Pat. No. 8,074,857 issued Dec. 13, 2011), which in turn is a continuation-in-part of U.S. patent application Ser. No. 10/448,838, filed May 30, 2003 (now U.S. Pat. No. 7,686, 200 issued Mar. 30, 2010), which is a divisional of U.S. patent application Ser. No. 10/179,628, filed Jun. 25, 2002 (now U.S. Pat. No. 6,726,705 issued Apr. 27, 2004), and U.S. patent application Ser. No. 11/022,319 is also a continuation-in-part of U.S. patent application Ser. No. 10/607, 497, filed Jun. 25, 2003 (now U.S. Pat. No. 7,950,559 issued May 31, 2011), and U.S. patent application Ser. No. 11/022, 319 is also a continuation-in-part of U.S. patent application Ser. No. 10/603,397, filed Jun. 25, 2003 (now U.S. Pat. No. 7,112,214 issued Sep. 26, 2006), all of which are herein incorporated by reference in their entirety.

FIELD OF THE INVENTION

The present invention relates generally to the field of surgical instruments such as surgical staplers, clip applicators and sutureless closure devices. More particularly, the present invention relates to a mechanical method and apparatus for fastening tissue, such as skin tissue, with a fastener positioned below the tissue surface that bilaterally secures opposed pieces of tissue.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening in close proximity so as to promote the healing process.

In the case of skin tissue, for example, healing occurs best when the opposing dermal layers of the skin tissue are held in proximity with each other. Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue.

The most prevalent method for forcibly closing a tissue opening is through the use of a suture or "stitches." As early as the second century, the Greeks were using sutures to physically close skin openings. In its simplest form, a suture is simply a length of material that is attached to a tissue-piercing device, such as a needle, and looped through the opposing sides of an opening. The suture is then pulled tight and the loop closes causing the opposing sides of the tissue to come into close physical proximity. The suture loop is held tight by the tying of a knot or some other locking mechanism. The first sutures were made of animal gut. Eventually other natural suture materials including leather, horsehair, flax, cotton and silk came into use.

As the sciences of medical and materials technology have advanced over the course of the past century, new bioabsorbable materials have been developed to further improve upon the basic suturing concept. Examples of modern improvements to the suturing process include enhancements to the suturing apparatus as shown, for example, in U.S. Pat. Nos. 2,439,383, 2,959,172 and 3,344,790, as well as advances in sutures and suture materials as shown, for example, in U.S. Pat. Nos. 3,123,077, 3,297,033, 3,636,956, 3,792,010 4,027,676 and 4,047,533.

While traditional suturing remains a popular method of effectuating closure of skin openings, the use of staples and staplers as a skin closure technique has become increasingly popular, especially in surgical settings where the opening is created through a purposeful incision. In these settings, the incision tends to make a clean, straight cut with the opposing sides of the incision having consistent and non-jagged surfaces. Typically, stapling of a skin opening, for example, is accomplished by manually approximating the opposing sides of the skin opening and then positioning the stapler so that a staple will span the opening. The stapler is then manipulated such that the staple is driven into the skin with one leg being driven into each side of the skin and the cross-member of the staple extending across the opening external to the skin surface. Generally, the legs of the staple are driven into an anvil causing the staple to deform so as to retain the skin tissue in a compressed manner within the staple. This process can be repeated along the length of the opening such that the entire incision is held closed during the healing process.

Much work has been devoted to improving upon the basic stapling process. Developments have gone in a variety of directions and include work devoted to the stapling apparatus as shown, for example, in U.S. Pat. Nos. 3,082,426, 3,643,851, 4,410,125, 4,493,322, 4,592,498, 4,618,086, 4,776,506, 4,915,100, 5,044,540, 5,129,570, 5,285,944, 5,392,979, 5,489,058, 5,551,622, 5,662,258, 5,794,834, 5,816,471, 6,131,789 and 6,250,532. In addition to the stapling apparatus, developments have also been made in the staple design as shown, for example, in U.S. Pat. Nos. 2,351,608, 2,526,902, 2,881,762, 3,757,629, 4,014,492, 4,261,244, 4,317,451, 4,407,286, 4,428,376, 4,485,816, 4,505,273, 4,526,174, 4,570,623, 4,719,917, 4,741,337, 5,007,921, 5,158,567, 5,258,009, 5,297,714, 5,324,307, 5,413,584, 5,505,363 and 5,571,285.

While modern suturing and stapling techniques continue to provide an effective manner of effectuating skin closure, there remains a series of inherent disadvantages in using either of these techniques. The standard technique for both suturing and stapling includes puncturing both the epidermis and dermis. This can result in a wound closure having an unaesthetically pleasing appearance on the surface of the skin. The presence of the fastener exposed through the skin surface provides an opportunity for infection and for accidentally catching the fastener and tearing the wound open. In the case of non-absorbable fasteners, further action by a medical professional is necessary in order to remove the fastener once biological healing is complete.

In order to overcome these limitations, practitioners have developed a number of specialized suturing techniques where the suture is passed only through the dermis effectively positioning the suture below the skin surface, or in a subcuticular fashion. A surgeon has the choice of placing individual or interrupted sutures along the length of an opening. Another suturing option is for the surgeon to use a single strand of suture material to place a plurality of continuing suture loops or running sutures along the length of an opening. While the presence of the suture below the surface can improve the aesthetic nature of the closure, it requires greater skill and technique to accomplish effectively and takes longer than conventional external suturing.

While there has been active development of dermal layer suturing techniques, little has been done in the area of staples and staplers for use in connection with the dermal layer. In a series of patents issued to Green et al., including U.S. Pat. Nos. 5,292,326, 5,389,102, 5,489,287 and 5,573,541, a subcuticular stapling method and apparatus are disclosed that were ultimately commercialized as the U.S. Surgical SQS Subcuticular Stapling Apparatus. The Green et al. patents describe a stapling technique employing a hand-held apparatus with jaws to proximate, interdigitate and overlap opposing sides of dermal layer tissue along the length of a skin opening. The apparatus then drives a single spike through the interdigitated and overlapped dermal layers of the opposing skin surfaces in order to secure both sides of the dermal tissue on the single spike. Although this technique reduced the time required to effectuate a subcuticular skin closure, the SQS device was not commercially successful in part because the resulting closure produced an undesirable wave-like scar that sometimes did not heal effectively.

While many improvements have been made to mechanical tissue closure techniques, it would be desirable to provide a mechanical tissue closure system that is capable of effectively delivering fasteners below the skin surface so as to produce an efficient and efficacious tissue closure.

SUMMARY OF THE INVENTION

The present invention is a mechanical system for bilaterally securing skin tissue. Preferably, a tissue manipulator is used to approximate a portion of an interior surface of each of two pieces of living dermis tissue along a vertical interface below an exterior surface without overlapping either interior surface across the vertical interface. An applicator apparatus includes a driving head portion positioned in the vertical interface and at least partially below the exterior surface, and a handle portion positioned at least partially above the exterior surface. The applicator apparatus bilaterally drives at least one portion of the fastener through each piece of the living dermis tissue behind the interior surface of that piece of tissue such that the fastener is positioned below the exterior surface and a portion of the fastener is positioned generally transverse to the vertical interface.

Unlike existing mechanical tissue fastening systems, the present invention recognizes the need for and advantages of a fastener system that captures and retains dermal tissue in a compressed state within a preferably bioabsorbable fastener that is not inserted through the epidermal skin layer. The mechanical fastening system of the present invention is able to consistently and repeatedly interface a fastener with a target tissue zone in the dermal layer such that the fastener inserted into the target tissue zone produces an effective and aesthetically pleasing closure of a tissue opening.

BRIEF DESCRIPTION OF THE DRAWINGS

FIG. 25 is a top plan view of an alternative embodiment of a fastener according to the present invention.

FIG. 26 is a side elevation view of the fastener of FIG. 25.

FIG. 27 is a view of the fastener of FIG. 25 in a deployed condition.

FIG. 28 is a view of an applicator assembly according to an alternative embodiment of the invention.

FIG. 68 is a perspective, partial section view of the handheld multi-shot surgical instrument of FIG. 64.

DETAILED DESCRIPTION OF THE PREFERRED EMBODIMENTS

Figure 1:
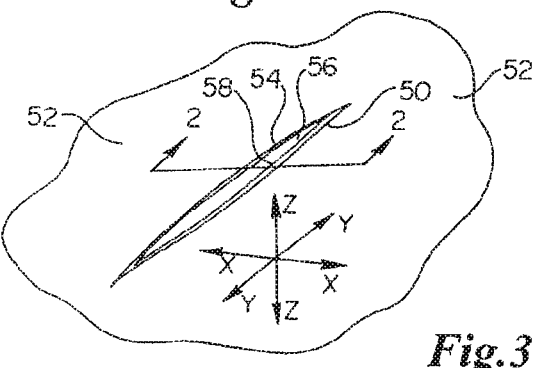
FIG. 1 shows a typical opening in skin tissue such as may be closed by the present invention.
Figure 2:
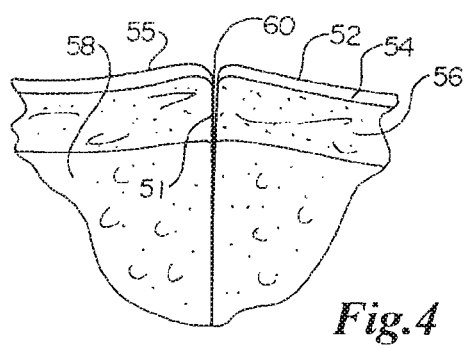
FIG. 2 shows a cross-sectional view of the skin tissue and opening of FIG. 1.
Figure 3:
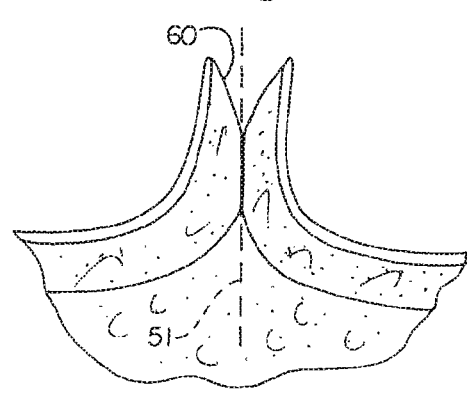
FIG. 3 shows a cross-sectional view of everted skin tissue.

In FIGS. 1-3 there is shown a depiction of a typical opening 50 in the surface of skin 52, such as may be made, for example, by a surgical incision or a wound. As illustrated in FIG. 1, for purposes of describing the present invention, opening 50 may be described as having a length or longitudinal orientation parallel to the y-y axis, a width orientation parallel to the x-x axis, and a depth orientation parallel to the z-z axis. The x-y-z axis for purposes of the present invention is defined with respect to an external tissue surface, which in the case of skin 52 is the outer surface. References to a vertical and horizontal planar orientation in connection with the present invention are made with respect to the external tissue surface at the site of the opening in question. The vertical inner surfaces 60 formed by each side of the opening 50 can be visualized as meeting along a generally vertical interface 51. It will be understood that in the case of an opening that extends over a curved tissue surface, the corresponding horizontal and vertical surfaces associated with the opening will be defined with respect to such curved tissue surface. It also will be understood that the vertical interface 51 may be vertical in only one orientation with respect to the tissue surface, such as in the case when an angled incision has formed the opening 50.

As is best illustrated in the sectional views of FIGS. 2 and 3, human skin 52 generally has three discrete layers. These layers comprise an epidermal layer 54 of mostly non-living tissue having an exterior surface 55, a dermal layer 56 of mostly living tissue, and a subcutaneous tissue layer 58. Although the preferred embodiment of the present invention will be described with respect to human skin tissue 52, it will be understood that the present invention is applicable to closure of openings in other types of tissue having generally defined surfaces, such as fascia, membranes organs, vessels, vasculature, vascular pedicles, skin grafts, bladder and other biocompatible materials with generally defined surfaces such as artificial skin, artificial membranes and synthetic mesh.

It has long been known that the most rapid healing of a skin opening with a minimum of scarring occurs when the inner surfaces 60 of the living dermal layer 56 at each side of the vertical interface 51 of skin opening 50 are brought together and held in close contact in what is referred to as an everted position as is shown in exaggerated fashion in FIG. 3. To the extent that the primarily non-living material of epidermal layer 54 can be excluded from the healing opening, the rapidity and level of scar tissue formed during the healing process will be improved.

Figure 30:
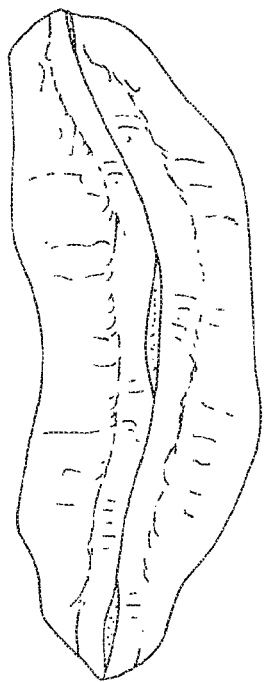
FIG. 30 is a pictorial representation of a skin opening closed with conventional subcutaneous sutures.
Figure 31:
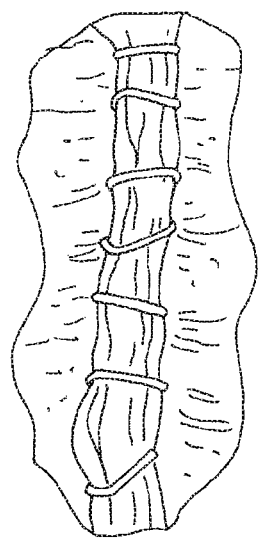
FIG. 31 is a pictorial representation of a skin opening closed by conventional surgical stapling.
Figure 32:
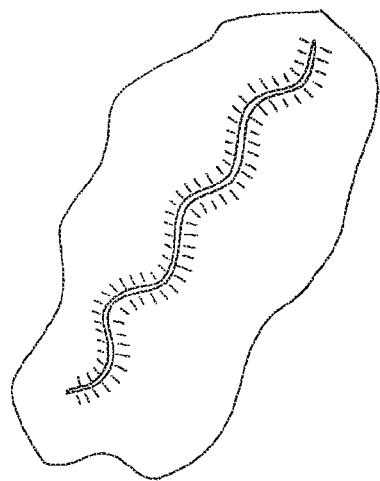
FIG. 32 is a pictorial representation of an opening closed with the prior art interdigitated subcuticular stapler.

The ability of the present invention to provide a more effective and efficacious tissue closure can be seen with reference to FIGS. 30-33, which show skin openings closed by various prior art methods as compared with an opening closed using the bilateral fastening techniques of the present invention. In FIG. 30, there is shown a skin opening closed with subcutaneous sutures. The generally everted condition of the closed opening can produce unattractive scarring and less than optimal healing if the eversion is excessive or inadequate. As can be seen from FIG. 30, obtaining consistency from suture to suture is difficult and the quality of the closure is highly dependent upon the skill of the surgeon. FIG. 31 shows a skin opening closed by conventional surgical stapling. In addition to the generally unattractive appearance of the closed opening, staple openings and the excessive everted condition of the opening may lead to undesirable scarring. In addition, if non-resorbable staples are used, the staples must be removed before complete healing can occur. FIG. 32 shows a depiction of an opening closed with the interdigitated subcuticular stapler known as the SQS device that is described, for example, in U.S. Pat. Nos. 5,292,326, 5,389,102, 5,489,287 and 5,573,541. The characteristic undulating appearance caused by the overlapping interdigitation of the skin may lead to an unusual appearing scar in the healed opening. The overlapping and interdigitation of the skin can also cause epidermis tissue to be interposed between dermal layers, thereby leading to incomplete healing or excessive scarring.

Figure 33:
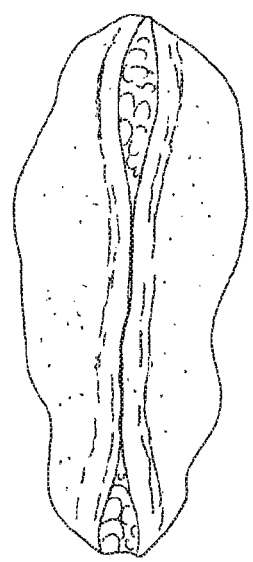
FIG. 33 is a pictorial representation of an opening closed using the bilateral fastening technique of the present invention.

By comparison, an opening that has been partially closed by the method and using the apparatus of the present invention is shown in FIG. 33. As shown, the closed portion of the opening is tightly closed, yet lies flat without undue eversion of the opening leading to better healing performance with minimal scarring. There is consistency in the closure from fastener to fastener. Because the fasteners are positioned below the skin surface (i.e., subcuticular), the fasteners are not exposed and there is no puncturing or button holing of the epidermis that can lead to the increased possibility of infection or interference with the normal healing process. In addition, if fasteners made of a bioresorbable, bioabsorbable or even a bioerodible material are used, there is no need to later remove the fasteners.

The advantages of the present invention are accomplished by an apparatus and method that bilaterally engages target tissue zones 70 on each side of a skin opening 50 with a fastener that is preferably made of a bioresorbable material. As used in connection with the present invention, the term bilateral refers to at least two axis of insertion for a fastener that are on separate sides of the vertical interface 51 of an opening 50. The bilateral engagement may be made either simultaneously or sequentially, and the fastener used may have a variety of configurations and be oriented in a variety of ways as will be further described herein. The location, geometry and orientation of the fastener and the dermal layers in relation to the mechanical apparatus of the present invention are all important considerations to obtaining the most optimal contact and compression of the dermal layer for efficacious closing of the opening. While the skin opening 50 will be described in connection with an opening in a single piece of tissue, it will be understood that the opening 50 could also be between two separate and otherwise unconnected pieces of tissue, or even between a piece of tissue and a piece of biocompatible material to be secured to that piece of tissue.

Figure 4:
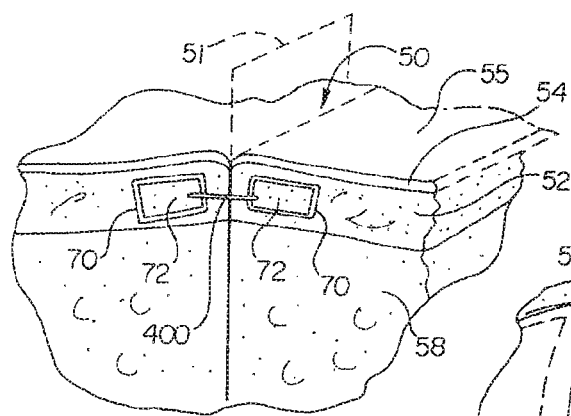
FIG. 4 shows a perspective cross-sectional view of an opening in skin tissue at rest, indicating optimal bilateral target tissue zones.
Figure 5:
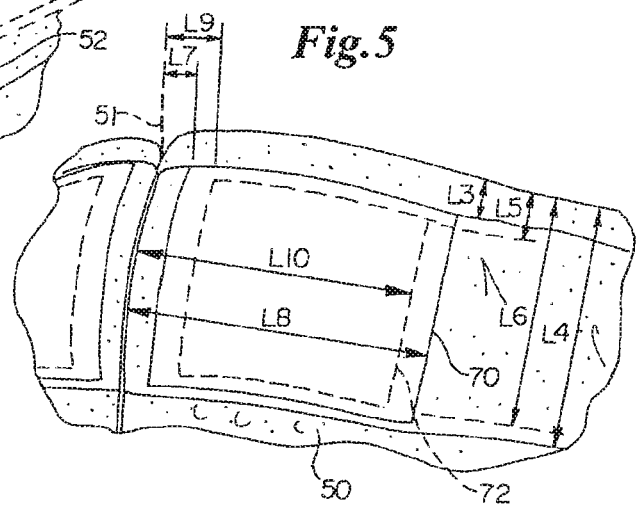
FIG. 5 shows an enlarged view of a target tissue zone.

As shown in FIGS. 4 and 5, there exists an optimal target tissue zone 70 on each side of vertical interface 51 that may be bilaterally engaged by a fastener in order to achieve optimal dermal contact for healing. This target tissue zone 70 lies within the dermal layer 56, and can be visualized as a rectangular cross-sectional area when the tissue is in a relaxed condition as shown best in FIG. 4. In addition, within target tissue zone 70, there exists a most preferred area 72 for tissue engagement. In the depth orientation, target tissue zone 70 lays between a distance L3 of about 0.1 mm below the surface 55 of epidermal layer 54, and a distance L4 up to 2.0 mm below the surface 55. The most preferred area 72 lies between a distance L5 of about 0.2 mm and a distance L6 of about 0.8 mm below the surface. In the width orientation, target tissue zone 70 lies between a distance L7 of about 1.0 mm and a distance L8 of about 20.0 mm from vertical interface 51. Most preferred area 72 lies between a distance L9 of about 2.0 mm and a distance L10 of about 8.0 mm from vertical interface 51. Because the target tissue zone 70 is not visible to an operator, the manipulator assembly 400 and applicator assembly 100 are preferably designed to consistently and repeatedly enable the operator to position the target tissue zone 70 for deployment of a fastener 400.

Figure 6:
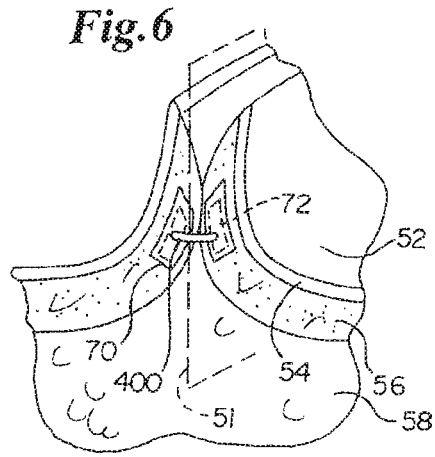
FIG. 6 shows the view of FIG. 4 with the skin tissue everted.
Figure 7:
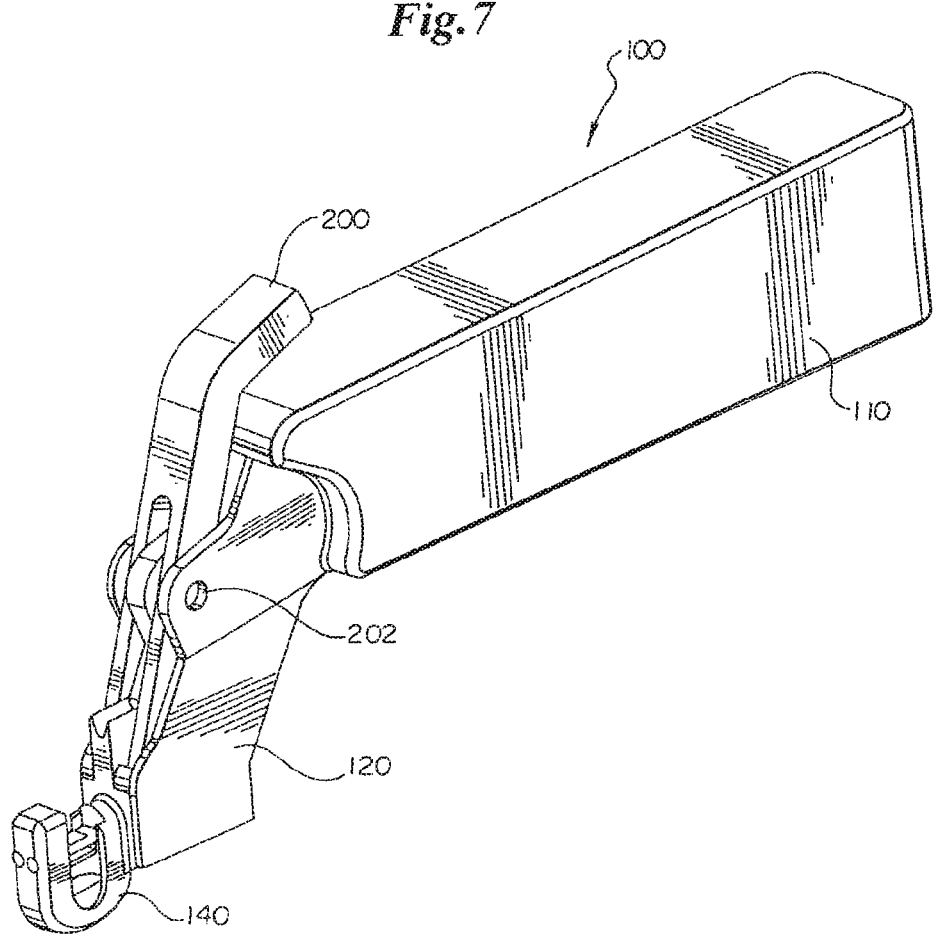
FIG. 7 is a perspective view of an embodiment of the applicator apparatus of the present invention.
Figure 8:
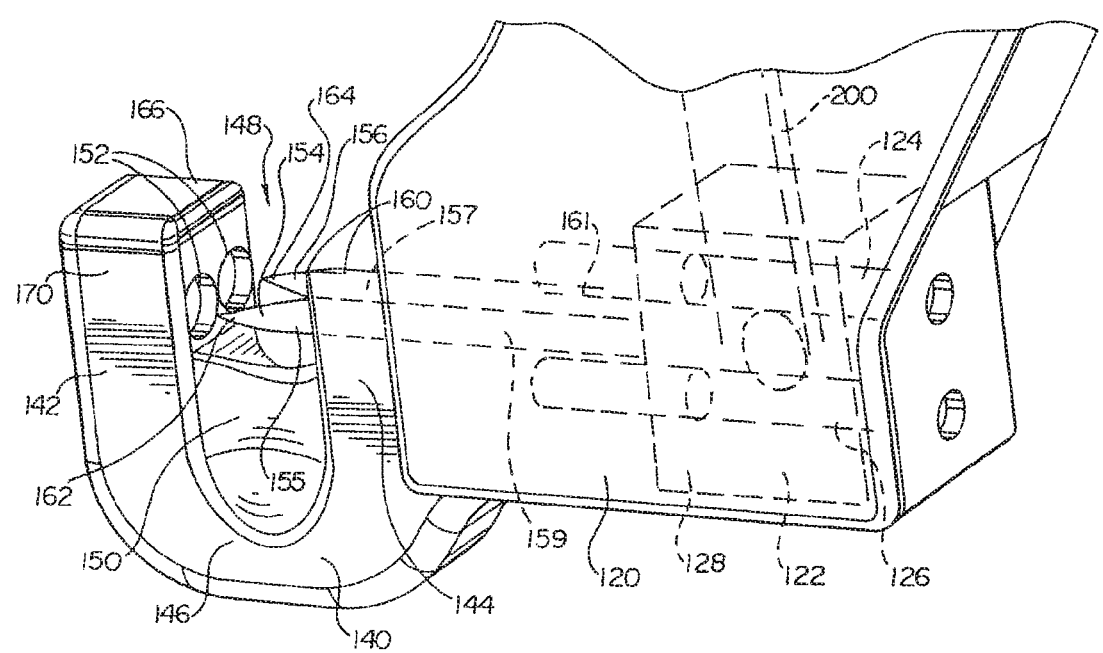
FIG. 8 is a perspective view of the lower handle and driving head portions of the applicator apparatus of FIG. 7.
Figure 9:
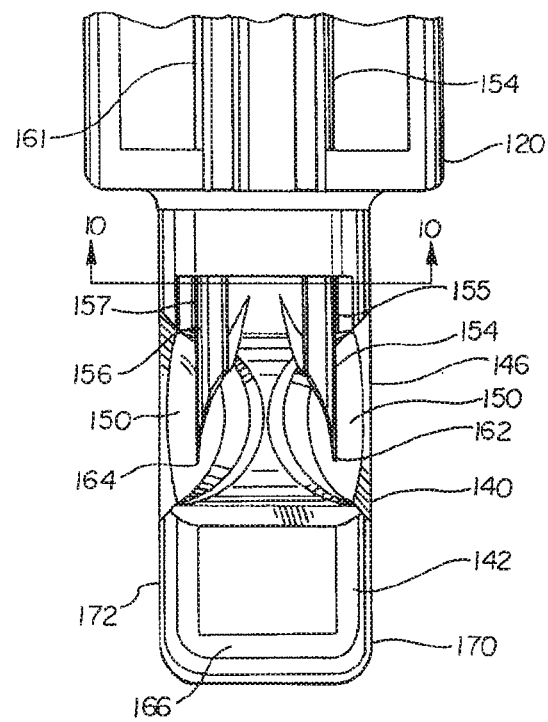
FIG. 9 is a top plan view of the lower handle and driving head portions of the applicator apparatus of FIG. 7.
Figure 10:
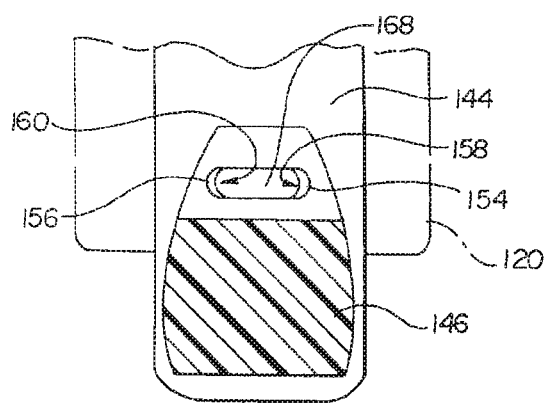
FIG. 10 is a partial cross-sectional view of the driving head portion shown in FIG. 9.
Figure 11:
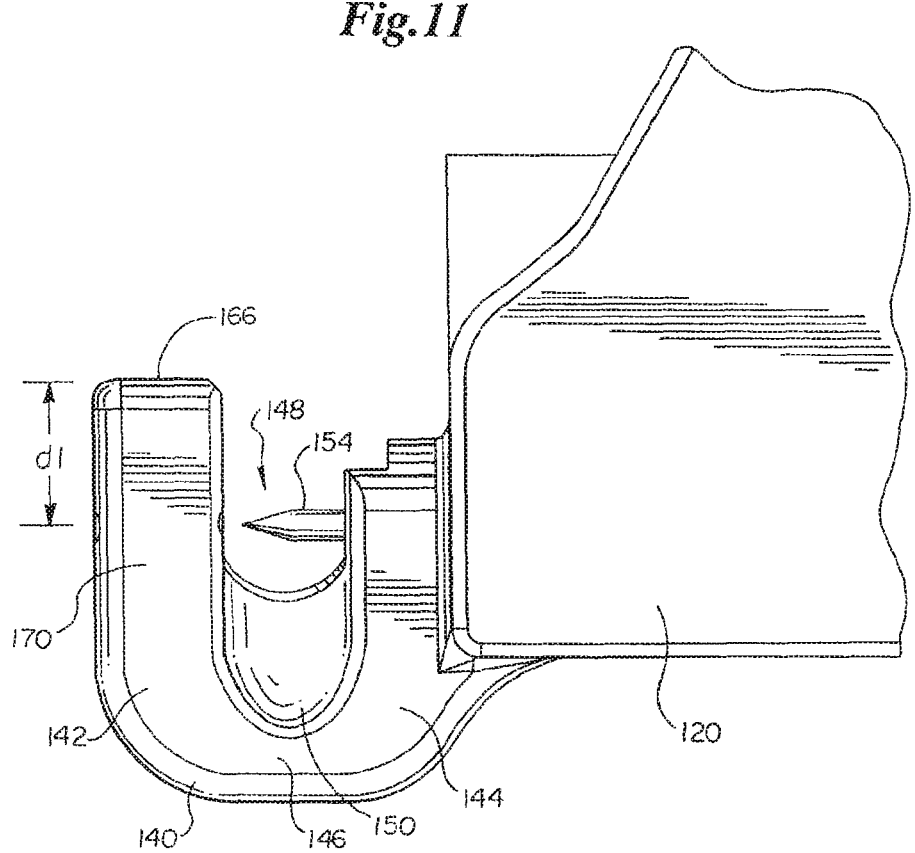
FIG. 11 is a side elevation view of the lower handle and driving head portions of the applicator apparatus of FIG. 7.

As illustrated in FIG. 6, due to the inherent flexibility and resilience of skin tissue, it is most desirable that a fastener 400 be deployed into the target tissue zone 70 while the skin opening is everted. By compressing the everted dermal layers 56 on either side of the opening 50 into the fastener 400, the dermal layers 56 are retained in close contact with each other by the fastener 400 after the everting pressure is removed and the skin relaxes into a flat condition as shown in FIG. 4.

An embodiment of the apparatus of the present invention is shown in FIGS. 7-20. Generally, the apparatus includes an applicator assembly 100, a tissue manipulator assembly 300, and a fastener 400.

An embodiment of applicator assembly 100 is shown in FIGS. 7-16. The assembly generally comprises upper handle portion 110 and lower handle portion 120, to which is attached driving head 140. Trigger 200, which pivots about pivot 202 is provided to allow user actuation of the mechanism. Although a manual pivoting trigger arrangement 200 is shown, it will be understood that a variety of other user-actuated manual triggers, buttons or actuator mechanisms may be utilized with the applicator assembly 100, such as a push button, slide mechanism, cam mechanism, spring actuated apparatus, cable actuated pull mechanism, rotating mechanism or tab actuated trigger. Alternatively, an automatic actuator in the form of an electronic, pneumatic, motion controlled, remote controlled or computer-activated trigger may be used to operate the applicator 100.

In FIGS. 8-13, there are shown detailed views of an embodiment of a driving head 140 and lower handle portion 120. Driving head 140 is preferably U-shaped and has an anvil portion 142 separated from backing portion 144 by a cross-member 146, thereby forming a gap 148. Cross-member 146 preferably has concave areas 150, which are shaped to correspond to tissue manipulator surfaces 318 of tissue manipulator assembly 300, allowing the dermal layer 56 of skin to be compressed into contact within gap 148, and with target tissue zones 70 present for capture on either side of vertical interface 51 as will be further explained hereinbelow. Although driving head 140 is shown in a fixed orientation relative to lower handle portion 120 and upper handle portion 110, it will be understood that driving head 140 may be articulated, either in the plane of the vertical interface 51 or perpendicular to the plane of the vertical interface 51, to allow for increased maneuverability and orientation of driving head 140. Alternatively, lower handle portion 120 may be articulated relative to upper handle portion 110, or both lower handle portion 120 and driving head 140 may be articulated.

Preferably, anvil portion 144 of driving head 140 has apertures 152 formed therethrough. Apertures 152 are appropriately sized so as to slidingly receive penetrators or pilot needles 154, 156 and may be bore directly into the material of anvil portion 144 or may be lined with a metal guide tube or the like inserted into a bore in anvil portion 144. Pilot needles 154, 156 have a generally arcuate shaped cross-section throughout distal portions 155, 157, and a solid cylindrical cross-section in proximal portions 159, 161. Each distal portion 155, 157 has an inner concave surface 158, 160 for accommodating and retaining a fastener 400, and each proximal portion 159, 161 engages the back surface of the fastener 400, allowing the fastener to be advanced distally with the needles. The distal ends 162, 164 of pilot needles 154, 156 have a sharp point for penetrating skin. Pilot needles 154, 156 are vertically disposed at a distance dl below top surface 166 of anvil portion 142. It is preferably that top surface 166 be usable as a reference datum for visually gauging whether pilot needles 154, 156 are located within target tissue zone 70. Accordingly, it is preferable that distance dl be between 0.1 mm and 2.0 mm, and most preferably between 0.2 mm and 0.8 mm, so that when top surface 166 is aligned with the outer skin surface, pilot needles 154, 156 are located within target tissue zone 70 and most preferably within most preferred area 72.

Delivery mechanism 128 serves to eject a fastener from driving head 140. Preferably, slide block 122 is slidably mounted on guides 124, 126, within lower handle portion 120. Slide block 122 is engaged with trigger 200 so that actuation of the trigger causes sliding movement of slide block 122. Pilot needles 154, 156 are fixedly attached to slide block 122, and extend outwardly through backing portion 144 of driving head 140 through slot 168. Thus, back and forth sliding motion of slide block 122 causes pilot needles 154, 156 to be extended and retracted from slot 168, gap 148 and apertures 152. It will be understood that any number of mechanical driving arrangements can be used to impart the necessary force to pilot needles 154, 156, or alternatively to the fastener 400 directly. Examples include sliding mechanisms, cam mechanisms, spring-operated mechanisms, screw drives, pneumatic drives, automated motion control drives, or the like.

Pilot needles 154, 156 are preferably spaced apart by an interneedle distance of between about 2.0 mm and 20 mm and most preferably between about 4.0 mm and 16.0 mm, so that when the driving head in placed within a skin opening to be fastened, and with the skin opening aligned with the approximate midpoint between the pilot needles, the pilot needles will be located within the width orientation of the target tissue zone 70.

Figure 14:
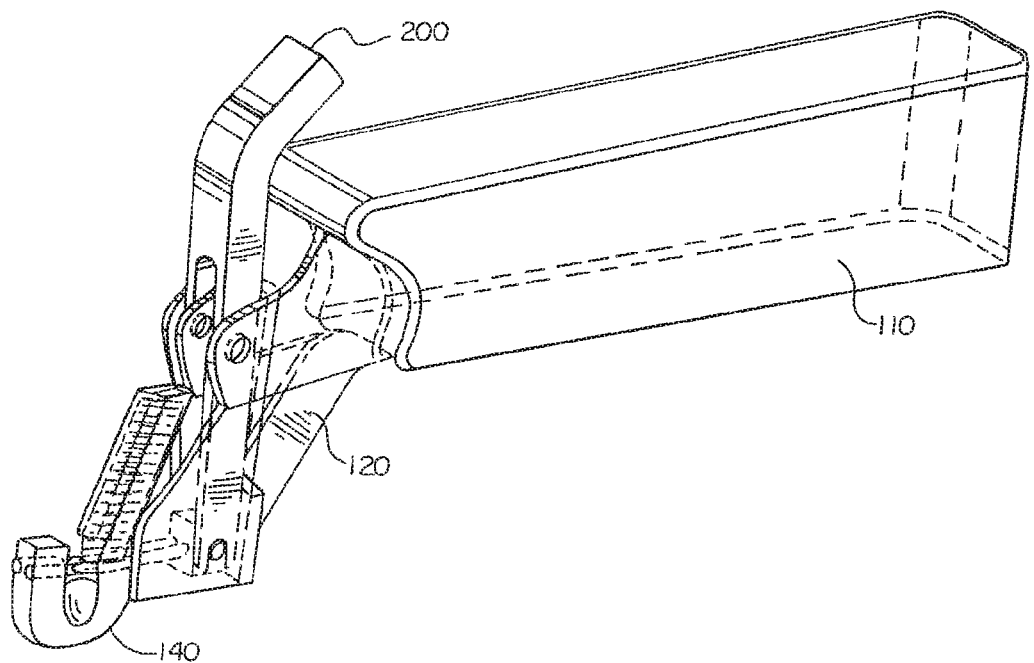
FIG. 14 is a phantom view of the applicator apparatus of an embodiment of the present invention having an automated fastener delivery and storage mechanism.
Figure 15:
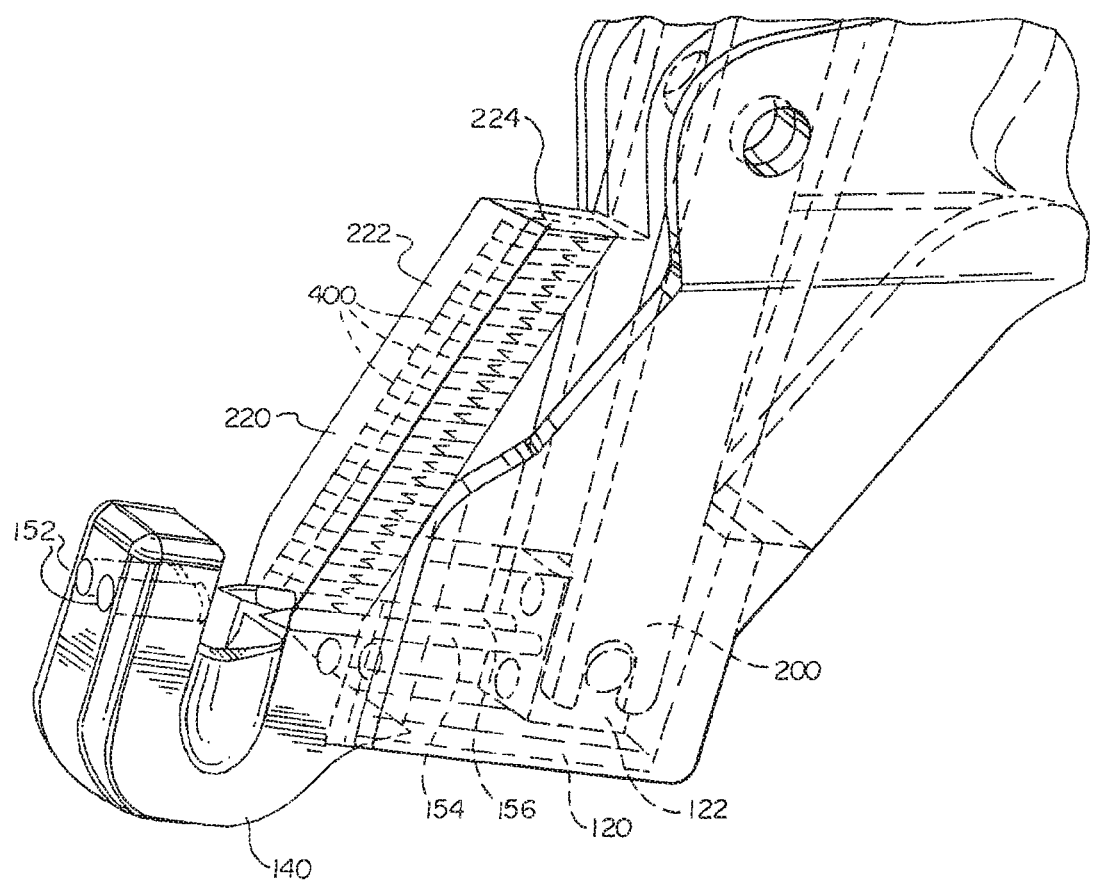
FIG. 15 is an enlarged phantom view of the apparatus of FIG. 14.
Figure 16:
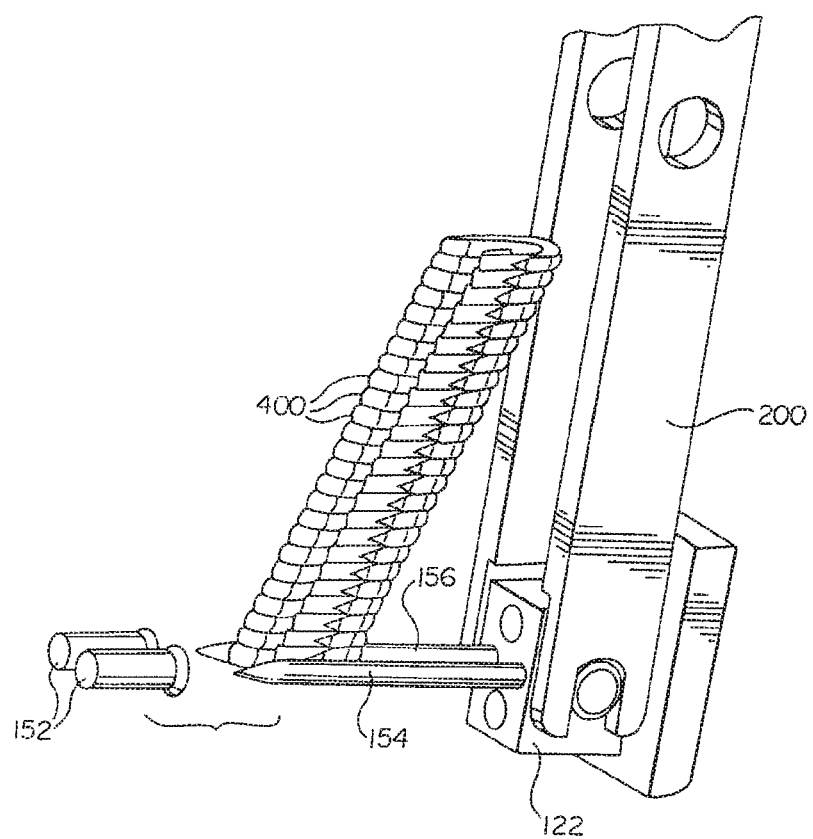
FIG. 16 is a partial view of the apparatus of FIG. 14.

Although single fasteners may be inserted manually one-by-one between pilot needles 154, 156, an alternative embodiment of applicator assembly 100, shown in phantom in FIGS. 14-16 has an automated fastener delivery and storage mechanism 220. In this mechanism, fasteners are preferably stacked vertically in echelon fashion surrounding a guide member 224, and are biased downwardly with a resilient member such as a spring (not shown). Housing 222 is provided to protect the mechanism. The bottom-most fastener in the echelon is engaged with pilot needles 154, 156. As each fastener 400 is emplaced in the skin through operation of the applicator assembly 100 as described herein, and slide block 122 is returned to the proximal limit of travel, the downward bias of the echelon causes the immediately vertical adjacent fastener to move downward and become engaged within pilot needles 154, 156. The next fastener may then be emplaced in the skin, and the process repeated. Again, it will be appreciated that numerous arrangements and configurations for providing and deploying multiple fasteners within the context of the present invention could be used, such as inline stacking in either a horizontal or vertical orientation, side-by-side stacking, rotational presentation via a circular chamber or magazine or belt or tape-attached presentation of the fasteners 400.

Figure 17:
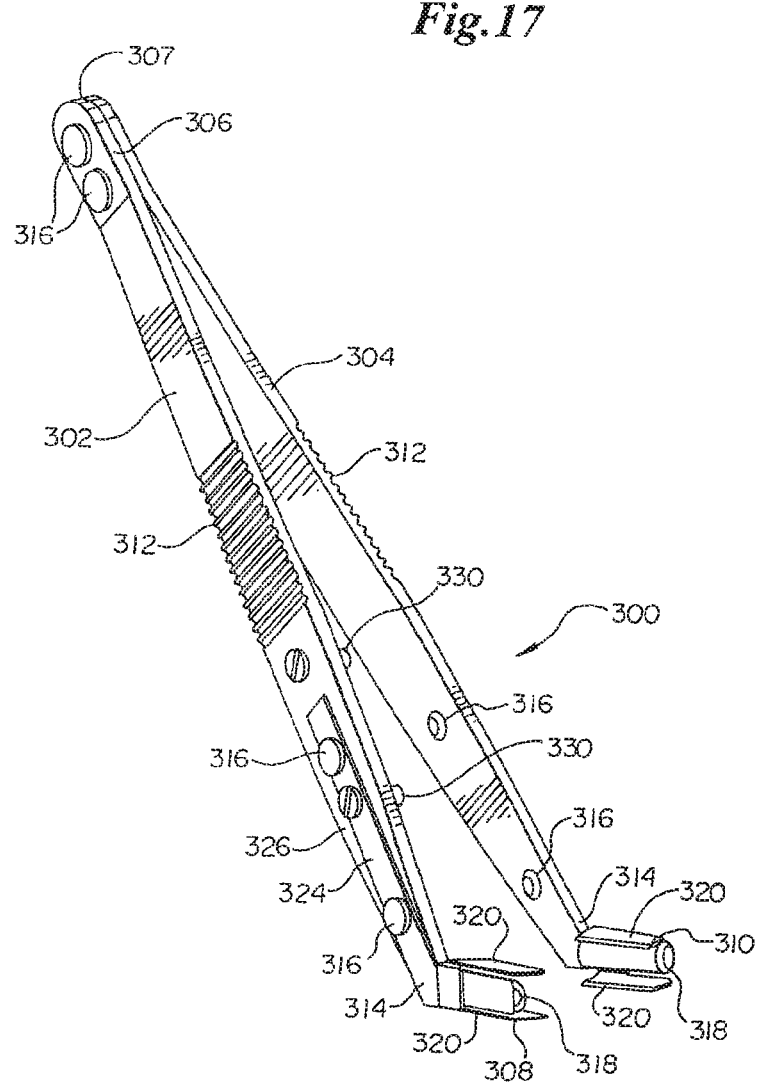
FIG. 17 is a perspective view of an embodiment of a manipulator apparatus according to the present invention.
Figure 18:
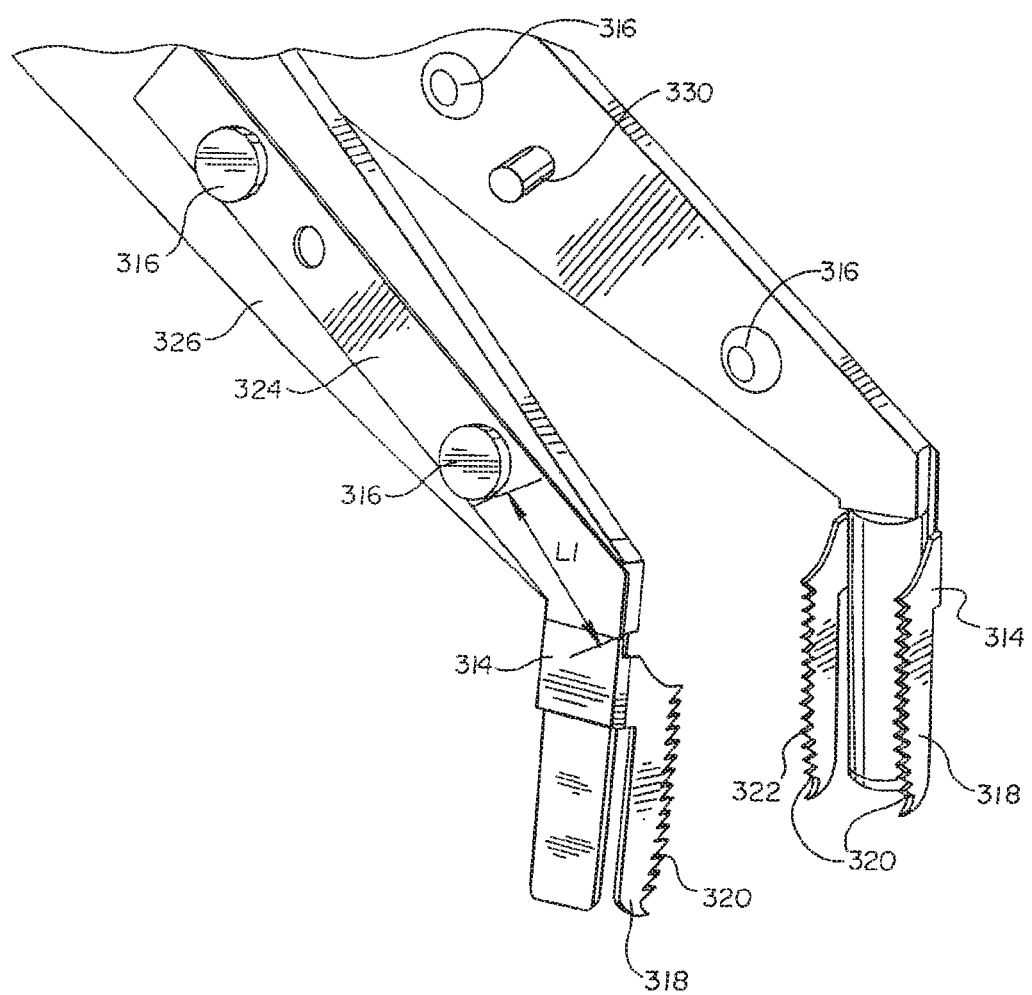
FIG. 18 is an enlarged view of the jaw portions of the manipulator apparatus of FIG. 17.

In FIGS. 17 and 18, there is shown an embodiment of the tissue manipulator assembly 300 of the present invention. The proximal ends 307 of arms 302, 304 are joined together at fulcrum 306, forming the tweezer-like structure of the overall assembly. Gripping areas 312 are provided on each arm to allow gripping of the assembly with the fingers. Any suitable fastening method may be used at fulcrum 306, including rivets 316 as shown, or the arms 302, 304 may be welded, cast, or molded together or may otherwise be integrally formed together. The material and overall dimensions for arms 302, 304 are selected so as to allow the arms to be resiliently compressed inwardly with the fingers, and with a memory characteristic for returning to the original position upon the removal of pressure. In addition, the material used for the arms and other portions of the assembly are preferably thermally and chemically stable so as to allow sterilization with either heat or chemical means. The preferred material for arms 302, 304 is stainless steel.

At the distal ends 309 of each arm 302, 304 are formed tissue manipulator surfaces 318. Manipulator surfaces 318 are preferably semi-cylindrically shaped as shown, with the diametrical dimension of each semi-cylinder selected so as to conform to the diameter and shape of the concave areas 150 of applicator assembly 100. Skin gripping jaw members 314 are preferably attached to the exterior surfaces 326 of each arm member 302, 304. Each jaw member 314 has a backing portion 324 for attaching to the arms, and a pair of inwardly directed projections 320 disposed on both sides of manipulator surfaces 318. Directly opposed serrations 322 are preferably provided on the inward-most edge of each projection 320 for better skin purchase. Backing member 324 may be attached to each arm 302, 304 using any suitable attachment method, including mechanical fasteners such as the rivets 316 as shown. For reasons that will be further explained, it is preferable that each jaw member 314 is of sufficient resilience and is attached so that inwardly directed projections 320 may deflect separately from skin manipulator surfaces 318 under moderate finger pressure applied to arms 302, 304. This may be achieved through concerted selection of the material used for jaw member 314, the thickness dimension of backing member 324, and the free length L1 of each backing member 324 between the inwardly directed projections 320 and the fastener 316 closest to the distal end 309 of the arm. The objective of the design of the backing member 324 is to have the jaw members 314 engage tissue with a first force and have the manipulator surfaces 318 engage tissue between the jaw members 314 with a second force that is greater than the first force. In addition, the use of a pair of directed projections 320 on each side of the vertical interface 51 serves to stabilize the tissue laterally between the pair of projections 320.

Mechanical stops 330 are provided to prevent pressure beyond that necessary to ensure optimal approximation of tissue into gap 148 and concave portions 150 of applicator assembly 100 from being transmitted through manipulator surfaces 318. Preferably, mechanical stops 330 are set so that manipulator surfaces 318 close to a distance that is spaced apart from the interneedle distance of pilot needles 154, 156 by a range of 0.2-0.8 millimeters, such that the total distance between mechanical stops 330 is 0.4-1.6 millimeters greater than the interneedle distance between pilot needles 154, 156. In a preferred embodiment in which the interneedle distance is set at 3.25 millimeter, the mechanical stops 330 would allow the surfaces 318 to close to within a range of 3.65-4.85 millimeters when approximating tissue into gap 148. Although jaw members 314 may be formed from any suitable material, the preferable material is stainless steel.

Figure 19:
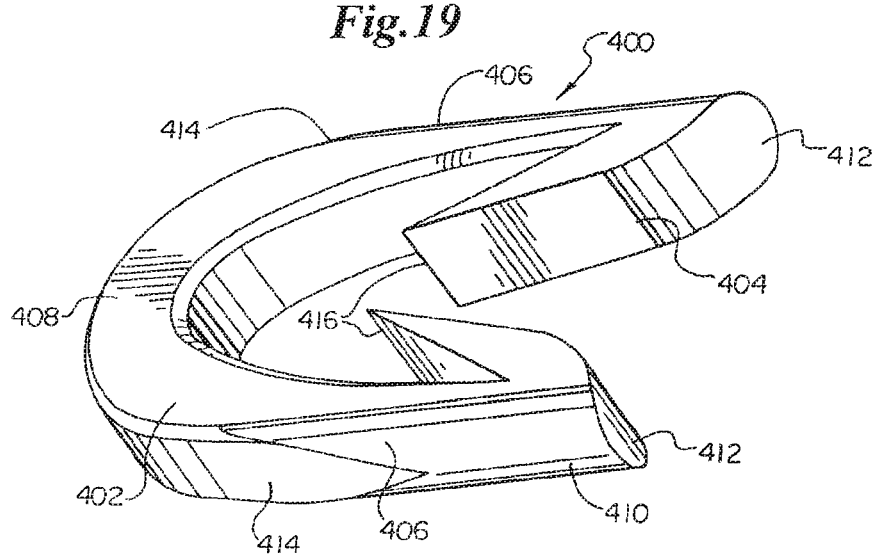
FIG. 19 is a perspective view of an embodiment of a fastener according to the present invention.
Figure 20:
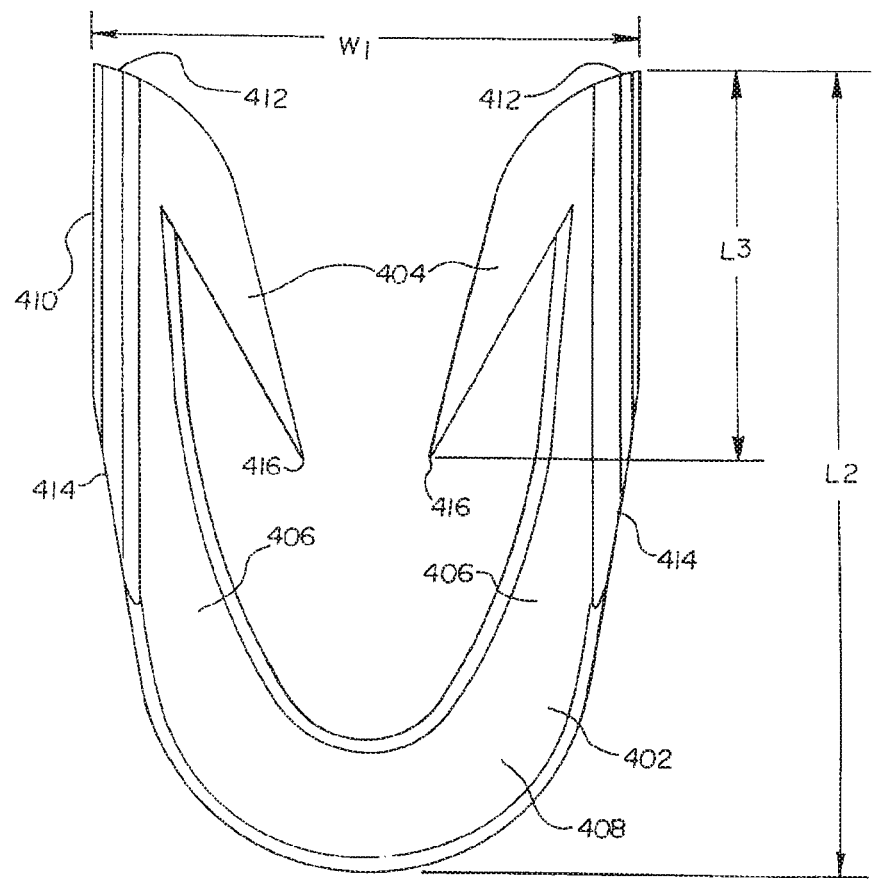
FIG. 20 is a top plan view of the fastener depicted in FIG. 19.

In FIGS. 19 and 20, there is shown an embodiment of a fastener 400 of the present invention. Fastener 400 has body portion 402, which comprises a cross-member 408 connecting a pair of fork members or legs 406. The outer margins 410 of each leg 406 are dimensioned and shaped accommodatingly to the inner concave surfaces 158, 160, of pilot needles 154, 156, allowing fastener 400 to fit and slide between the distal portions 155, 157 of the needles, as is shown best in FIGS. 12 and 13. Shoulders 414 preferably are provided to engage the solid cylindrical cross-section of the proximal portions 159, 161 of pilot needles 154, 156, thus allowing fastener 400 to be advanced distally with motion of the needles. The distal end 412 of each leg 406 is incurvately shaped to allow easier passage through an opening in skin, referred to as a skive, that is created by pilot needles 154, 156. Inwardly directed barbs 404 preferably are provided on each leg 406 to resist withdrawal of the fastener once emplaced.

Although an overall U-shape for the fastener 400, as shown in FIGS. 19 and 20 is preferred, other shapes having a capability for bilateral tissue engagement are also possible and within the scope of the invention. Such other shapes include for example, but are not limited to, a square shape similar to an ordinary staple, a semi-circular or C-shape or a V-shape or W-shape, in which the cross-member 408 has bends or other features. While the shape of fastener 400 is generally determined in a planar configuration, it will be recognized that other non-planar shapes and configuration can be used, such as a fastener having multiple projections for each leg 406, with each projection oriented in a different plane, or a fastener having cross-member 408 arranged in a V-shape projecting out of the normal plane of the fastener 400. Two leg members 406 are preferred, but it will be understood that additional leg members 406 could be added in the same or a different plane of the fastener 400 such that the leg members of each side of the fastener form a dident or trident configuration, for example.

Figure 39:
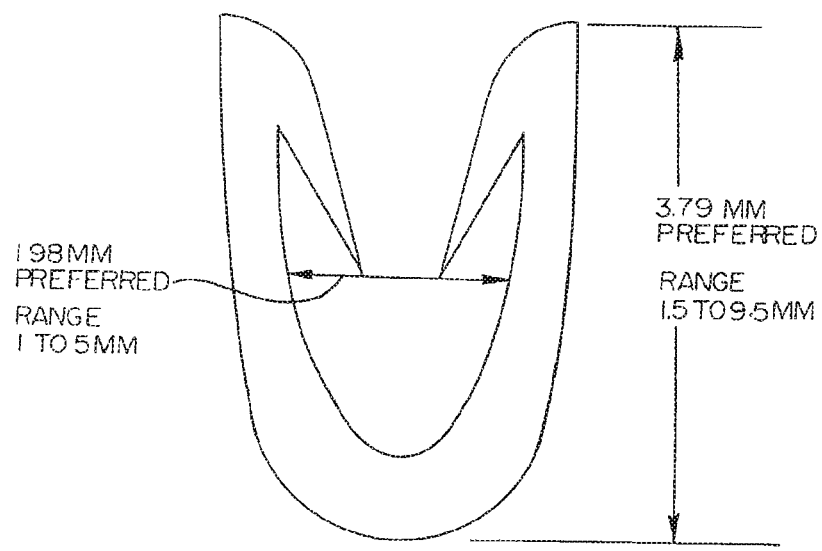
FIG. 39 is a plan view of an embodiment of a fastener showing the inner cross-sectional area.
Figure 40:
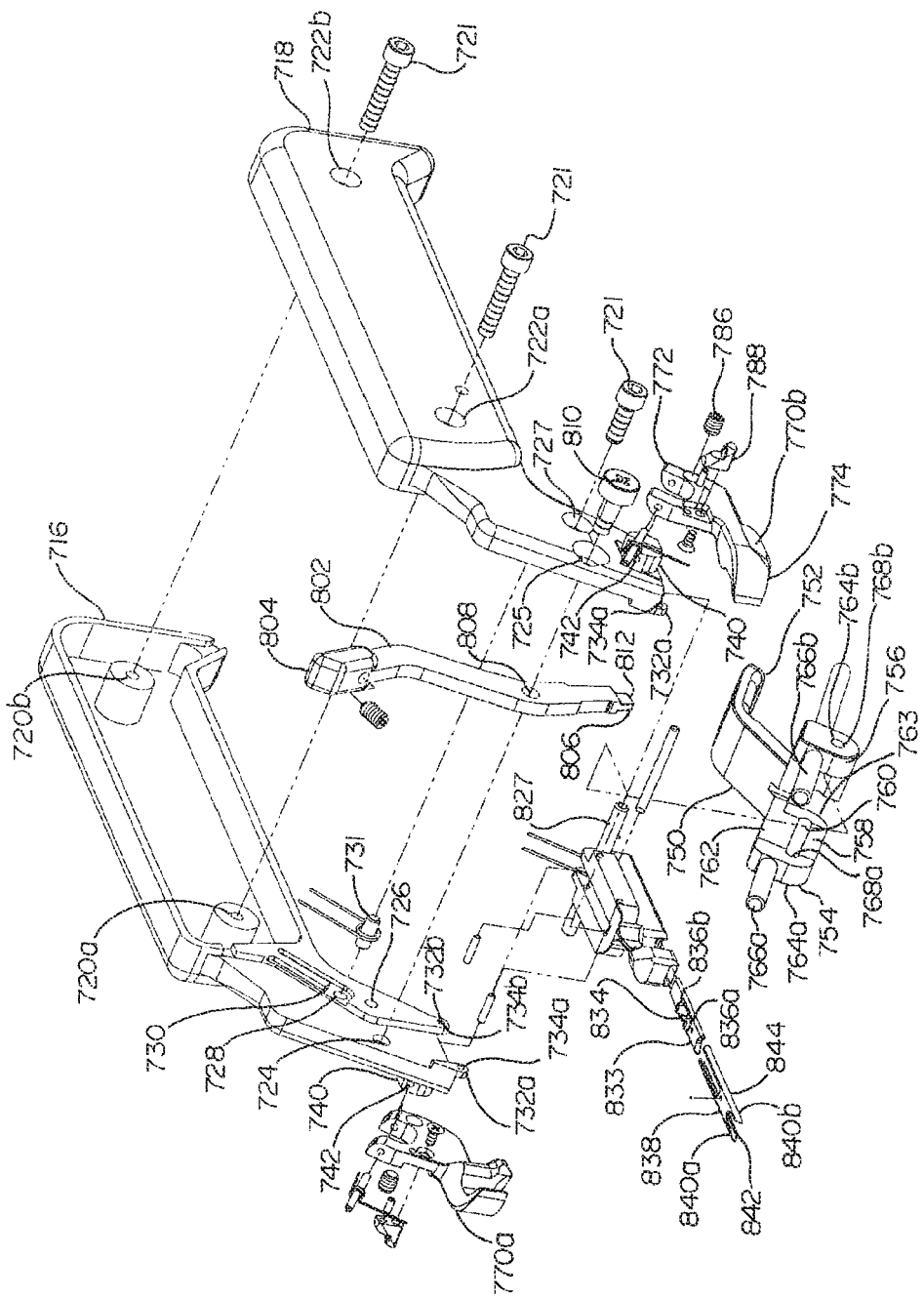
FIG. 40 is an exploded perspective view of an alternative embodiment of the present invention in which a tissue manipulator assembly and an applicator assembly are incorporated into a single handheld surgical instrument.
Figure 41:
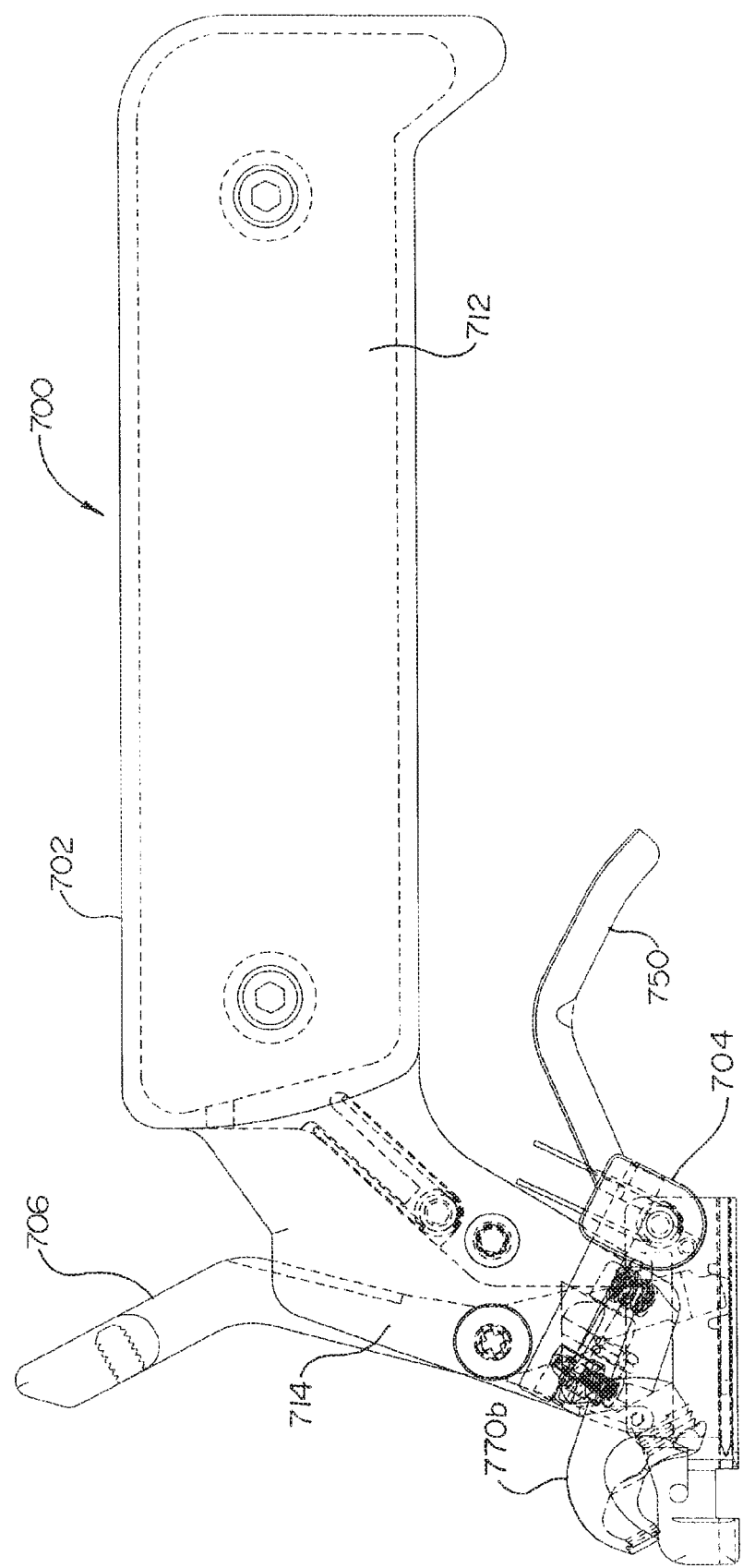
FIG. 41 is a side view of the handheld surgical instrument shown in FIG. 40.
Figure 42:
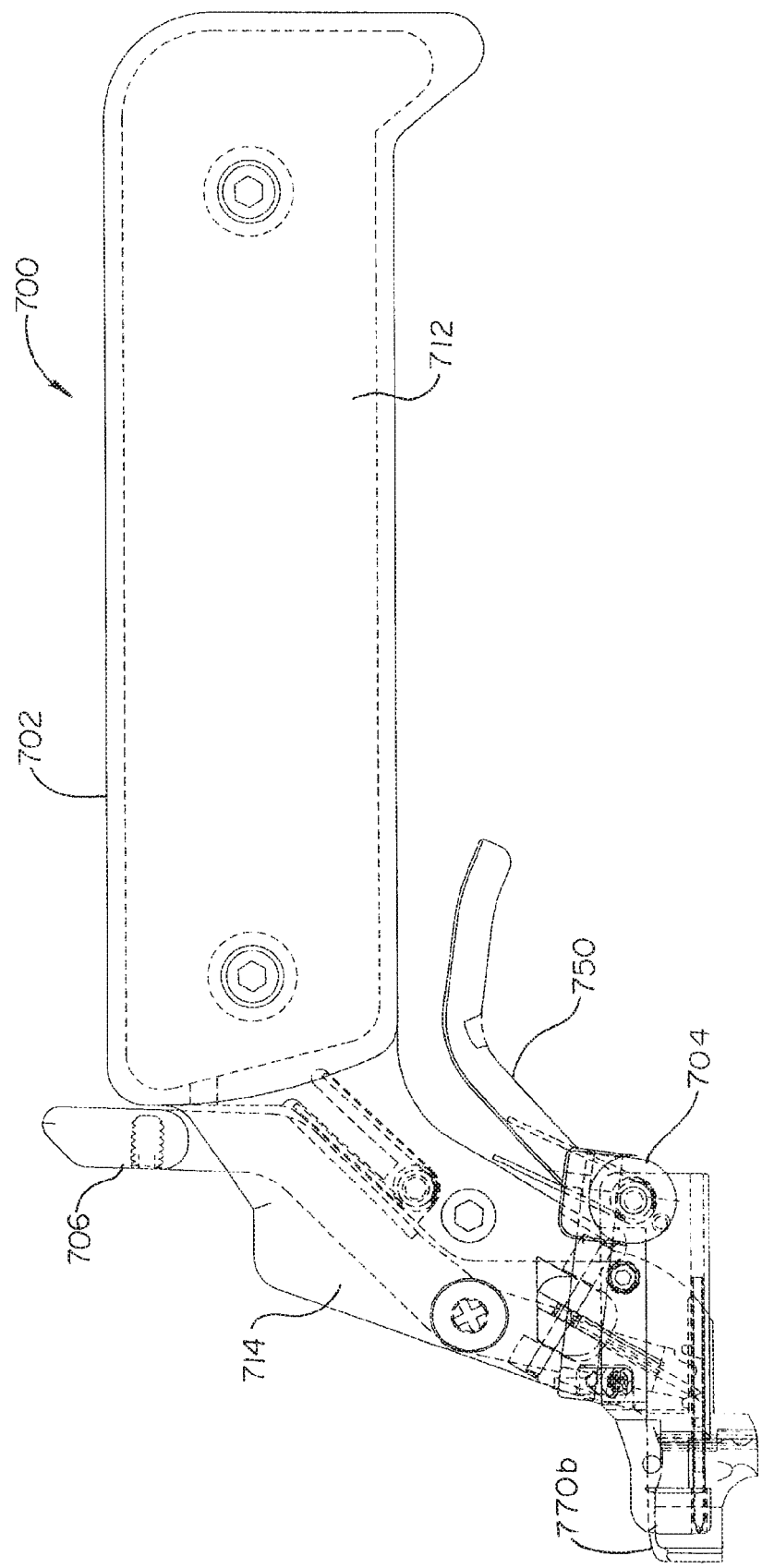
FIG. 42 is a side view of the handheld surgical instrument shown in FIG. 40.
Figure 43:
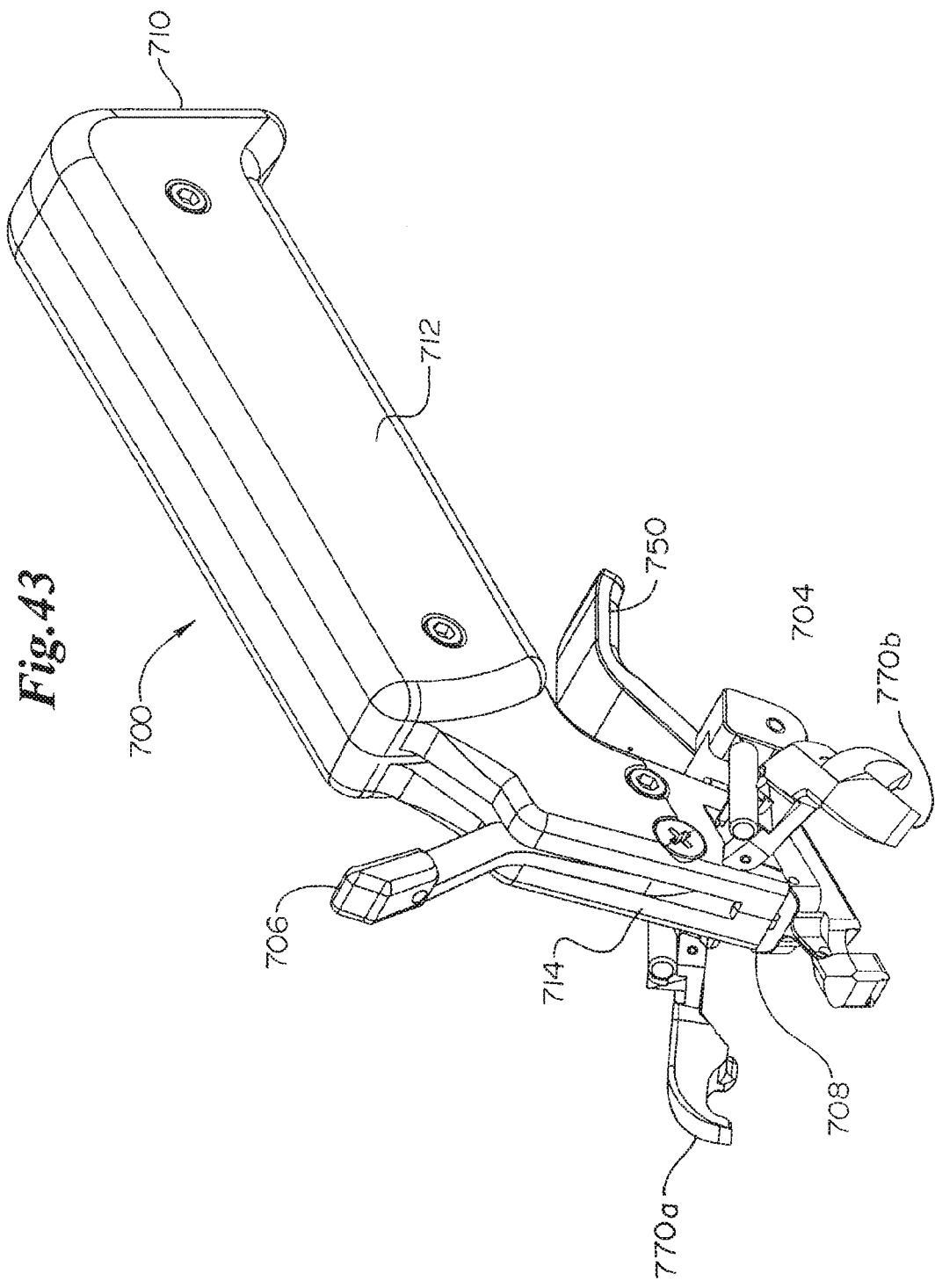
FIG. 43 is a perspective view of the handheld surgical instrument shown in FIG. 40.
Figure 44:
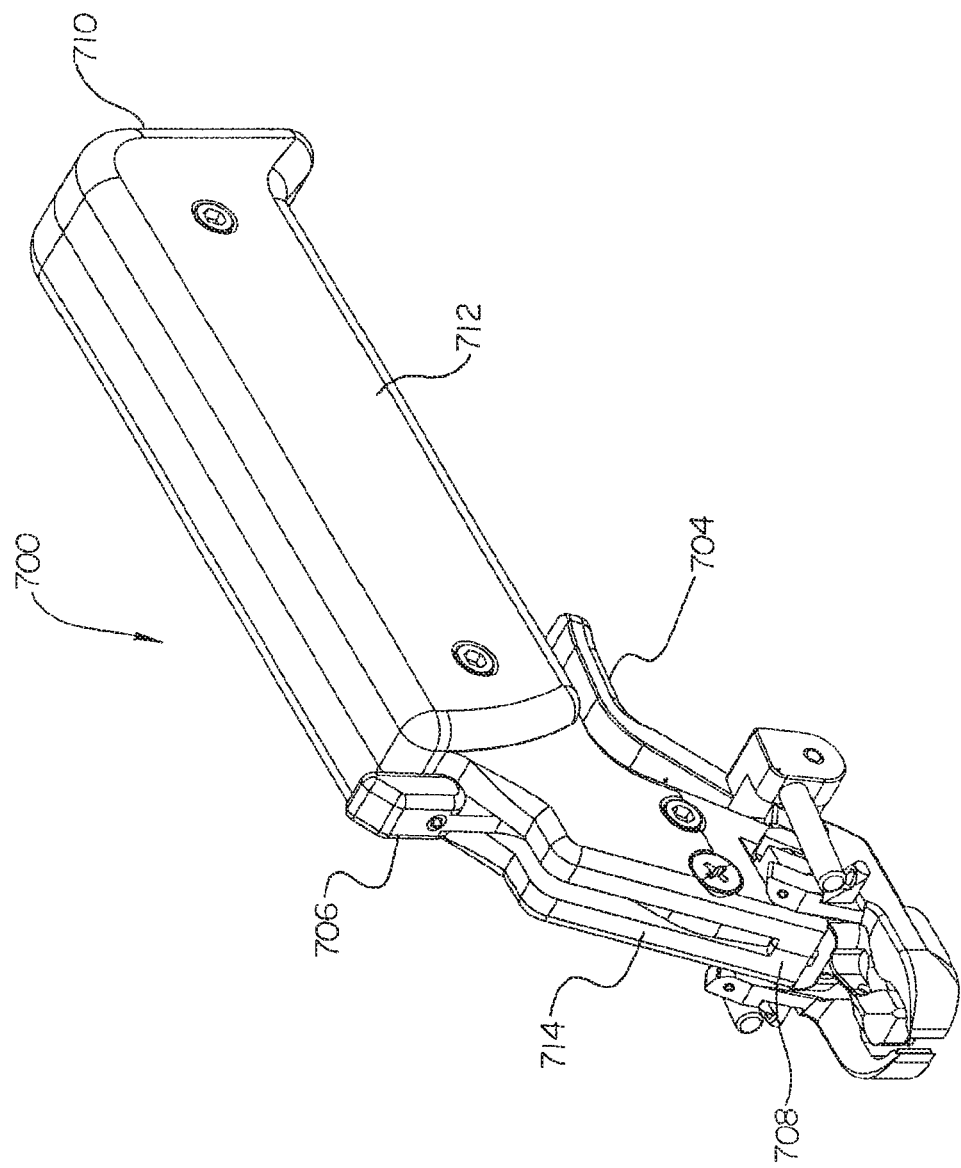
FIG. 44 is a perspective view of the handheld surgical instrument shown in FIG. 40.

As shown in FIG. 39, an inner cross-sectional area 409 is defined by the fastener 400 for capturing the compressed dermal tissue. In a preferred embodiment, inner cross-sectional area 409 ranges from 1.5 sq. mm to 50 sq. mm and most preferably about 5 sq. mm to 10 sq. mm. This area is generally defined by an inner diameter length of between 1.5 mm and 9 mm and most preferably about 3.8 mm and an inner diameter width of between 1 mm and 5 mm and most preferably about 2 mm. It will be apparent that numerous shapes and configurations can be used for the shape and arrangement of cross-sectional area 409. Preferably, inner cross-sectional area 409 is generally arrowhead shaped as a result of the positioning of the barbs 412. As will be described, the barbs 412 or similar anti-reversing projections resist against the withdrawal of fastener 400. While the barbs 412 are preferably oriented into the inner cross-sectional area 409, it will be appreciated that barbs 412 may be omitted or may be oriented outwardly.

Although it is possible for fastener 400 to be deformed during delivery and application, preferably the majority of dermal tissue retained within cross-sectional area 409 is captured in a compressed state by a fastener 400 that is sufficiently rigid so as to retain the dimensional integrity of cross-sectional area 409 within +/−30% of its designed area for a period of preferably at least 10 days. Most preferably, structural integrity of fastener 400 is maintained for at least 21 days. In this way, the dermal tissue captured in fastener 400 is retained in a compressed state for a period sufficient to allow the biological healing process to occur without the dermal tissue being under tension during the healing process. Preferably, the dimensions of the fastener 400 and the operation of the applicator assembly 100 coordinate to create a compression ratio of dermal tissue within the inner cross-sectional area 409 that is greater than one. The compression ratio is defined either as a ratio of area or a ratio of width. In the case of width, the compression ratio is the ratio of the dimension defined by the position of the skive relative to the vertical interface 51 when the dermal tissue is at rest divided by the position of the skive relative to the vertical interface as held by the fastener 400. In the case of area, the compression ratio is the ratio of the area of dermal tissue that will be retained by the fastener 400 when that dermal tissue is at rest divided by the actual cross-sectional area 409.

Alternatively, it is possible to take advantage of the bilateral tissue fastening in the tissue target zone as taught by the present invention with a deformable fastener where the deforming of a bioresorbable or bioabsorbable fastener serves to provide at least some of the compression of the dermal tissue such that the need for a mechanical tissue manipulator is reduced or potentially eliminated. In this embodiment, a bioresorbable or bioabsorbable fastener would be deformed by the applicator apparatus in order to appropriately compress the dermal tissue. Deformation of a bioresorbable or bioabsorbable fastener could be accomplished in a number of ways, including prestressing the fastener into an open configuration such that it returns to a closed configuration, with or without mechanical assistance from the applicator, application of ultrasound, heat or light energy to alter the shape of, or reduce or relax stresses in, the fastener in situ, designing a polymer material with appropriate shapes and compositions that the material is deformable upon deployment without fracturing, or any combination of these techniques.

Fastener 400 is preferably formed from any suitable biodegradable material. The currently most preferred biodegradable material is a lactide/glycolide copolymer where the ratio is never less than at least 10% of one element and preferably in a range of 60%-70% lactide. Examples of other suitable materials include poly(dl-lactide), poly(l-lactide), polyglycolide, poly(dioxanone), poly(glycolide-co-trimethylene carbonate), poly(l-lactide-co-glycolide), poly(dl-lactide-co-glycolide), poly(l-lactide-co-dl-lactide) and poly(glycolide-co-trimethylene carbonate-co-dioxanone). In addition, other suitable materials could include compositions with naturally occurring biopolymers such as collagen and elastin, or stainless steel, metal, nylon or any other biocompatible materials in the case of a non-absorbable fastener, or even various combinations of such materials depending upon the desired application and performance of the fastener.

Figure 12:
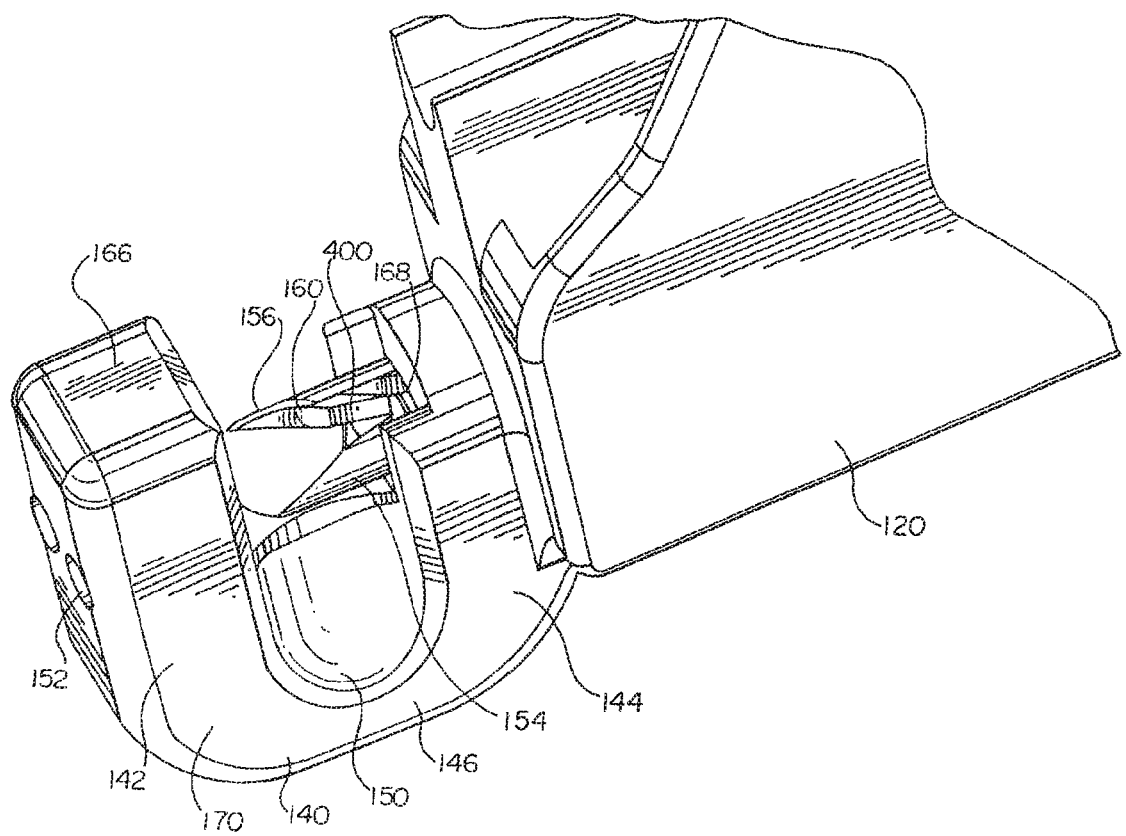
FIG. 12 is a perspective view of the lower handle and driving head portions as depicted in FIG. 8 with a fastener positioned therein.
Figure 13:
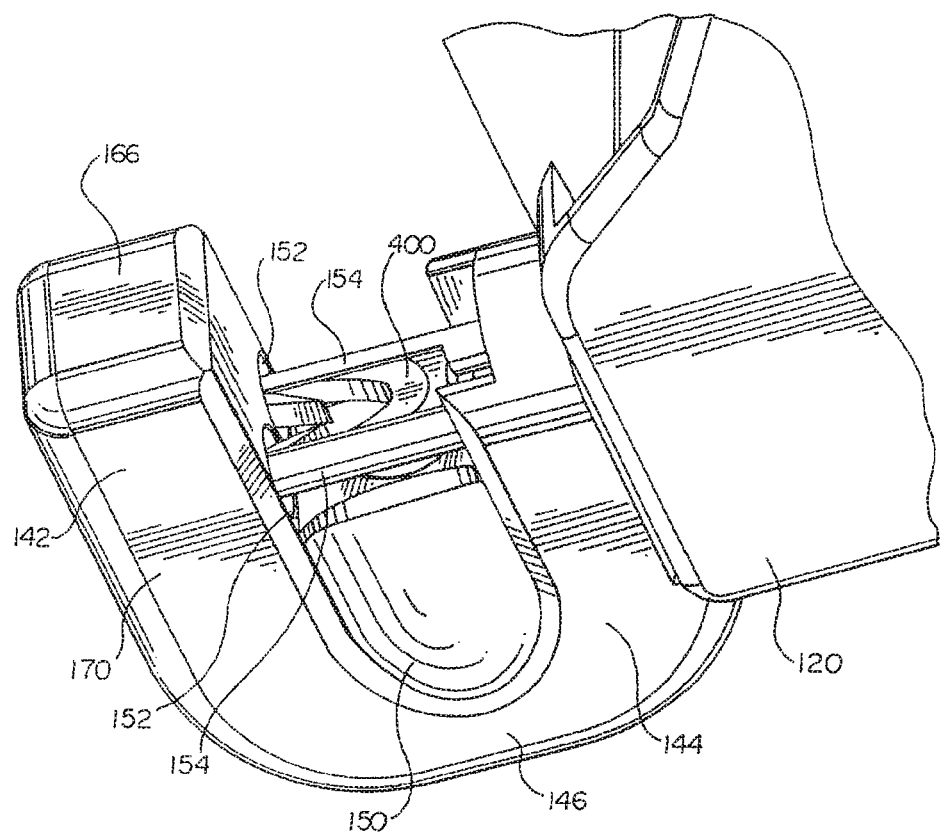
FIG. 13 is another perspective view of the lower handle and driving head portions as depicted in FIG. 8 with a fastener positioned therein.
Figure 21:
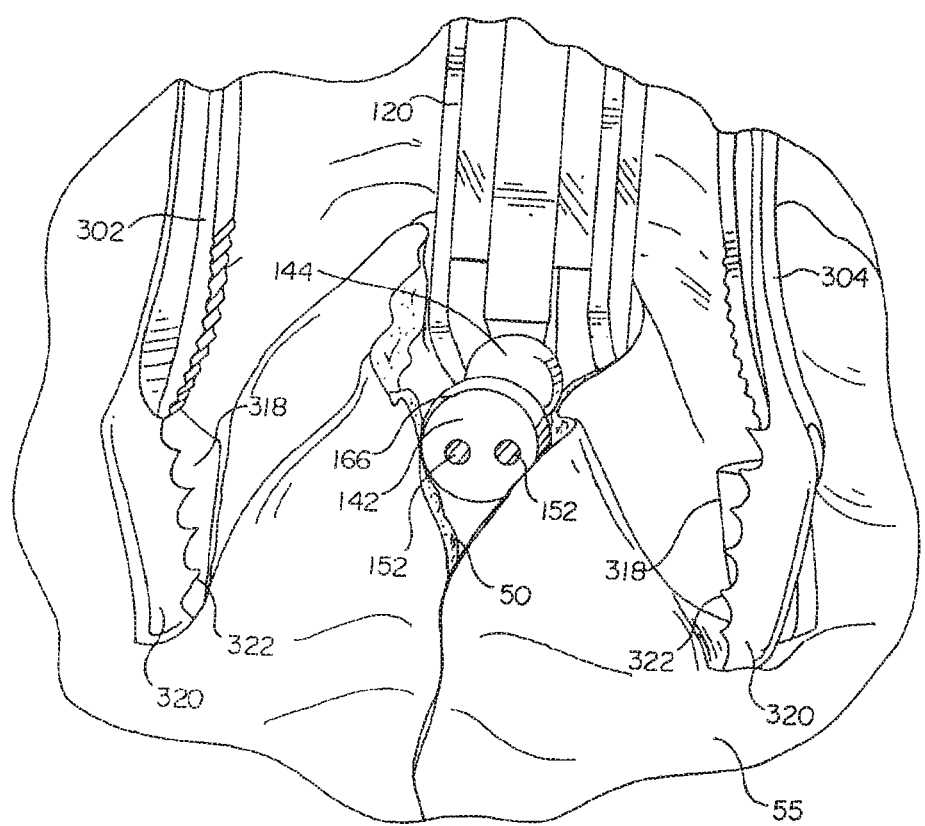
FIG. 21 is a perspective view showing the orientation of applicator and manipulator apparatus during a step of an embodiment of the method of the present invention.
Figure 22:
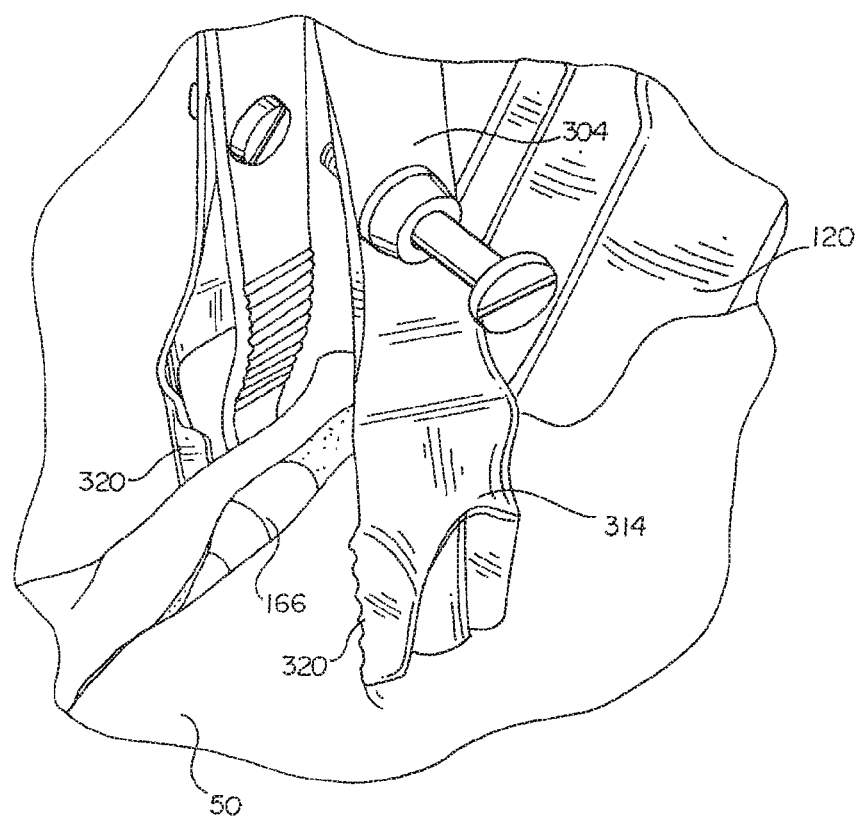
FIG. 22 is a perspective view of the apparatus during another step of an embodiment of the method of the present invention.
Figure 23:
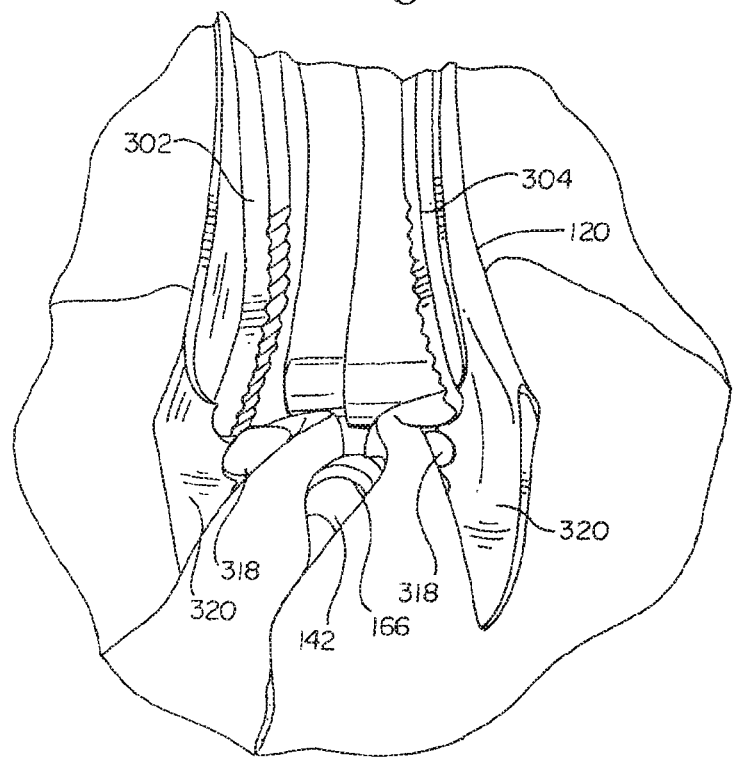
FIG. 23 is a perspective view of the apparatus during yet another step of an embodiment of the method of the present invention.
Figure 24:
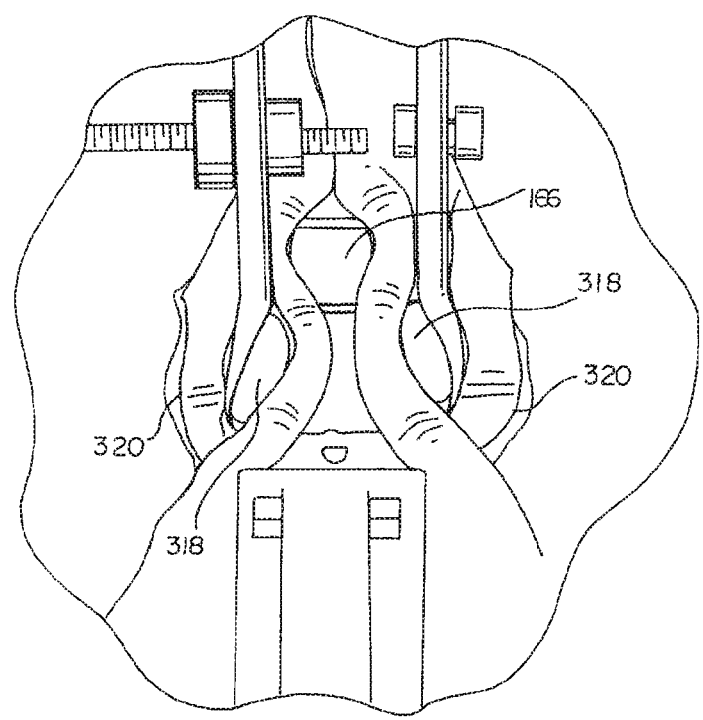
FIG. 24 is a perspective view of the apparatus during still another step of an embodiment of the method of the present invention.
Figure 29:
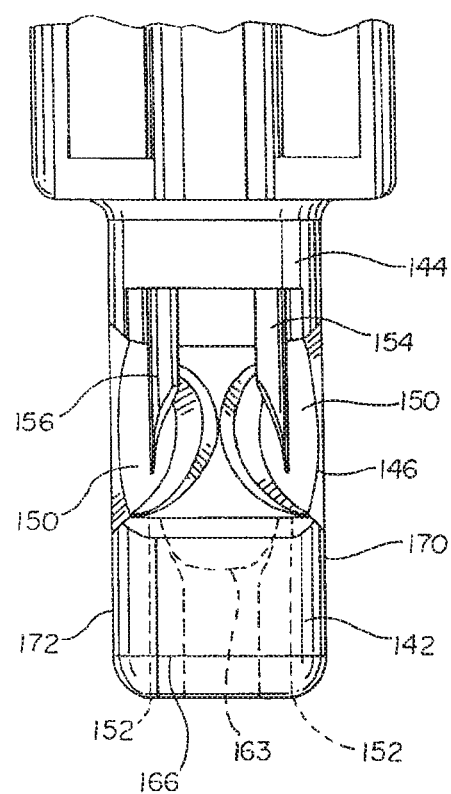
FIG. 29 is another view of an applicator assembly according to an alternative embodiment of the invention.

With reference to FIGS. 21-24, the operation of the apparatus of the present invention may now be explained and understood. A fastener 400 is first loaded between pilot needles 154, 156, as shown in FIG. 12. Slide block 122 is then proximally retracted to the fullest extent so that pilot needles 154, 156 and the fastener 400 are entirely within slot 168. Driving head 140 is then introduced into skin opening 50 and top surface 282 is aligned with the outer surface of the skin as shown in FIG. 21. Tissue manipulator assembly 300 is placed with jaw members 314 on either side of driving head 140. Arms 302, 304 of manipulator assembly 300 are pressed inward so that jaws 314 engage the skin surface and begin to force the skin 52 into gap 148 in applicator assembly 100 as shown in FIG. 22. Serrations 322 provide purchase on the skin surface and prevent lateral slipping of the skin relative to the jaws. As further inward pressure is applied to arms 302, 304, inwardly directed projections 320 engage side surfaces 170 of anvil portion 142 and side surfaces 172 of backing portion 144, each with a single thickness of skin trapped between as shown in FIG. 23. Still further inward pressure on arms 302, 304, as shown in FIG. 24, causes tissue manipulator surfaces to deflect inward slightly from jaws 314, until each engages concave area 150 of cross-member 146 with a layer of skin trapped in between. In this position, inner surfaces 60 of dermal layer 56 are in direct contact with each other within gap 148 and substantially parallel with vertical interface 51, but are not overlapped or interdigitated.

In this embodiment, pilot needles 154, 156 are aligned generally horizontally and substantially parallel with the outer surface of the skin and are within target tissue zone 70. Cross-member 408 of fastener 400 is positioned generally transverse to vertical interface 51 and a working plane of fastener 400 defined by cross-member 408 and legs 406 is generally horizontal in orientation. Trigger 280 is then actuated, causing slide block 122 to move proximally within lower handle portion 120, and advancing pilot needles 154, 156 into the skin, creating a skive through the target tissue zone 70 of the skin on each side of vertical interface 51. Fastener 400 moves with pilot needles 154, 156, and each leg 406 of the fastener 400 is simultaneously driven into and through the skive. Once fastener 400 is advanced distally a sufficient distance so that barb tips 416 of fastener 400 enter apertures 152 and accordingly emerge from the skive, trigger 280 may be reversed so that slide block 122 moves proximally, retracting pilot needles 154, 156. Barbs 412 engage the skin, thereby preventing fastener 400 from being withdrawn with the pilot needles. Once slide block 122 has been fully retracted proximally, thereby causing pilot needles 154, 156 to be fully retracted from gap 148, the pressure on manipulator assembly 300 may be released and applicator assembly 100 can be moved proximally in the opening 50 to deliver another fastener 400 or can be removed from opening 50.

In addition to the embodiment of the apparatus described above wherein the legs of a fastener are simultaneously driven through the target tissue zone on each side of the skin opening and with the fastener legs oriented parallel to the epidermal skin surface, those of skill in the art will appreciate that other embodiments of a mechanical fastening system for openings in skin tissue are within the scope of the present invention. For instance, the working plane of fastener 400 defined by cross-member 408 and legs 406 may be oriented generally orthogonal, or oblique in at least one orientation, to the horizontal plane generally defined by exterior surface 55 of epidermal layer 54. In such an embodiment, fastener 400 may be inserted in a generally vertical orientation with legs 406 pointing generally in an upward direction or in a downward direction.

Another embodiment of the apparatus of the present invention wherein a fastener is driven sequentially through the bilateral target tissue zones is shown in FIGS. 25-29. In one embodiment, fastener 500 has flexible body portion 502 with a barb 506 at distal end 505 and an attachment flap 504 at proximal end 503. Flexible body portion 502 is dimensioned so as to be received within either concave inner surface 158, 160 of pilot needles 154, 156. Attachment flap 504 has slot 508 formed therethrough, which is adapted to receive barb 506. In applicator assembly 100, anvil portion 142 has concave deflector 153 formed between apertures 152 and extending into a portion of each aperture 152 so that only an area of each aperture is open sufficient to allow the arcuate cross-section of pilot needles 154, 156 to pass. In operation, and with reference to FIGS. 1-29, fastener 500 is axially aligned with pilot needle 154, and is inserted within the corresponding concave inner surface of the needle with barb 506 oriented toward the point of the needle. Applicator assembly 100 is then introduced into the interface portion 51 of the skin opening 50 as described above. Tissue manipulator assembly 300 is then applied as before to bring the dermal layer 56 into contact within gap 148, and thereby properly positioning target tissue zone 70. As slide block 122 and the attached pilot needles 154, 156 are moved distally through actuation of trigger 280, fastener 500 is advanced through the skin tissue on one side of skin opening 50 along with pilot needle 154 in which it is disposed. Once the tip of barb 506 reaches aperture 152, however, it is engaged by, and begins to slide laterally along, concave deflector 163, causing flexible body portion 502 to bend. As pilot needles 154, 156 are further advanced, barb 506 is turned in direction 180 degrees by deflector 163. It will be appreciated that the barb 506 may either be positioned in front of pilot needle 154 by an amount sufficient to redirect barb 506 into the opposite direction or pilot needle 154 may advance into the corresponding aperture 152 to a depth at which the redirection of barb 506 upon the entry to aperture 152 will be sufficient to redirect barb 506 into the opposite direction. Once redirected and positioned in line with the second skive, barb 506 is advanced in the opposite direction by pilot needle 156 and through the skin tissue on the opposite side of the vertical interface 51 as pilot needle 156 is withdrawn. Once barb 506 emerges from the dermal tissue, attachment flap 504 may be bent so that barb 506 may be pushed through slot 508, thus securing fastener 500 in a loop and bilaterally capturing both sides of the skin opening 50. It will also be appreciated that attachment flap 504 may be replaced by suitable structure on flexible body 502 for engaging a suture. The suture lock of co-pending application entitled "Suture Lock Having Non-Through Bore Capture Zone," U.S. patent application Ser. No. 10/166,161, filed Jun. 10, 2002, which is commonly owned by the assignee of the present invention and the disclosure of which is hereby incorporated by reference, may then be used to secure the suture to barb 506, completing the bilateral capture. In this embodiment described herein, the skives are created simultaneously and the fastener 400 is inserted sequentially into each corresponding skive from an opposite direction. Alternatively, a single U-shaped needle could be utilized in place of pilot needles 154, 156 and both the skives and fastener could be created and inserted sequentially. Numerous other combinations of bilateral creation of skives and insertion of fasteners are contemplated by scope of the present invention.

As described herein, the fastener is oriented so that a working plane defined by the flexible body 502 of fastener 500 is substantially parallel to a plane generally defined by exterior surface 55 of epidermal layer 54, and transverse to vertical interface 51. Those of skill in the art will appreciate, however, that the working plane of fastener 500 could also be oriented substantially orthogonal, or oblique, with the plane generally defined by exterior surface 55 while remaining in a transverse orientation with respect to vertical interface 51. Those of skill in the art will also appreciate that other bilateral capture mechanical fastening systems wherein the target tissue zones are penetrated by a fastener in sequential fashion are possible within the scope of the present invention. For instance, a semi-circular, oval, or spiral fastener may be advanced sequentially through target tissue zones 70 on each side of vertical interface 51 using a mechanism that imparts a rotational motion to the fastener, but without causing interdigitation or overlapping of skin across vertical interface 51. The mechanism may have means for creating a semi-circular, oval or spiral skive through which the fastener may be advanced, or the fastener itself may be formed from sufficiently rigid material and have a sharpened point so as to be capable of creating a skive as it passes through the skin. In another alternative embodiment providing a sequential bilateral capture motion, a fastener is provided having a cross-member connecting two legs wherein the legs are staggered so that when the fastener is advanced into the skin in a linear fashion, one of the legs precedes the other. In still another embodiment, two straight fasteners comprising a shaft portion with skin-engaging barbs are provided. These fasteners are oriented in opposite directions on either side of the vertical interface 51, and are sequentially advanced through respective skives by an applicator assembly allowing a reversible motion.

Figure 34:
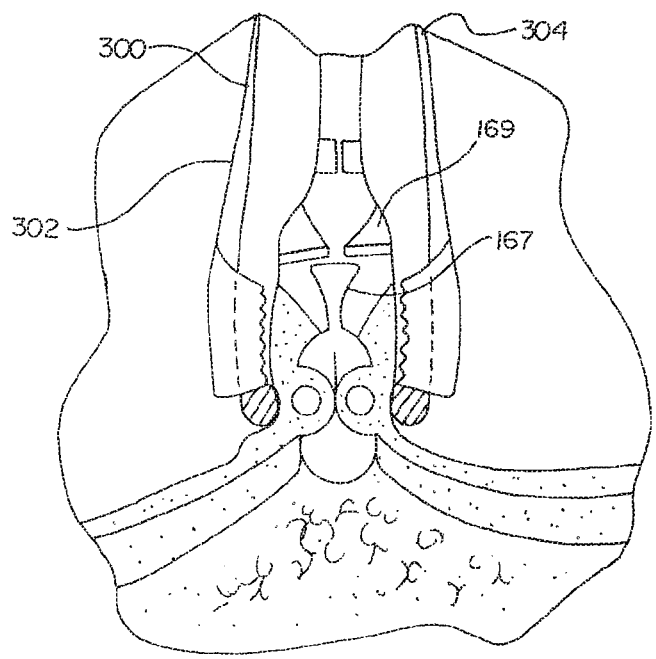
FIG. 34 is a longitudinal cross-sectional view of an alternative embodiment of the present invention showing operation of corresponding guiding features on the tissue manipulator and the applicator.

In one embodiment, as shown in FIG. 34, a tab or other similar guiding structure 167 projects from an exposed portion of anvil portion 140 to serve as a reference guide to locating the external surface of the skin against such guiding structures. Most preferably, this guiding structure 167 is adapted to mate with a corresponding pair of surface guiding features 169 on the internal surface of arms 302, 304 of the tissue manipulator assembly 300 so as to provide both a tactile and visual indication of the appropriate positioning of the applicator 100 and tissue manipulator 300 relative to the vertical interface 51 of the tissue opening 50. Preferably, the guiding structure 167 and guiding features 169 combine to force the applicator 100 to stay laterally centered about the vertical interface 51 and to stay properly positioned both horizontally and vertically. Alternatively, visual indicators and/or an exterior platform-like structure around the exterior of driving head 140 may be provided to assist the user in proper positioning of the applicator assembly 100 and the tissue manipulator assembly 300.

Figure 35:
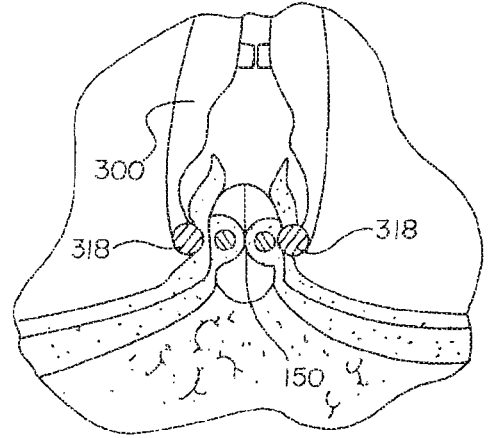
FIG. 35 is a longitudinal cross-sectional view of an alternative embodiment of the present invention showing ball tip ends on the tissue manipulator and corresponding semi-spherical areas on the applicator.
Figure 36:
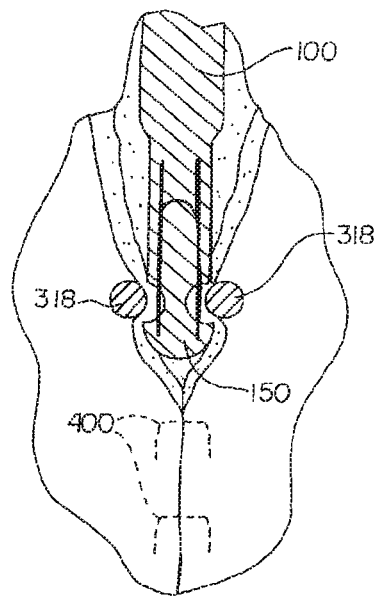
FIG. 36 is a top cross-sectional view of the alternative embodiment shown in FIG. 35.

FIGS. 35 and 36 show an alternate embodiment of applicator assembly 100 and tissue manipulator assembly 300 in which both manipulator surfaces 318 and concave areas 150 are semi-spherically shaped to provide guiding structure in both horizontal and vertical orientations as the tissue is compressed by the tissue manipulator 300 into the applicator 100. In this embodiment, there are no inward projections 320 shown for capturing the tissue as the application of pressure to the ball-like tips 318 provides both the capture and compression forces imparted to the tissue. Areas 150 on the applicator 100 are semi-spherical in shape to mate in more than one orientation with the ball tips 318, rather than being merely concave to align the tissue in a single orientation.

Figure 37:
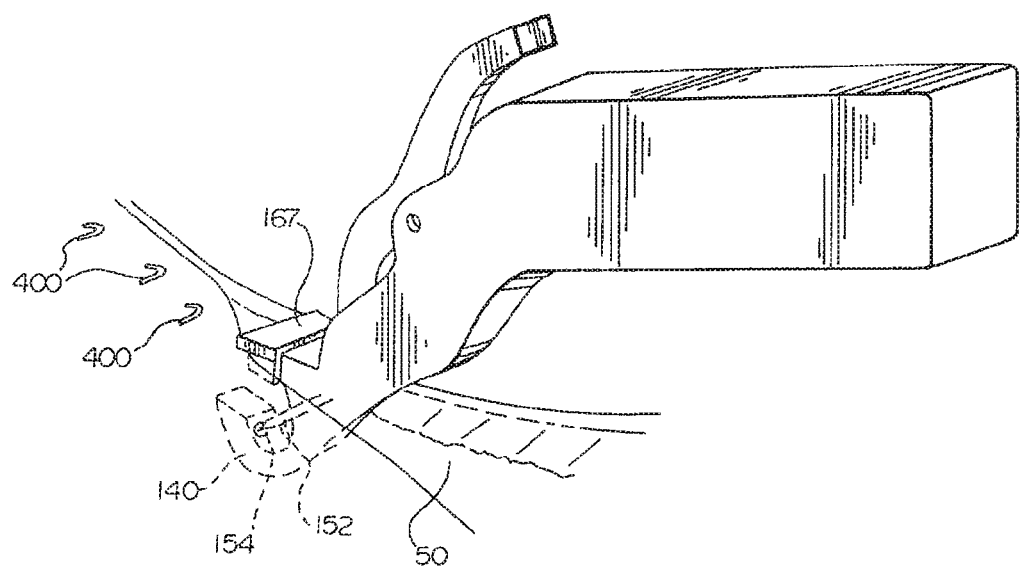
FIG. 37 is an isometric view of an alternate embodiment of the applicator assembly in which the fasteners are inserted obliquely into the tissue.

FIG. 37 shows another alternate embodiment of applicator assembly 100 in which the fasteners 400 are inserted obliquely into the tissue along the vertical interface 51. In this embodiment, the penetrating needles 152, 154 are oriented obliquely downward relative to the horizontal and the distance d1 on the driving head 140 is reduced. An upper projection 167 extends on top of the vertical interface 51 of the opening 50 to serve as a guide and the aperture 141 between upper projection 167 and the driving head 140 is positioned to require less rotational movement of the applicator assembly 100 in the plane of the vertical interface 51 when the tissue is being positioned in the driving head 140 or the applicator assembly 100 is being positioned for insertion of a subsequent fastener 400. One advantage of the oblique orientation of the fasteners 400 along the vertical interface 51 of opening 50 is that the effective spacing between backing members 408 of adjacent fasteners 400 is reduced, thereby affording the opportunity to increase the resulting holding pressure that can be applied across the vertical interface 51 to resist tearing by being able to insert more fasteners per longitudinal distance of the opening 50.

Figure 38:
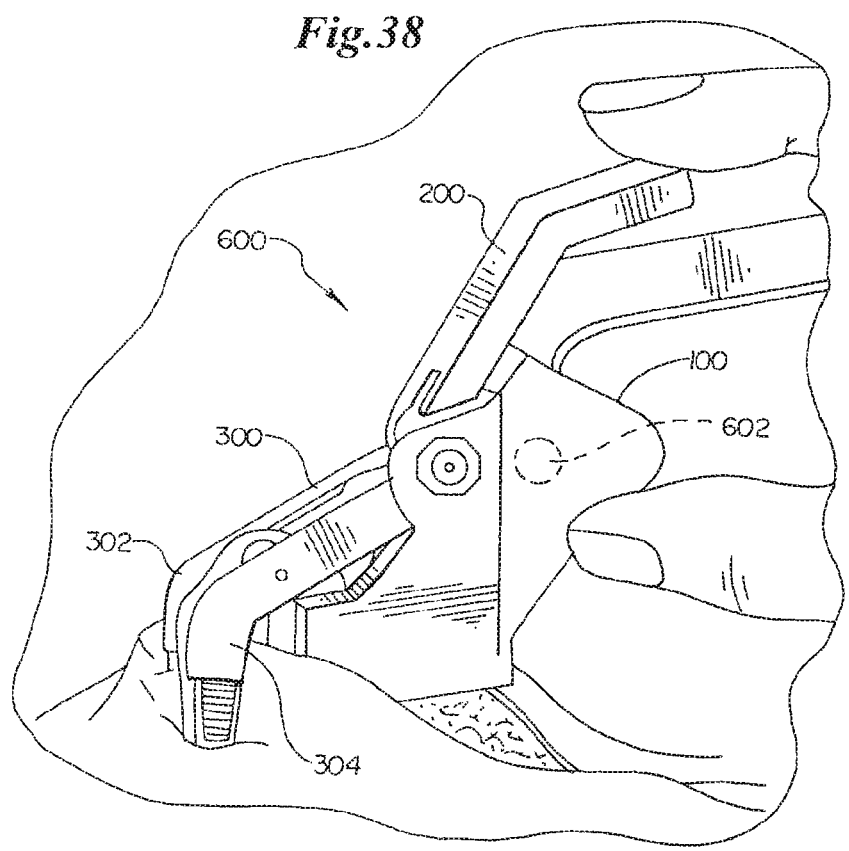
FIG. 38 is an isometric view of an alternate embodiment of the present invention in which the tissue manipulator and the applicator assembly are incorporated in a single handheld instrument.

FIG. 38 shows another embodiment of the present invention in which the tissue manipulator 300 and the applicator assembly 100 are integrated together into a single handheld surgical instrument 600. In this embodiment, a manual trigger 200 is used to activate first the lateral compression operation of the arms 302, 304 of the tissue manipulator assembly 300 and then is further depressed to engage the delivery mechanism 128. A force translation mechanism 602 inside the handle 110 in the form of a cam, wedge or similar arrangement is first engaged by the depression of the trigger 200. Further depression of trigger 200 then causes delivery mechanism 128 to be actuated. It will be appreciated that a single handheld surgical instrument 600 integrating the structures of both the applicator assembly 100 and the tissue manipulator assembly 300 could be arranged and operated in a number of ways. For example, two trigger actuators could be used instead of one two-stage actuator. Instead of arranging the tissue manipulator assembly 300 and the applicator assembly 100 inline in the same orientation, the two assemblies 300 and 100 could be arranged to face each other in the longitudinal orientation.

An alternative embodiment of a hand-held surgical instrument 700 using a top-down approach, as opposed to previously disclosed bottom-up embodiments, is depicted in FIGS. 40, 41, 42, 43, and 44. Hand-held surgical instrument 700 comprises a handle assembly 702, a tissue manipulator assembly 704 and an applicator assembly 706. Handle assembly 702 has a proximal end 708 and a distal end 710. Handle assembly 702 further comprises a gripping portion 712 and a mounting portion 714. Handle assembly 702 preferably is constructed using a first handle body 716 and a second handle body 718. First handle body 716 includes a pair of hollow projections 720*a*, 720*b*. Second handle body 718 includes a pair of through bores 722*a*, 722*b* positioned to align with hollow projection 720*a*, 720*b*. In addition, first handle body 716 includes a bore 724 that aligns with a throughbore 725 located on second handle body 718. First handle body 716 also includes another bore 726 aligned with a throughbore 727 on second handle body 718. First handle body 716 and second handle body 718 are assembled into handle assembly 702 using fastening means 721, most typically screws. Fastening means 727 are used to engage first handle body 716 and second handle body 718 at hollow projection 720a and throughbore 722a, hollow projection 720b and throughbore 722b and at bore 726 and throughbore 727. Both first handle body 716 and second handle body 718 include a mounting bore 728 presented within a mounting recess 730. Mounting bore 728 and mounting recess 730 accommodate a spring assembly 731. Located at proximal end 708 of both first handle body 716 and second handle body 718 is a pair of projections 732a, 732b. Projections 732a and 732b include projection bores 734a and 734b. Both first handle body 716 and second handle body 718 include an external mounting surface 740 including a mounting bore 742 and a mounting pin 743.

Tissue manipulator assembly 704 in this embodiment preferably comprises a trigger 750 having a biasing end 752 and a mounting end 754. Mounting end 754 includes an attachment block 756. Attachment block 756 includes an attachment surface 758 having a cylindrical groove 760. Attachment block 756 further comprises an attachment recess 762. A notch 763 is also present within attachment block 756. A pair of opposed attachment walls 764a, 764b define attachment recess 762 along with attachment surface 758. A pair of opposed posts 766a, 766b are mounted on attachment walls 764a, 764b. Also present on the exterior of attachment walls 764a, 764b are a pair of bores 768a and 768b.

Figure 45:
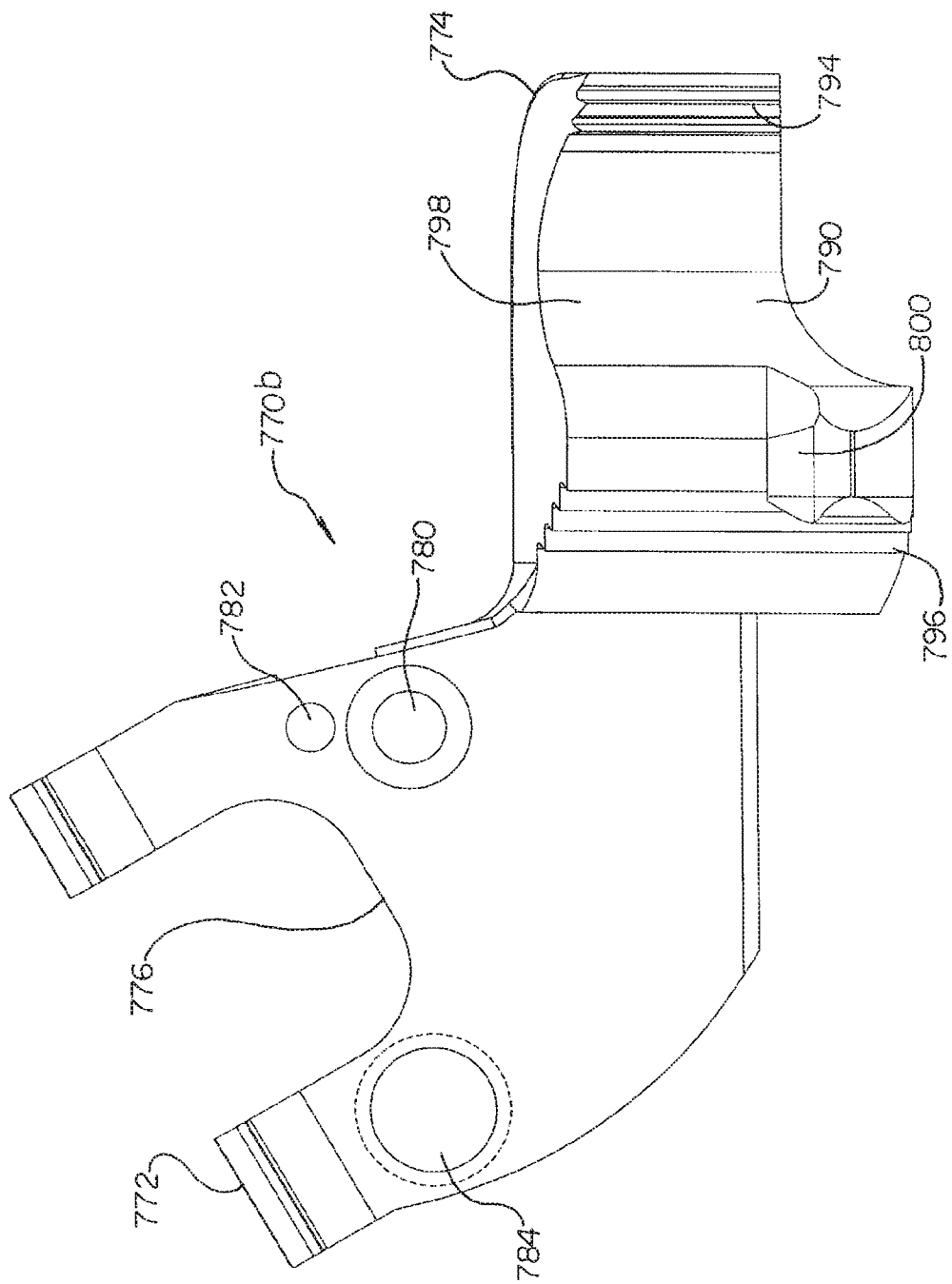
FIG. 45 is a side view of a tissue form.
Figure 46:
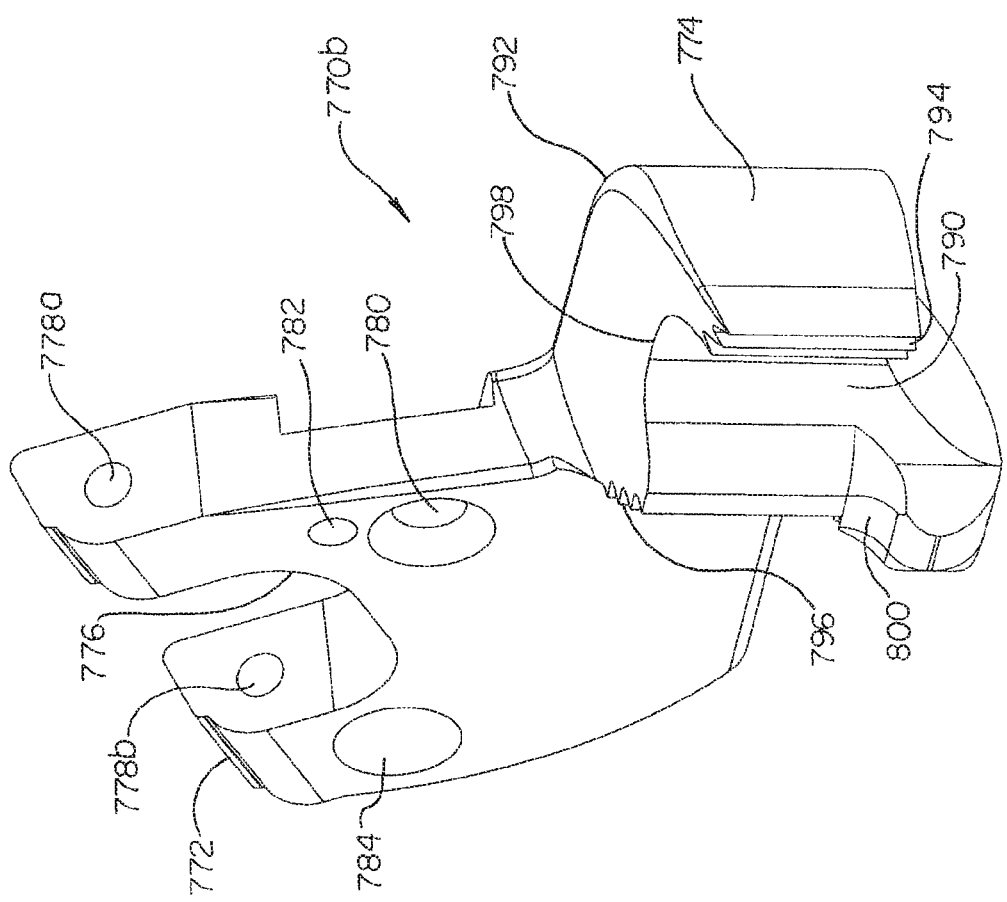
FIG. 46 is a perspective view of the tissue form shown in FIG. 45.

Tissue manipulator assembly 704 further includes a pair of opposed tissue forms 770a and 770b. Tissue form 770b is further depicted in FIGS. 45 and 46, though it is to be understood that tissue form 770a includes the same features as tissue form 770b but in a mirror-image arrangement. Tissue forms 770b includes an attachment end 772 and a gripping end 774. Attachment end 772 includes an opening 776 having a pair of opposed and aligned attachment bores 778, 778b. Tissue form 770b further includes a mounting bore 780, a post bore 782, and a limit bore 784. Limit screw 786 rotatably inserts into limit bore 784. On the exterior of tissue forms 770a, 770b is located a guide projection 788. Grasping end 774 is defined by an interior surface 790 and an exterior surface 792. Interior surface 790 is further defined by a proximal jaw 794, a distal jaw 796, an arcuate recess 798, and a bottom lip 800.

Figure 47:
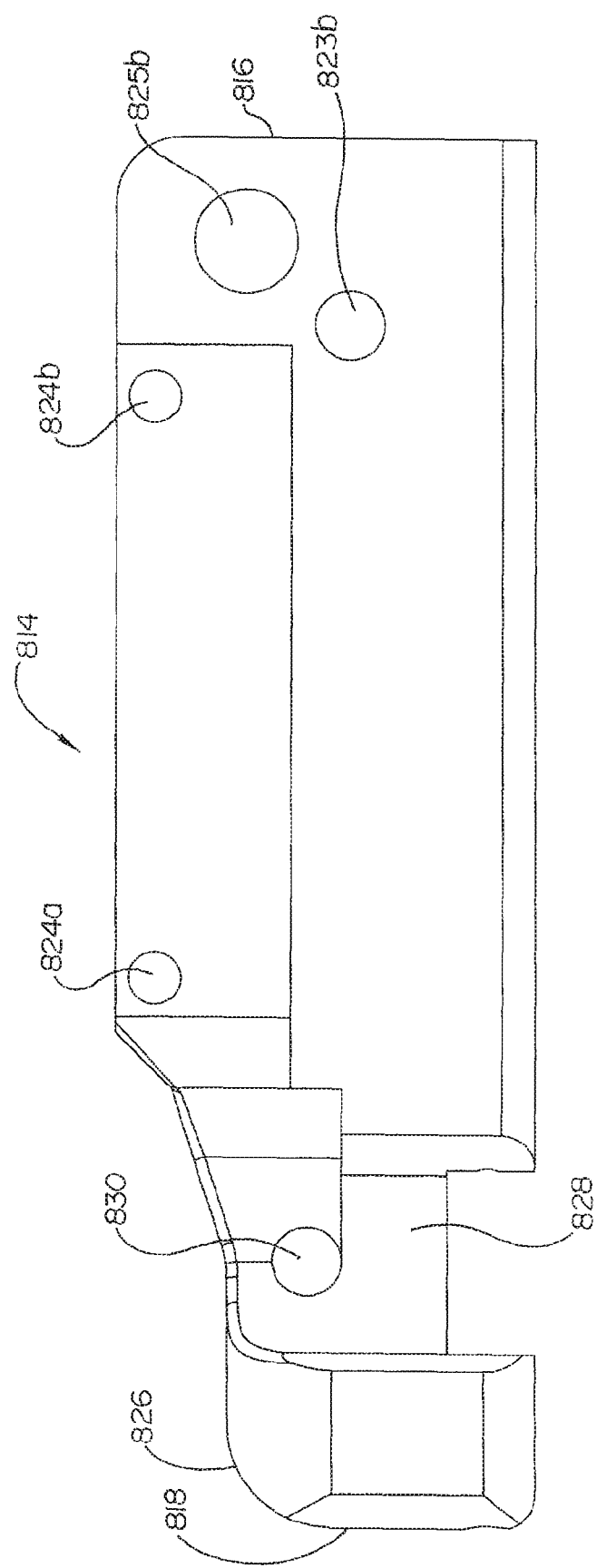
FIG. 47 is a side view of an insertion block.
Figure 48:
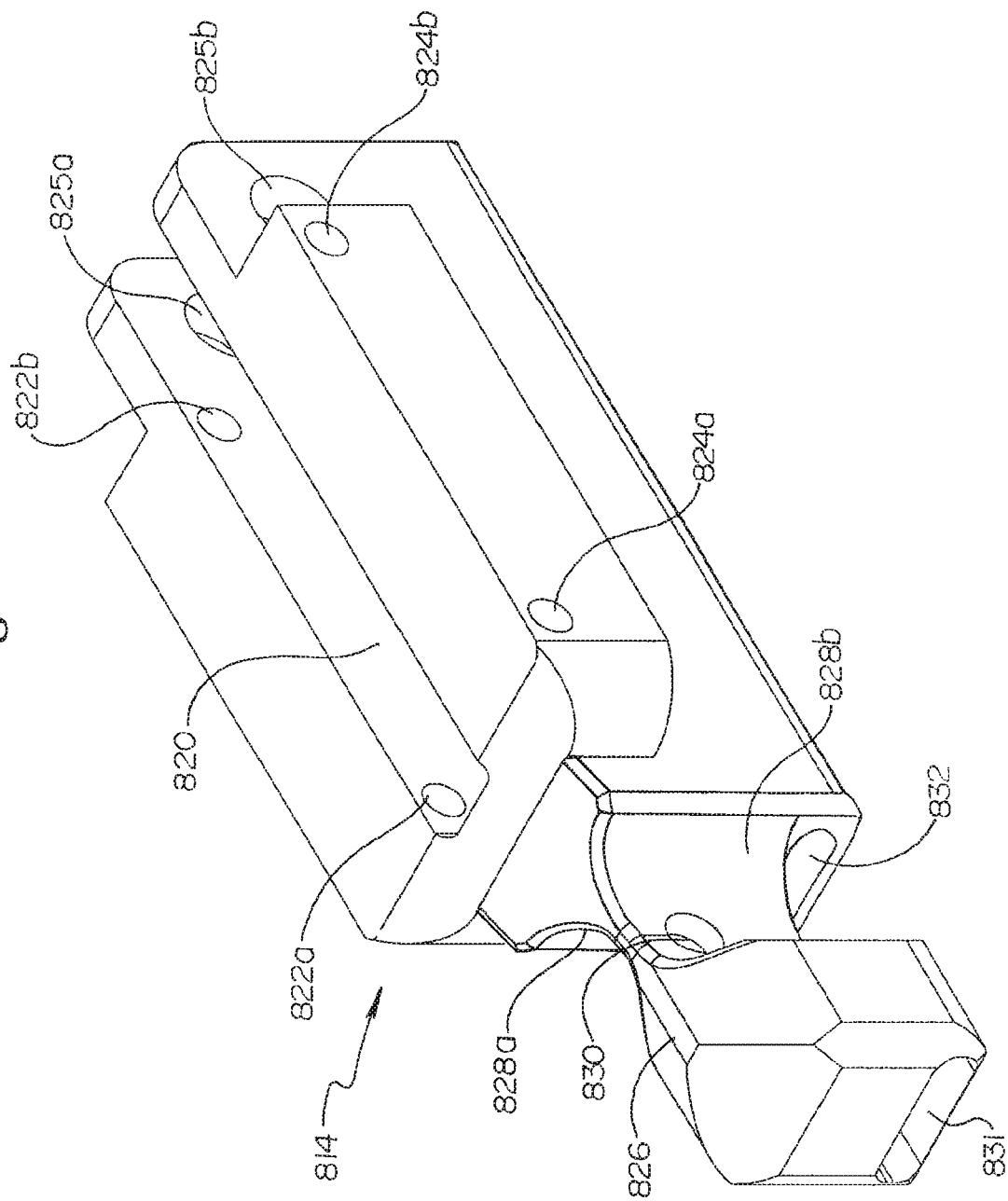
FIG. 48 is a perspective view of the insertion block shown in FIG. 47.
Figure 49:
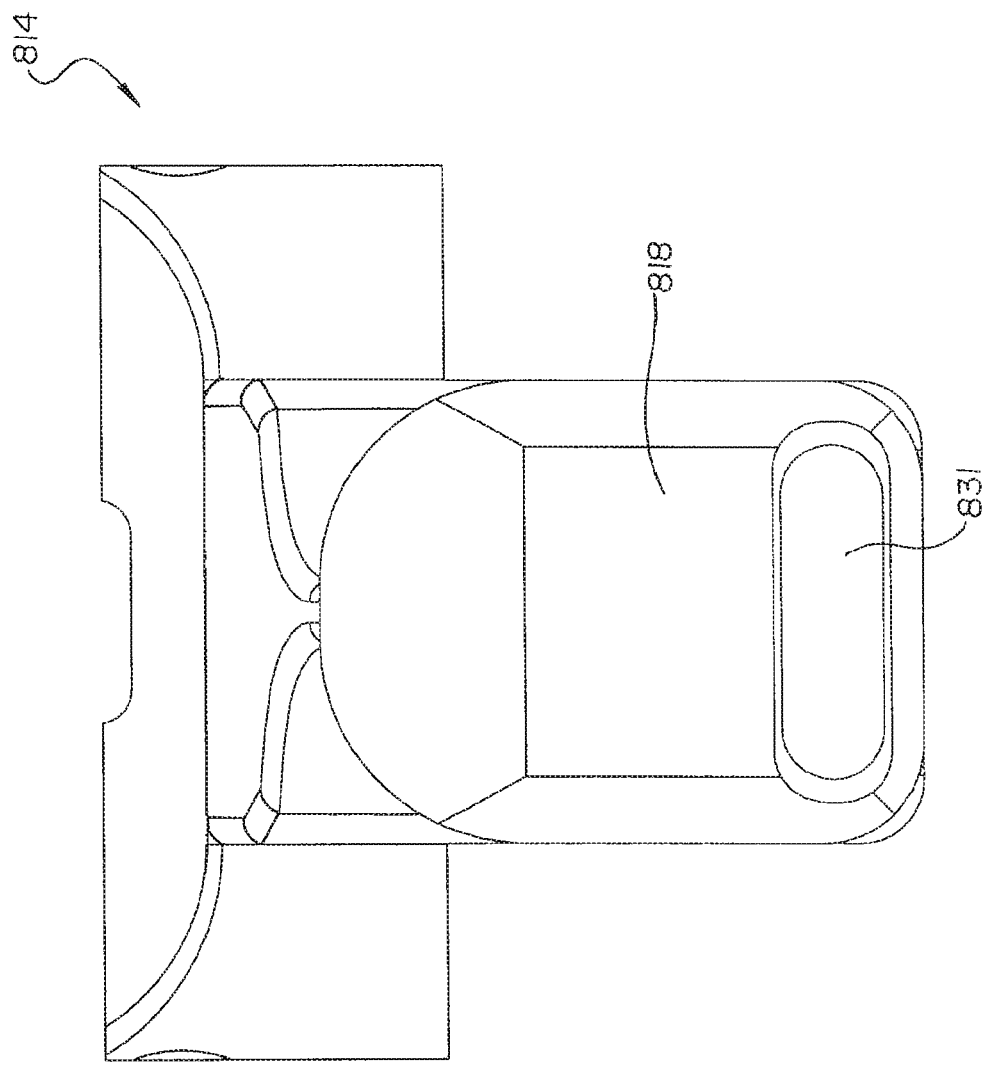
FIG. 49 is a front view of the insertion block shown in FIG. 47.

Applicator assembly 706 preferably includes an applicator trigger 802. Applicator trigger 802 includes a biasing end 804, a driving end 806, and a rotational through bore 808. A fulcrum member 810, depicted as a screw, slidingly inserts through throughbore 725, throughbore 808 and into bore 724. Fulcrum member 810 allows for rotational travel of applicator trigger 802 as well as providing additional fastening strength between first handle body 716 and second handle body 718. Driving end 806 includes a tip 812. Applicator assembly 706 further includes an insertion block 814 more clearly depicted in FIGS. 47, 48 and 49. Insertion block 814 includes an attachment end 816 and an insertion end 818. On the top of insertion block 814 is a hollow channel 820. A pair of attachment bores 822a, 822b on one side of hollow channel 820 are in alignment with a pair of attachment bores 824a, 824b present on the other side of hollow channel 820. Insertion block 814 also includes a pair of alignment bores 823a, 823b. Finally, insertion block 814 includes another pair of post bores 825a, 825b to accommodate a rotation post 827. Insertion end 818 is defined by an insertion head 826. Present on either side of insertion head 826 is an arcuate capture zone 828a, 828b. Within both capture zones 828a, 828b is an alignment indicator 830. The alignment indicator could include a bore or horizontal ledge. An insertion cavity 831 and a delivery cavity 832 define a continual opening extending from attachment end 816 to insertion end 818. An attachment slide 833 is dimensioned to fit within insertion cavity 831 and delivery cavity 832. Attachment slide 833 includes an attachment cavity 834 defined by a pair of cavity walls 836a, 836b. An insertion slide 838 is also dimensioned to fit within insertion cavity 831 and delivery cavity 832. Insertion slide 838 comprises a pair of piercing members 840a, 840b. Piercing members 840a, 840b each include an internal arcuate section 842. Piercing members 840a, 840b are connected via a backspan 844.

Figure 50:
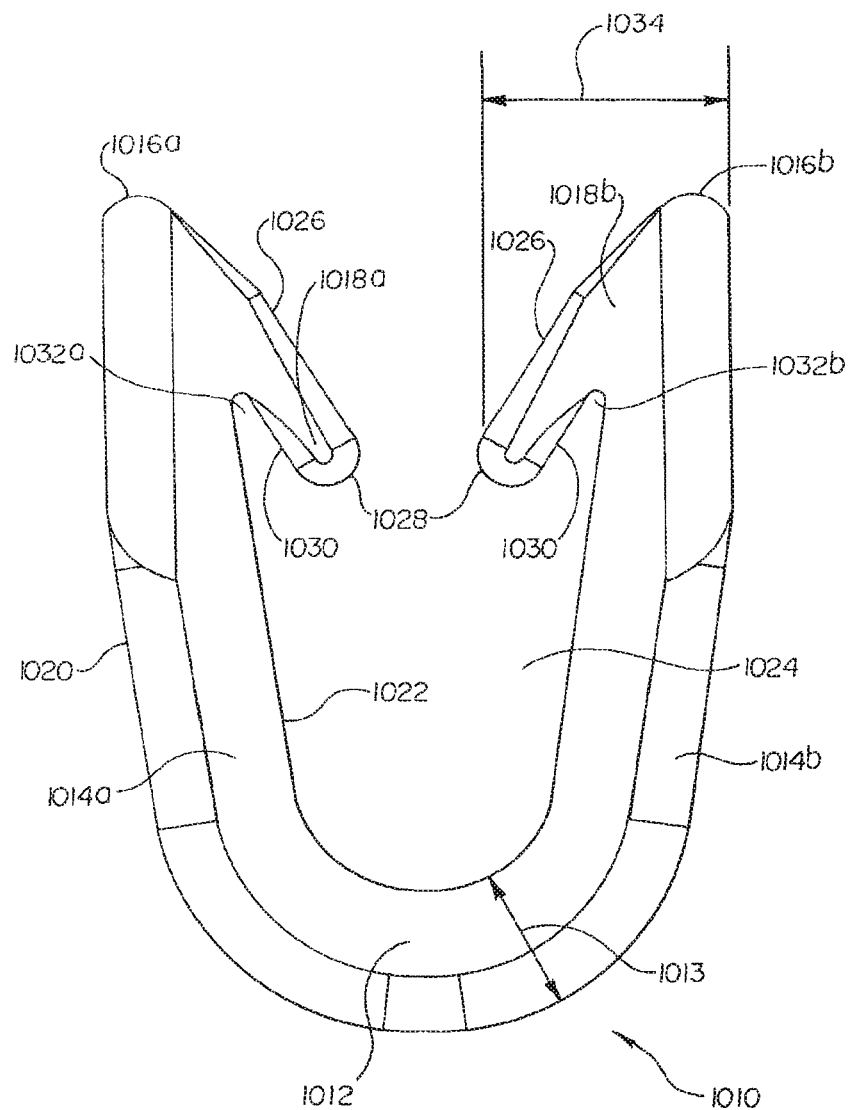
FIG. 50 is a top view of an alternative embodiment of a surgical fastener.
Figure 51:
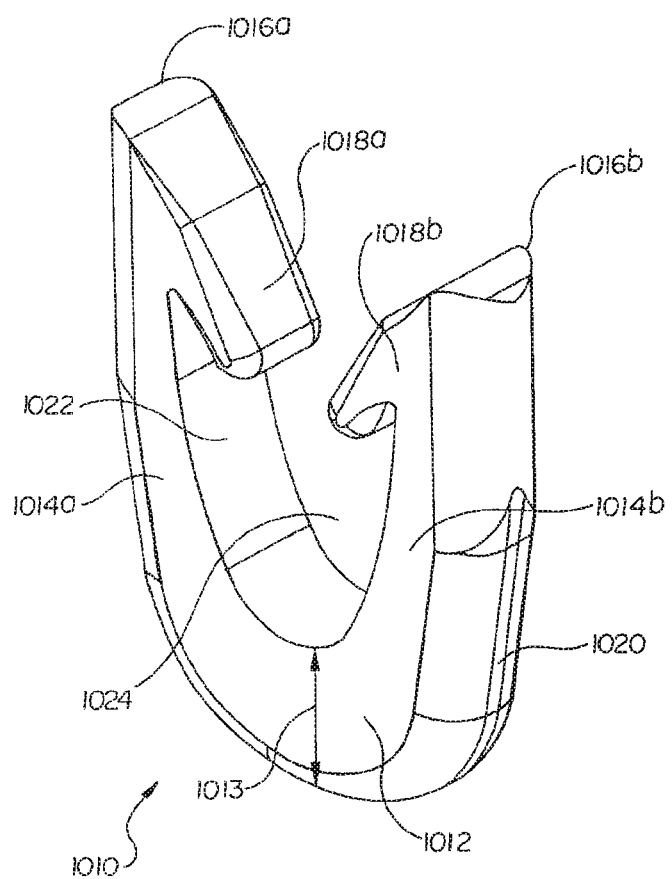
FIG. 51 is a perspective view of an alternative embodiment of a surgical fastener.
Figure 52:
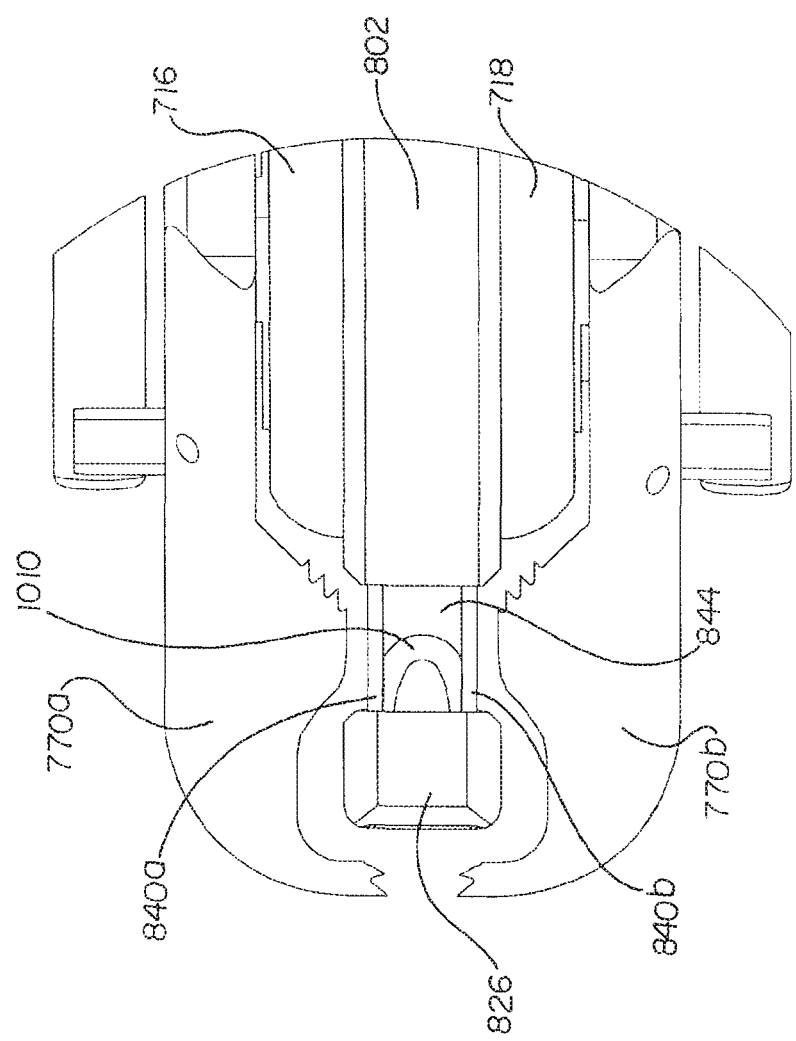
FIG. 52 is a top view of the handheld surgical fastener of FIG. 40 loaded with a surgical fastener.

Surgical instrument 700, as described is a single shot design in which a single bioabsorbable fastener 1010, as depicted in FIGS. 50 and 51, and as further described in concurrently filed U.S. Patent Application entitled, "Dynamic Bioabsorbable Fastener For Use In Wound Closure," filed Jun. 25, 2003, which is commonly assigned to the assignee of the present application and is hereby incorporated by reference in its entirety. Fastener 1010, as shown in FIG. 50, comprises a backspan 1012 operably connecting a pair of arms 1014a, 1014b. As depicted, fastener 1010 has a diameter 1013 that is consistent throughout backspan 1012 and arms 1014a, 1014b. Arms 1014a, 1014b each preferably include a rounded tip 1016a, 1016b connected to an internally projecting cleat 1018a, 1018b. Fastener 1010 includes an exterior surface 1020 and an interior surface 1022. Interior surface 1022 as defined by backspan 1012, arms 1014a, 1014b and cleats 1018a, 1018b defines an internal tissue capture zone 1024. Each cleat 1018a, 1018b includes an insertion face 1026, a cleat tip 1028 and a rear surface 1030. Rear surface 1030 intersects arms 1014a, 1014b defining a capture area 1032a, 1032b. Each arm 1014a, 1014b of fastener 1010 has an insertion width 1034 which is defined across the widest width across arm 1014a and cleat 1018a or arms 1014b and cleat 1018b. Generally, fastener 1010 is dimensioned to fit between piercing member 840a, 840b and backspan 844. Fastener 1010 is positioned such that the arms 1014a, 1014b reside within the internal arcuate sections 842 as depicted in FIG. 52. In an alternative embodiment of fastener 1010 depicted in FIG. 51, the diameter 1013 can be proportioned throughout the backspan 1012 and arms 1014a, 1014b to provide desired strength levels without affecting the interaction of fastener 1010 and piercing members 840a, 840b.

Preferably, surgical instrument 700 is used in a through-and-through bilateral tissue fastening technique 860 for bilateral fastening of dermal tissue. The through-and-through bilateral fastening technique 860 is depicted in FIGS. 57, 58, 59, 60, 61, 62 and 63. While the through-and-through procedure is described with reference to closure of a skin wound, one of skill in the art will recognize that the through-and-through procedure can be effectively applied in other applications involving closure of tissue openings such as fascia, internal organs, vessels and vasculature, or with tissue attachments including skin grafting, bladder and other anatomic tissues.

Figure 53:
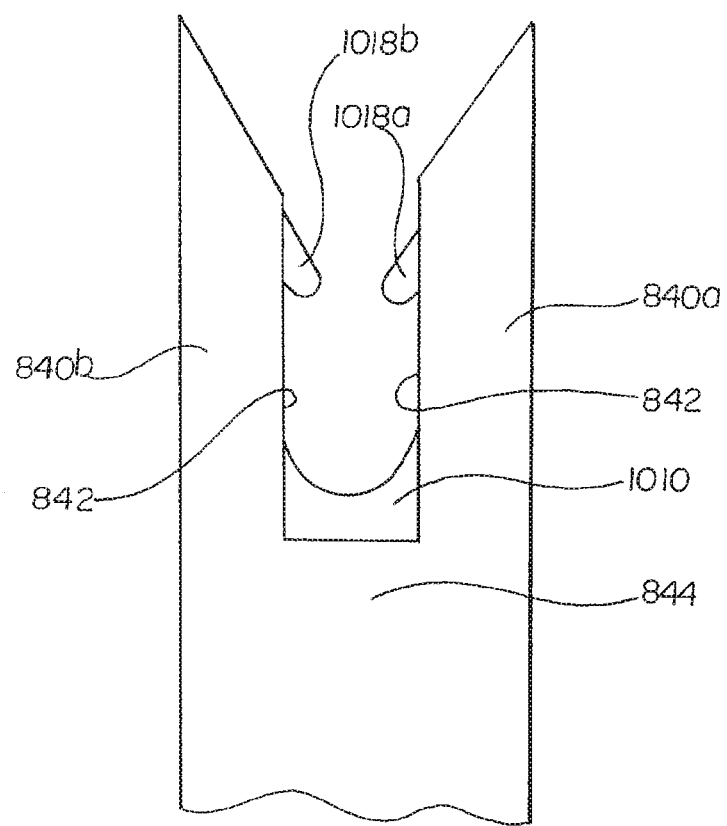
FIG. 53 is a top view of a pair of piercing members and a backspan loaded with a surgical fastener.
Figure 54:
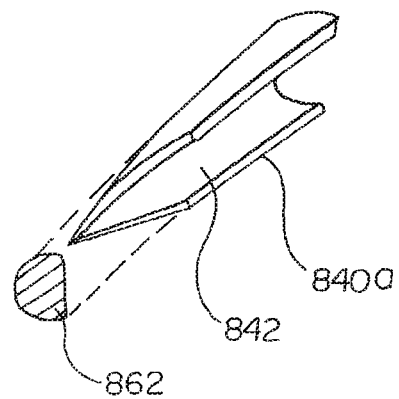
FIG. 54 is a perspective view of a piercing member.
Figure 55:
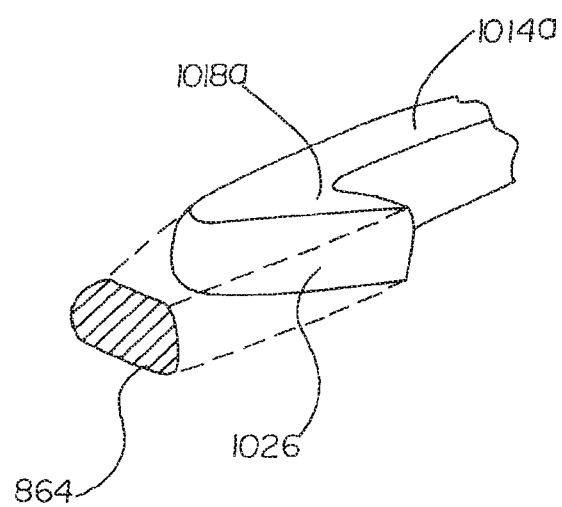
FIG. 55 is a perspective view of an arm tip.

Generally, a first step of the through-and-through bilateral fastening technique 860 is to load fastener 1010 between piercing member 840a, 840b and backspan 844. As depicted in FIG. 53, fastener 1010 resides snugly within internal arcuate sections 842. As shown in FIG. 54, piercing member 840a, and corresponding piercing member 840b, have a piercing cross-section 862. Similarly, cleat 1018a, and corresponding cleat 1018b, have a cleat cross-section 864 as shown in FIG. 55. Fastener 1010 is specifically designed such that the insertion width 1034 exceeds the piercing cross-section 862. As such, cleats 1018a, 1018b will protrude inwardly from piercing members 840a, 840b, as illustrated in FIG. 53.

Figure 56:
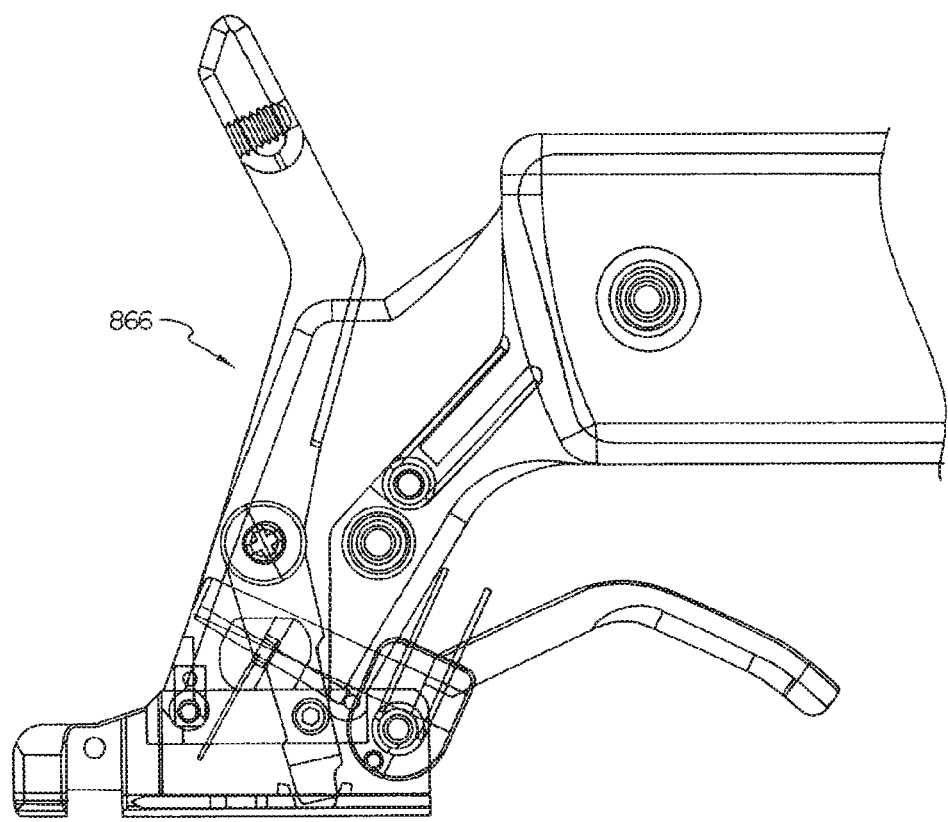
FIG. 56 is a side view of the handheld surgical instrument of FIG. 40.
Figure 57:
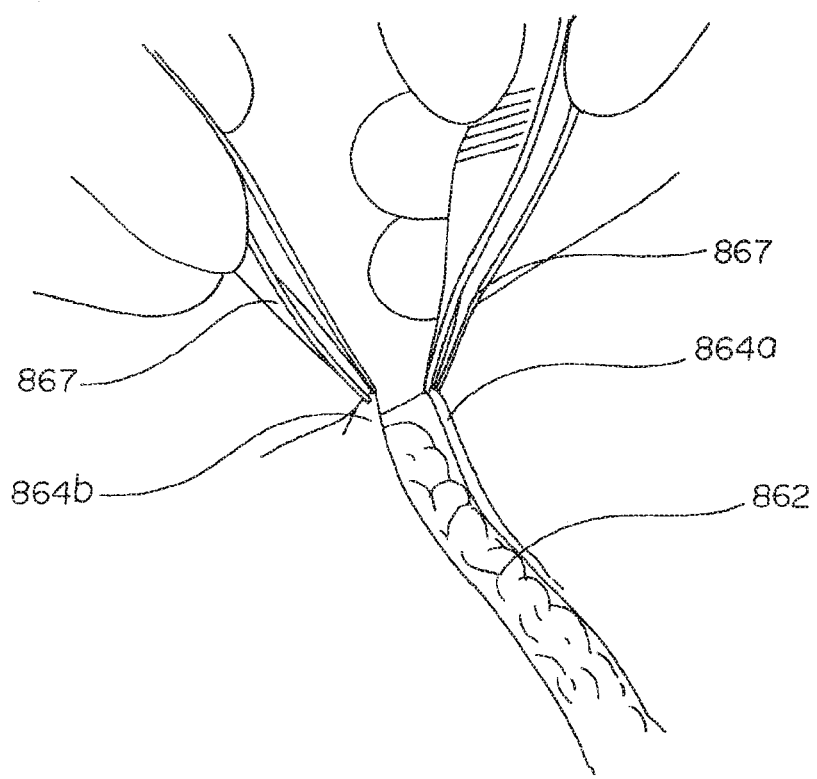
FIG. 57 is a perspective view showing a tissue positioning step of the through-and-through bilateral fastening technique of the present invention.
Figure 58:
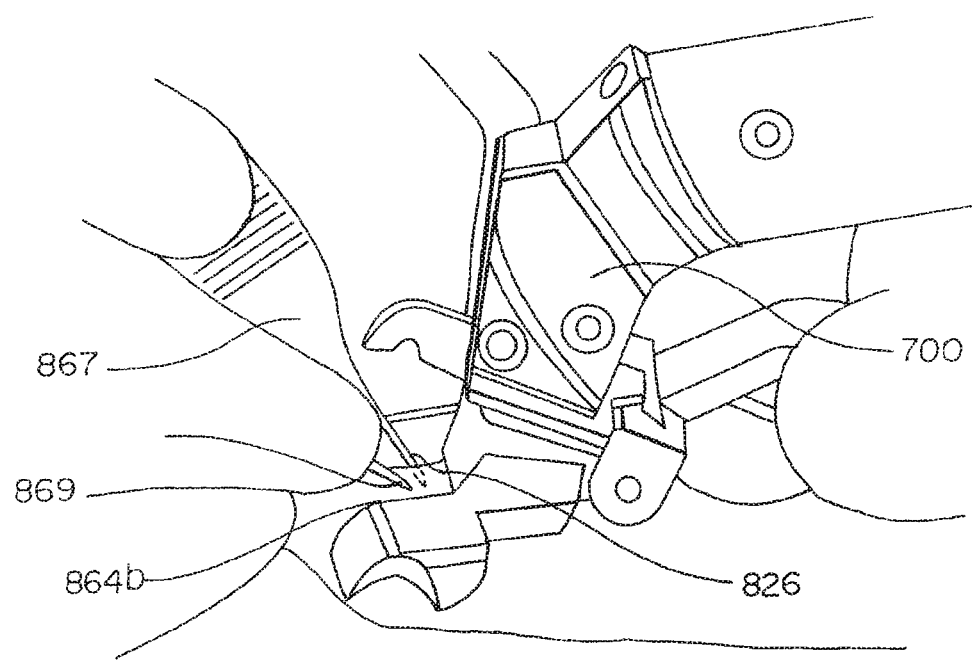
FIG. 58 is a perspective view showing a tissue positioning step of the through-and-through bilateral fastening technique of the present invention.
Figure 59:
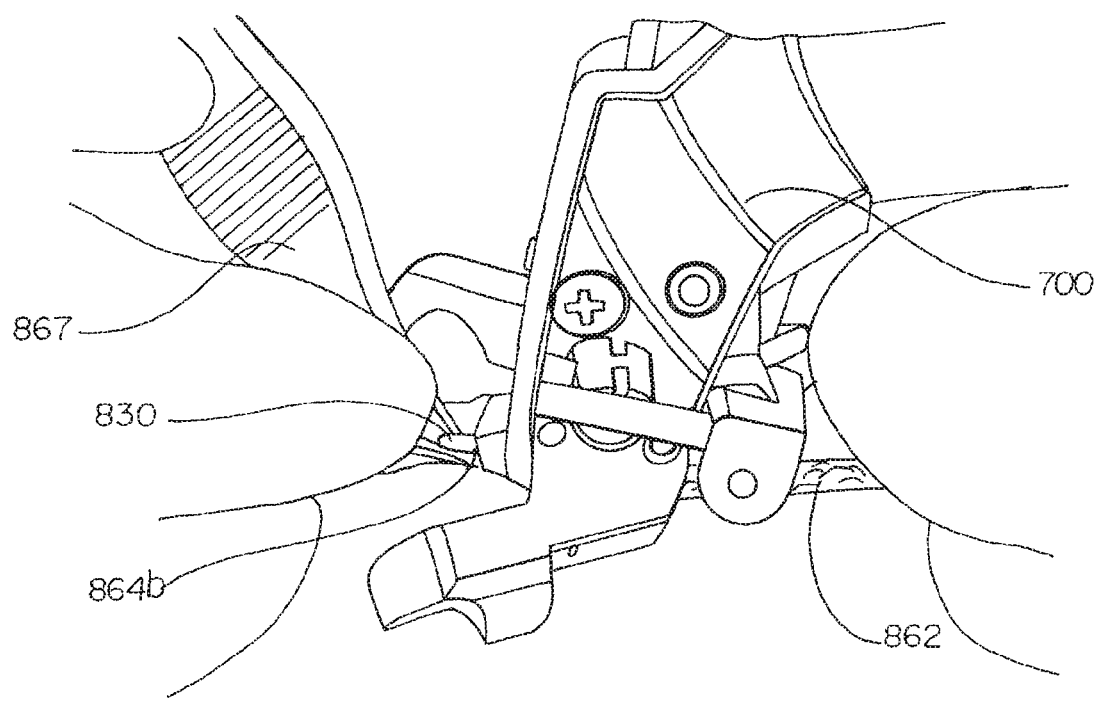
FIG. 59 is a perspective view showing a tissue positioning step of the through-and-through bilateral fastening technique of the present invention.

Once surgical instrument 700 has been loaded with fastener 1010, insertion head 826 is inserted into and positioned within a tissue wound 862 having a pair of opposed sides 864a, 864b. Surgical instrument 700 should be in an open disposition 866, as shown in FIG. 56, in which the tissue forms 770a, 770b are substantially spaced apart from insertion head 826. Using a grasping device 867, most typically being a standard surgical forceps, as depicted in FIG. 57, a medical professional grasps the opposed sides 864a, 864b, and places the opposed side 864a, 864b in proximity to insertion head 826 in an everted disposition 869, as shown in FIG. 58. At this point, opposed side 864a is positioned within capture zone 828a while opposed side 864b is positioned within capture zone 828b. Using alignment indicator 830, a medical professional can properly position opposed sides 864a, 864b with respect to the vertical height of capture zones 828a, 828b as shown in FIG. 59. When properly positioned, the dermal layer 56 of opposed sides 864a, 864b is in contact with the surface of capture zones 828a, 828b.

Figure 60:
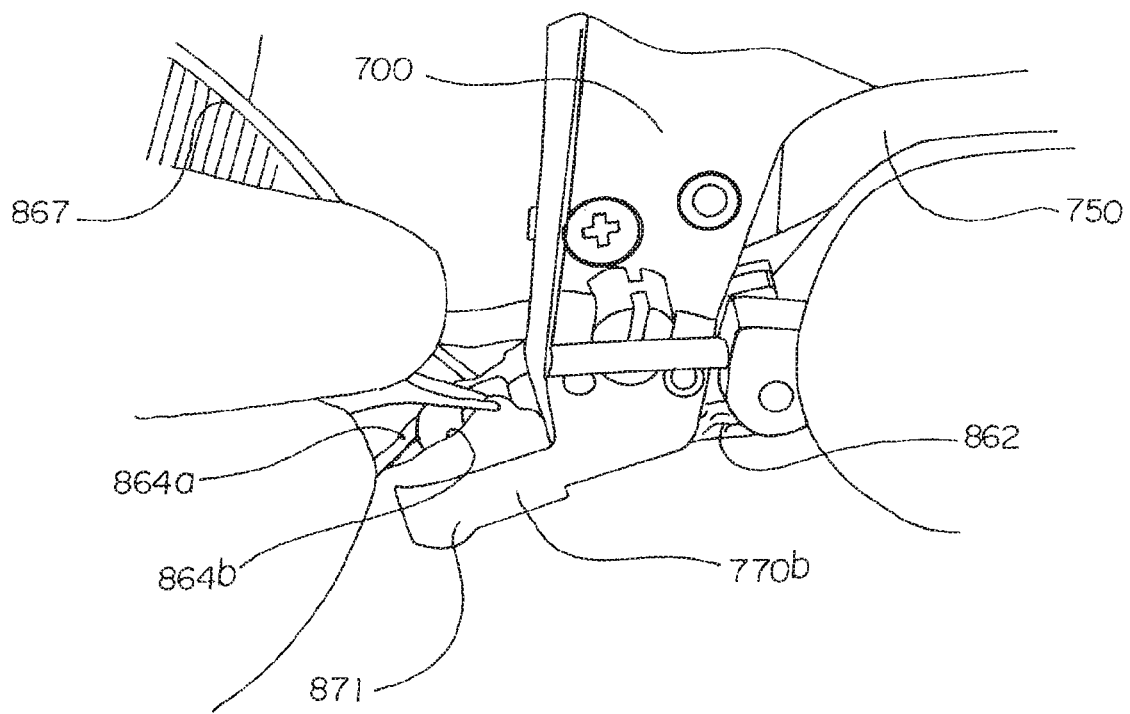
FIG. 60 is a perspective view showing a tissue capture and forming step of the through-and-through bilateral fastening technique of the present invention.
Figure 61:
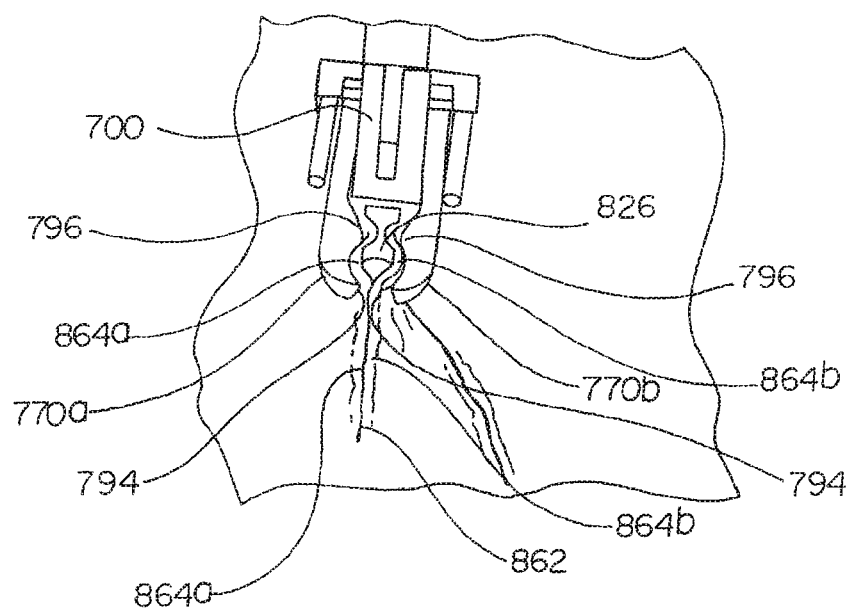
FIG. 61 is a perspective view showing a tissue capture and forming step of the through-and-through bilateral fastening technique of the present invention.

After opposed sides 864a, 864b are properly positioned within capture zones 828a, 828b, the medical professional biases trigger 750 in an upward direction causing tissue forms 770a, 770b to simultaneously close upon opposing sides 864a, 864b within tissue zones 828a, 828b, as shown in FIG. 60. Surgical instrument 700 is referred to being in a 871 capture disposition 866. Capture disposition 871 is accomplished by directing trigger 750 in an upward direction causing trigger 750 to rotate about rotation post 827. Rotation post 827 operably joins trigger 750 and insertion head 814 in conjunction with post bores 825a, 825b, cylindrical groove 760 and bores 768a, 768b. As trigger 750 is biased upward, mounting end 754 travels in a downward arc causing opposed posts 766a, 766b to move downward and contact guide projection 788 on tissue forms 770a, 770b. This causes tissue forms 770a, 770b to rotate in a downward direction around mounting pin 743 such that the interior surface 790 of tissue forms 770a, 770b is in close proximity to capture zones 828a, 828b. As tissue forms 770a, 770b rotate downwardly, the bottom lip 800 on interior surface 790 prevents tissue, especially the elastic dermal layer 56, from escaping out the bottom of capture zones 828a, 828b. Due to precise dimensioning of insertion head 826 and tissue forms 770a, 770b, the target tissue zone 70 as previously described, is presented within both opposing sides 864a, 864b. In addition, the combination of proximal jaw 794 and distal jaw 796 on tissue forms 770a, 770b, grasp and stretch opposed sides 864a, 864b causing opposed sides 864a, 864b to be held tightly between insertion head 826 and tissue forms 770a, 770b to further reduce the potential for perforating the epidermal layer 54 of opposed sides 864a, 864b, as depicted in FIG. 61.

Figure 62:
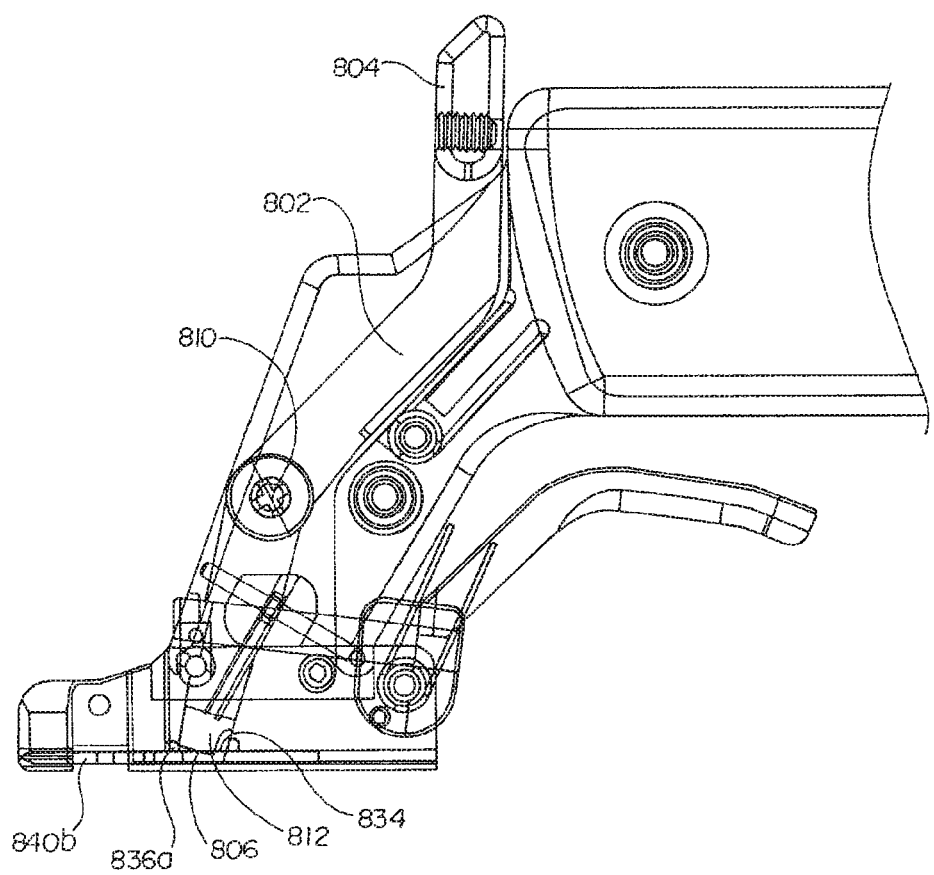
FIG. 62 is a side view of the handheld surgical instrument of FIG. 40.

Once the opposed sides 864a, 864b are captured within insertion head 826 and tissue forms 770a, 770b, the medical professional directs biasing end 804 of applicator trigger 802 in a distal direction as shown in FIG. 62. As biasing end 804 travels rearward, trigger 802 rotates about fulcrum member 810 causing tip 812 on driving end 806 to travel in a proximal direction. Tip 812, positioned within attachment cavity 834, contacts cavity wall 836a causing attachment slide 833 to move in a proximal direction through delivery cavity 832. Attachment slide 833 abuts insertion slide 838 causing insertion slide 838 to also move in a proximal direction through delivery cavity 832. As insertion slide 838 moves in a proximal direction, piercing members 840a, 840b are advanced sequentially out of delivery cavity 832, into capture zones 828a, 828b, into target tissue zones 70 of opposed sides 864a, 864b and into insertion cavity 831. As piercing members 840a, 840b are advanced proximally, fastener 1010 is simultaneously advanced out of delivery cavity 832, into capture zones 828a, 828b, into target tissue zones 70 of opposed sides 864a, 864b and into insertion cavity 831 as shown in FIG. 52. As previously described, insertion width 1034 exceeds the piercing cross-section 862. Consequently, the holes cut in the target tissue zone 70 by piercing members 840a, 840b must stretch to accommodate insertion width 1034. As cleats 1018a, 1018b are advanced into the holes cut in target tissue zone 70, the holes pierced by piercing member 840a, 840b in dermal layer 56 are forced to elastically stretch past the cleat tips 1028. The dermal layer 56 then rebounds and elastically snaps into capture areas 1032a, 1032b.

Figure 63:
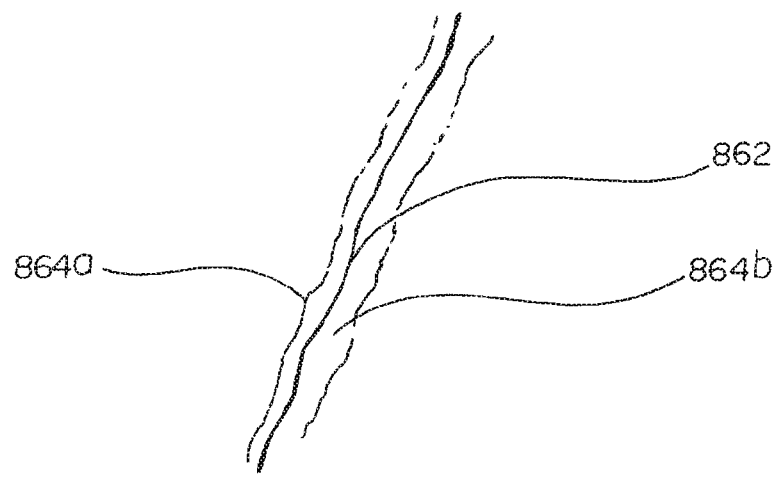
FIG. 63 is a perspective view of a wound closure following insertion of surgical fasteners using the through-and-through bilateral fastening technique of the present invention.
Figure 64:
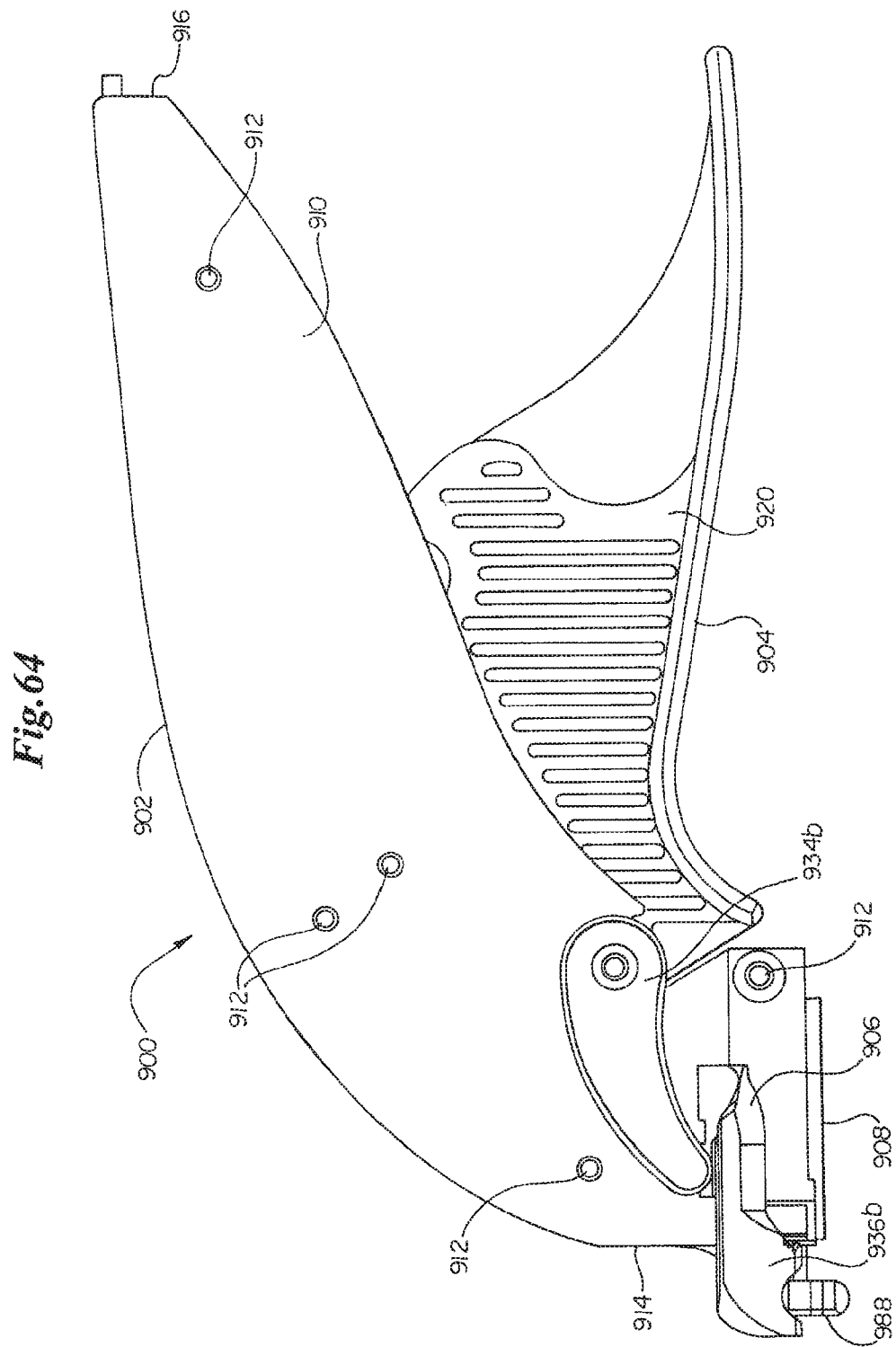
FIG. 64 is a side view of an alternative embodiment of the present invention in which a tissue manipulator assembly and an applicator assembly are incorporated into a single handheld surgical instrument having a multi-shot fastener insertion design.
Figure 65:
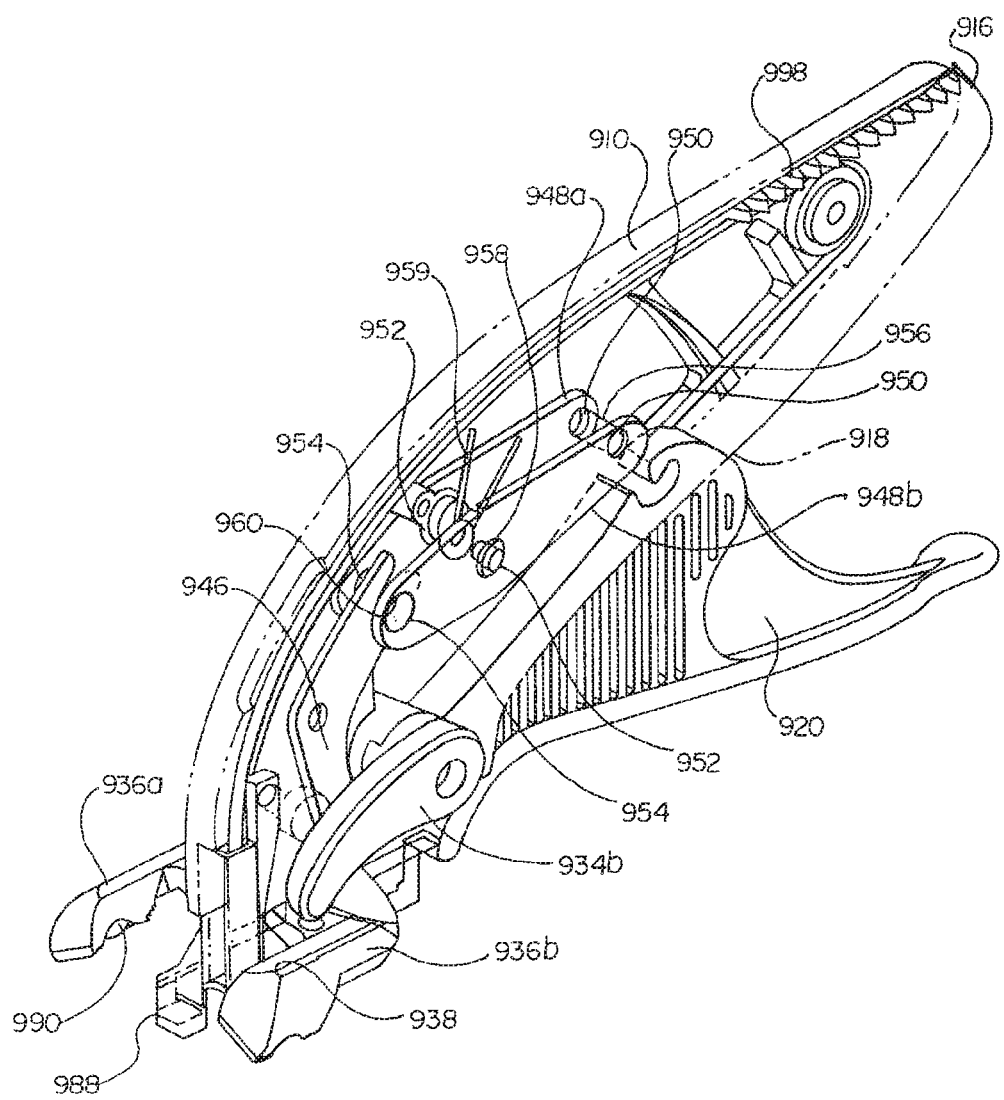
FIG. 65 is a sectional, perspective view of the handheld, multi-shot surgical instrument of FIG. 64.
Figure 66:
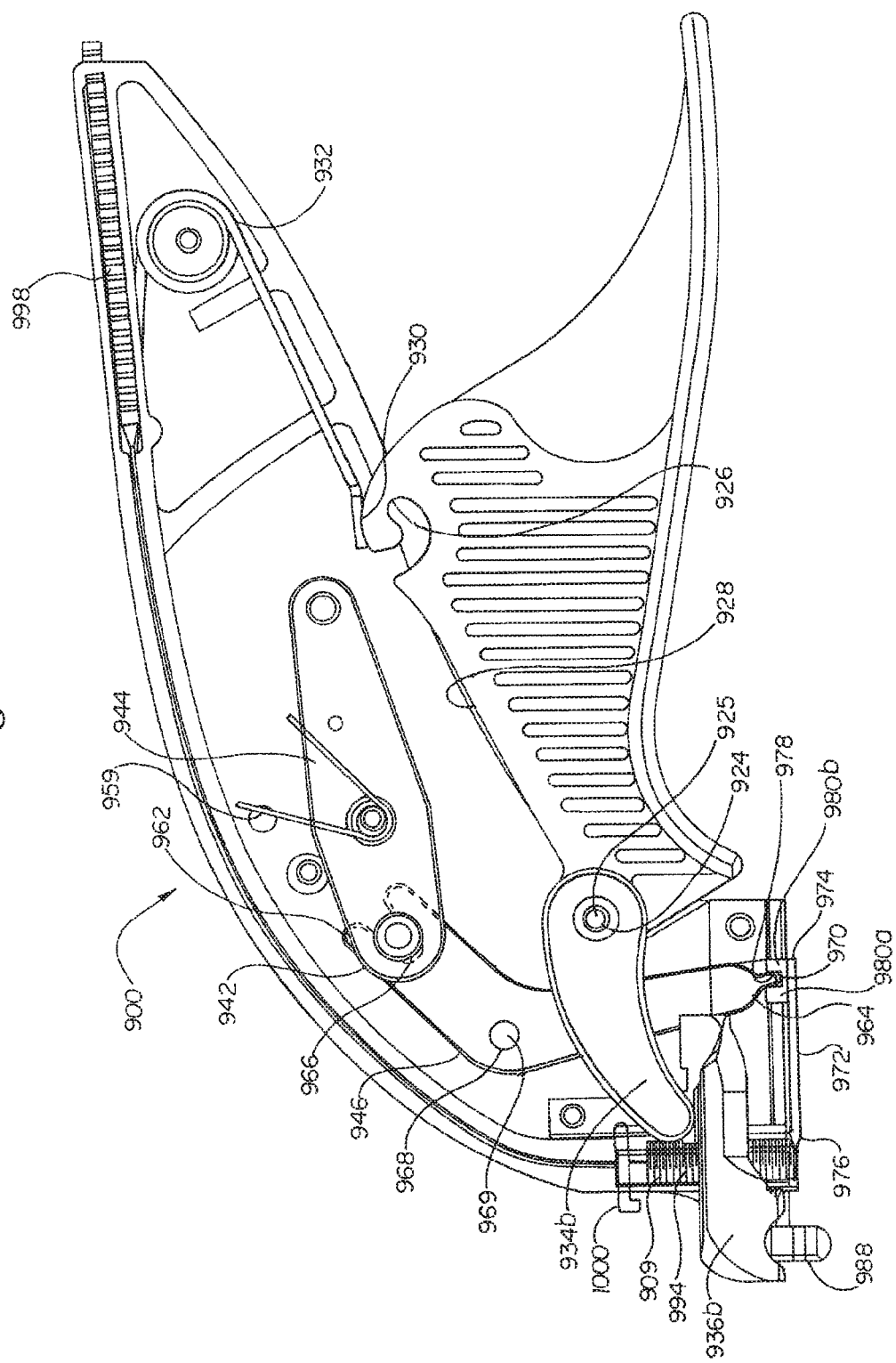
FIG. 66 is a sectional, side view of the handheld multi-shot surgical instrument of FIG. 64.
Figure 67:
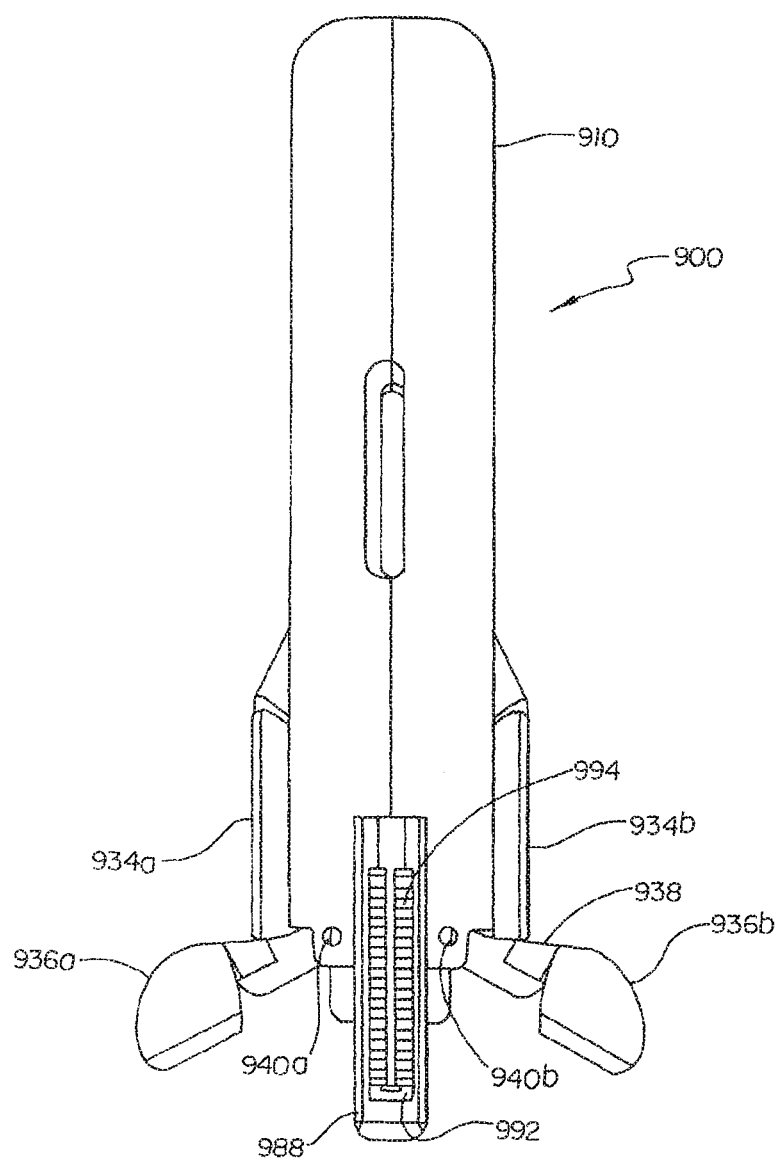
FIG. 67 is a front, partial section view of the handheld multi-shot surgical instrument of FIG. 64.

Using application assembly 706, the medical professional directs biasing end 804 of applicator trigger 802 in a proximal direction causing trigger 802 to rotate about fulcrum member 810 causing tip 812 on driving end 806 to travel in a distal direction. Tip 812, positioned within attachment cavity 834, contacts cavity wall 836b causing attachment slide 833 to move in a distal direction through delivery cavity 832. Attachment slide 833 causes insertion slide 838 to also move in a proximal direction such that piercing members 840a, 840b are sequentially withdrawn from insertion cavity 831, target tissue zones 70, capture zones 828a, 828b and into delivery cavity 832. However, fastener 1010 remains within target tissue zones 70 as cleats 1018a, 1018b, prevent fastener 1010 from being withdrawn due to captured dermal layer elastically retained within capture areas 1032a, 1032b. Fastener 1010 remains within tissue wound 862 such that backspan 1012 traverses the gap between opposed sides 864a, 864b with the dermal layers 56 forcibly approximated to promote the biological healing process. Once fastener 1010 has been placed, the medical professional directs trigger 750 in a downward direction causing tissue forms 770a, 770b to rotate upwardly and release opposed sides 864a, 864b such that surgical instrument 700 is back in open disposition 866. The through-and-through bilateral fastening technique 860 is typically repeated along the length of tissue wound 862 resulting in the closure of wound 862, as depicted in FIG. 63.

Another alternative embodiment of a handheld surgical instrument 900 is depicted in FIGS. 64-68. Handheld surgical instrument 900 comprises a body assembly 902, a trigger assembly 904, a tissue manipulation assembly 906, an applicator assembly 908, and a fastener assembly 909. Body assembly 902 comprises a molded housing 910 connected via a plurality of fastening members 912. Molded housing 910 includes a proximal end 914 and a distal end 916. Molded housing 910 further includes a bottom opening 918.

Trigger assembly 904 comprises a trigger 920, a manipulation bore 924, a ratchet member 925, an interface channel 926 and a top surface 928. Top surface 928 includes an upper engagement portion 930. Upper engagement portion 930 interfaces with a spring assembly 932.

Tissue manipulation assembly 906 comprises a pair of connecting arms 934a, 934b and a pair of tissue forms 936a, 936b. Tissue forms 936a, 936b include a grasping portion 937 substantially similar to tissue forms 770a, 770b, which have been previously described. On an exterior surface of tissue forms 936a, 936b is a molded guide ramp 938 performing the same function as guide projection 788, as previously described. Each tissue form 936a, 936b includes a pair of mounting bores 940a, 940b.

Applicator assembly 908 includes an advancing assembly 942 comprised of a rotation member 944 and a lever member 946. Rotation member 944 is comprised of a pair of opposed rotation elements 948a, 948b. Each rotation element 948a, 948b includes a distal bore 950, a fulcrum bore 952, and a proximal bore 954. Rotation elements 948a, 948b are then interconnected with a distal connector 956 through distal bores 950, a fulcrum connector 958 through fulcrum bores 952, and a proximal connector 960 mounted through proximal bores 954. Lever member 946 includes distal end 962 and a proximal end 964. A spring assembly 959 is mounted on fulcrum connector 958. Distal end 962 has a channel 966. Lever member 946 includes a fulcrum bore 968 having a fulcrum connector 969. Located at proximal end 964 is a connecting tip 970. Applicator assembly 908 further includes insertion slide 972. Insertion slide 972 comprises a distal end 974 and a proximal end 976. Located at the distal end 974 of insertion slide 972 is an attachment cavity 978 defined by a pair of attachment walls 980a, 980b. At the proximal end 976 of insertion slide 972 is a pair of opposed piercing members 982a, 982b. Piercing members 982a, 982b each include an internal arcuate section 984a, 984b. Piercing members 982a, 982b are operably joined at backspan member 986. Applicator assembly 908 further includes an insertion head 988. Insertion head 988 includes an arcuate capture zone 990. Throughout the length of insertion head 988 is an insertion cavity 992 dimensioned to accommodate the insertion slide 972.

Fastener assembly 909 in this embodiment comprises a fastener stack 994, consisting of a plurality of bioabsorbable fasteners 1010 previously depicted in FIGS. 50 and 51, a fastener housing 996, and a spring feed assembly 998. Fastener assembly 909 can further include a removable locking member 1000. Removable locking pin 1000 allows a surgical instrument 900 to be shipped fully assembled to facilitate ease of use by a physician. Preferably, removable locking pin 1000 prevents spring feed assembly 998 from applying force directly to fastener stack 994 during shipment or storage so that the bioabsorbable fasteners 1010 do not deform after prolonged exposure to the spring force.

Preferably, surgical instrument 900 is used with a through-and-through bilateral tissue fastening technique similar to that of surgical instrument 700 as previously described. One procedural difference being that surgical instrument 900 is a multi-shot design in which a plurality of fasteners 1010 come preloaded, thus eliminating any hand-loading of individual fasteners 1010. Another procedural difference being that surgical instrument 900 includes trigger assembly 904 which incorporates a two-stage mechanism sequentially operating both the tissue manipulation assembly 906 and applicator assembly 908.

With respect to grasping tissue with tissue manipulation assembly 906, the medical profession squeezes body assembly 902 and trigger assembly 904 causing trigger 920 rotate about ratchet member 925. As trigger 920 enters bottom opening 918, connecting arms 934a, 934b rotate in an opposed direction and contact the molded guide ramp 938 on tissue forms 936a, 936b causing to tissue forms 936a, 936b to rotate about a rotation member coupling mounting bores 940a, 940b with body assembly 902. Eventually, tissue forms 936a, 936b rotate to a grasping position on either side of insertion head 988.

Following manipulation of tissue forms 936a, 936b to a grasping position, continual squeezing of body assembly 902 and trigger assembly 904 causes trigger 920 to insert further into bottom opening 918 such that interface channel 926 slides around distal connector 956. As trigger 920 inserts further into bottom opening 918, distal connector 956 reaches and end of interface channel 926 causing rotation member 944 to rotate about fulcrum connector 958 such that proximal connector 960 moves in a downward direction. Downward movement of proximal connector 960 causes channel 966 to move in a downward direction resulting in lever member 946 rotating about fulcrum connector 969. As channel 966 moves downward, proximal end 964 moves in a forward direction causing connecting tip 970 to direct insertion slide 972 to advance toward insertion head 988. As insertion head 988 advances, piercing members 982a, 982b and backspan member 986 cooperatively capture a bottom most fastener 1010 from fastener stack 994. Fastener 1010 is advanced through the capture zone 990 and into the target tissue zones 70 as previously described with respect to surgical instrument 700.

As trigger 920 is further squeezed and inserted into opening 918, ratchet member 925 releases. As piercing members 982a, 982b retract past fastener stack 994, spring feed assembly 998 advances the bottom most fastener 1010 into position for a future capture by piercing members 982a, 982b. As ratchet member 925 releases, spring assembly 932 interacts with upper engagement portion 930 allowing trigger 920 to return to its original position which in turn caused tissue forms 936a, 936b to release the grasped tissue. In addition, spring assembly 959 causes rotation member 944 to return to its original orientation such that piercing members 982a, 982b are retracted.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

The invention claimed is:

1. A method for deploying a fastener into skin tissue having an incision or wound, comprising:
    engaging a first side of skin tissue on a first side of a skin opening to expose an inner surface of that first side of the skin opening;
    engaging a second side of skin tissue on a second side of the skin opening to expose an inner surface of that second side o the skin opening; and
    driving a fastener into each of the exposed inner surfaces of the first and second sides of the skin opening such that the fastener resides in a substantially vertical orientation relative to a horizontal plane of an exterior skin surface.

2. The method of claim 1, wherein the driving step further comprises:
    simultaneously driving the fastener into each of the exposed inner surfaces of the first and second sides of the skin opening.

3. The method of claim 1, wherein the engaging steps are performed using a tissue manipulator assembly defining first and second tissue manipulator surfaces, the first and second tissue manipulator surfaces being spaced apart by a gap when engaged to the first and second sides of skin tissue.

4. A method for closing a skin opening, comprising:
    engaging a first side of a skin opening to expose an inner surface of the first side of the skin opening;
    engaging a second side of a skin opening to expose an inner surface of the second side of the skin opening;

simultaneously penetrating each of the exposed inner surfaces with a fastener such that the fastener is oriented in a substantially vertical orientation relative to a horizontal plane of an exterior surface of skin tissue; and releasing the first and second sides of the skin opening to allow the first and second sides to relax to a flat condition with the fastener deployed below the exterior surface of the skin tissue thereby retaining the first and second sides of the skin opening in close contact.

5. The method of claim 4, wherein the fastener comprises a bioabsorbable fastener that includes a pair of legs and a cross member between the two legs, each leg section including at least one barb that is oriented to resist withdrawal of the legs following deployment of the fastener into the exposed inner surfaces.

6. The method of claim 5, wherein the releasing step results in the at least one barb of each leg section resisting withdrawal from the corresponding exposed inner surface, and wherein the cross member retains the first and second sides of the skin opening in close contact.

7. A method for deploying a fastener into a skin opening, comprising:
- (a) engaging a first side of a skin opening with a first manipulator surface;
- (b) engaging a second side of the skin opening with a second manipulator surface, the first and second manipulator surfaces being spaced apart by a gap and defining a vertical plane within the gap;
- (c) exposing an inner surface on each of the first and second sides of the skin opening; and
- (d) manipulating an applicator assembly that releasably holds a fastener to deploy the fastener into the exposed inner surfaces of the first and second sides of the skin opening on opposed sides of the vertical plane such that the fastener is oriented in a substantially vertical orientation relative to a horizontal plane defined by an exterior skin surface.

8. The method of claim 7, wherein the fastener is bioabsorbable.

* * * * *

UNITED STATES PATENT AND TRADEMARK OFFICE
CERTIFICATE OF CORRECTION

| | | |
|---|---|---|
| PATENT NO. | : 9,713,472 B2 | Page 1 of 1 |
| APPLICATION NO. | : 15/145194 | |
| DATED | : July 25, 2017 | |
| INVENTOR(S) | : Peterson et al. | |

It is certified that error appears in the above-identified patent and that said Letters Patent is hereby corrected as shown below:

In the Claims

<u>Claim 1, Column 22, Line 47</u>:
After "side" delete "o" and insert -- of --.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*